United States Patent
Hojo et al.

(10) Patent No.: US 9,650,392 B2
(45) Date of Patent: May 16, 2017

(54) ELECTRODE ACTIVE MATERIAL FOR POWER STORAGE DEVICE, POWER STORAGE DEVICE, AND ELECTRONIC AND TRANSPORTATION DEVICE

(75) Inventors: Nobuhiko Hojo, Osaka (JP); Yu Ohtsuka, Osaka (JP); Takafumi Tsukagoshi, Osaka (JP); Yohji Misaki, Ehime (JP)

(73) Assignee: PANASONIC CORPORATION, Osaka (JP)

( * ) Notice: Subject to any disclaimer, the term of this patent is extended or adjusted under 35 U.S.C. 154(b) by 1447 days.

(21) Appl. No.: 13/393,519

(22) PCT Filed: Feb. 15, 2011

(86) PCT No.: PCT/JP2011/000836
§ 371 (c)(1),
(2), (4) Date: Feb. 29, 2012

(87) PCT Pub. No.: WO2011/099311
PCT Pub. Date: Aug. 18, 2011

(65) Prior Publication Data
US 2012/0156572 A1    Jun. 21, 2012

(30) Foreign Application Priority Data

Feb. 15, 2010 (JP) .................. 2010-030477
Feb. 15, 2010 (JP) .................. 2010-030478

(51) Int. Cl.
*H01M 4/60* (2006.01)
*C07D 495/04* (2006.01)
(Continued)

(52) U.S. Cl.
CPC ......... *C07D 495/04* (2013.01); *C07D 339/06* (2013.01); *C07D 409/04* (2013.01);
(Continued)

(58) Field of Classification Search
CPC .............................. H01M 4/604; H01M 4/608
See application file for complete search history.

(56) References Cited

U.S. PATENT DOCUMENTS

2004/0045818 A1   3/2004 Inatomi et al.
2004/0214082 A1   10/2004 Inatomi et al.
(Continued)

FOREIGN PATENT DOCUMENTS

JP   01-172382 A   7/1989
JP   10-505705 A   6/1998
(Continued)

OTHER PUBLICATIONS

Misaki, et al. (1992). Methylthio substituted 2,5-bis(1',3'-dithiol-2'-ylidene)-1,3,4,6-tetrathiapentalene. A Bis-Fused Tetrathiafulvalene. *Chemistry Letters*, 29(12), p. 2321-2324.
(Continued)

*Primary Examiner* — Ula C Ruddock
*Assistant Examiner* — Frank Chernow
(74) *Attorney, Agent, or Firm* — McDermott Will & Emery LLP

(57) ABSTRACT

Disclosed are an electrode active material for a power storage device and a power storage device including the same. The electrode active material includes a polymer that includes: a tetravalent group derived from a compound selected from the group consisting of EBDT and derivatives thereof, TTF and derivatives thereof, a condensation product of EBDT and TTF and derivatives thereof, and a TTF dimer and derivatives thereof; and a divalent group —S-A-S— where A is a divalent aliphatic group or a divalent group represented by the formula -E-D-E- where D represents a divalent alicyclic group, a divalent aromatic group, or a carbonyl group, and two Es each independently represent a divalent aliphatic group. Adjacent two tetravalent groups
(Continued)

mentioned above are linked by one or two divalent groups mentioned above.

23 Claims, 3 Drawing Sheets

(51) Int. Cl.

| | | |
|---|---|---|
| *C07D 339/06* | (2006.01) | |
| *C07D 409/04* | (2006.01) | |
| *C07D 495/02* | (2006.01) | |
| *C07D 495/14* | (2006.01) | |
| *H01G 11/48* | (2013.01) | |
| *H01G 11/60* | (2013.01) | |
| *H01G 11/62* | (2013.01) | |
| *H01M 10/052* | (2010.01) | |
| *H01M 10/0525* | (2010.01) | |
| *H01M 10/0569* | (2010.01) | |
| *H01G 11/50* | (2013.01) | |

(52) U.S. Cl.
CPC ......... *C07D 495/02* (2013.01); *C07D 495/14* (2013.01); *H01G 11/48* (2013.01); *H01G 11/50* (2013.01); *H01G 11/60* (2013.01); *H01G 11/62* (2013.01); *H01M 4/60* (2013.01); *H01M 4/604* (2013.01); *H01M 4/608* (2013.01); *H01M 10/052* (2013.01); *H01M 10/0525* (2013.01); *H01M 10/0569* (2013.01); *Y02E 60/13* (2013.01); *Y02T 10/7011* (2013.01); *Y02T 10/7022* (2013.01)

(56) References Cited

U.S. PATENT DOCUMENTS

| | | | |
|---|---|---|---|
| 2009/0111030 A1 | | 4/2009 | Hojo et al. |
| 2011/0003201 A1* | | 1/2011 | Tsukagoshi ............. H01M 4/60 429/207 |
| 2011/0091767 A1 | | 4/2011 | Hojo et al. |

FOREIGN PATENT DOCUMENTS

| | | |
|---|---|---|
| JP | 2004-111374 A | 4/2004 |
| JP | 2004-342605 A | 12/2004 |
| JP | 2007-305461 A | 11/2007 |
| JP | 2008-159275 A | 7/2008 |
| WO | WO 96/03778 A2 | 2/1996 |
| WO | WO 2007/132786 A1 | 11/2007 |
| WO | WO 2010/013491 A1 | 2/2010 |

OTHER PUBLICATIONS

Misaki, et al. (1995). A vinylogue of bis-fused tetrathiafulvalene: novel π-electron framework for two-dimensional organic metals. *J Mater Chem*,5(10), p. 1570-1579.

Moore, et al. (1992). New vinylogous tetrathiafulvalene (TTF) π-electron donors. *Tetrahedron Letters*, 33(10), p. 1373-1376.

(2004). Yamada, et al. (Eds.), *TTF Chemistry: Fundamentals and Applications of Tetrathiafulvalene* (p. 46-49 & 286-289). New York, NY: Springer.

International Search Report issued in International Patent Application No. PCT/JP2011/000836, dated Apr. 26, 2011.

* cited by examiner

ELECTRODE ACTIVE MATERIAL FOR POWER STORAGE DEVICE, POWER STORAGE DEVICE, AND ELECTRONIC AND TRANSPORTATION DEVICE

RELATED APPLICATIONS

This application is the U.S. National Phase under 35 U.S.C. §371 of International Application No. PCT/JP2011/000836, filed on Feb. 15, 2011, which in turn claims the benefit of Japanese Application No. 2010-030478, filed on Feb. 15, 2010, and Japanese Application No. 2010-030477, filed on Feb. 15, 2010, the disclosures of which Applications are incorporated by reference herein.

TECHNICAL FIELD

This invention relates to electrode active materials for power storage devices, power storage devices, and electronic and transportation devices. More particularly, the invention relates to an improvement in electrode active materials for power storage devices.

BACKGROUND ART

There has been a proliferation of devices requiring power sources that can be charged and discharged, such as hybrid electric vehicles, which operate on both energies of gasoline and electricity, uninterruptible power supplies, mobile communications devices, and portable electronic devices. This has lead to a significant increase in the demand for high performance power storage devices for use as the power source for such devices. Specifically, there is a demand for high performance power storage devices having a high output, a high capacity, and good cycle characteristics.

Various attempts have been made to heighten the performance of power storage devices. In particular, since an increase in the energy density of electrode active materials leads directly to an increase in the energy density of power storage devices themselves, electrode active materials are extensively studied. For example, organic compounds having a conjugated π electron cloud have been proposed as new electrode active materials that are expected to be charged and discharged at high rates (see PTLs 1 to 6).

PTL 1 discloses organic compounds with a conjugated π electron cloud, such as tetrathiafulvalene represented by the chemical structural formula (Q1) (hereinafter referred to as "TTF"). TTF has a high energy density of approximately 260 mAh/g.

[Chem. 1]

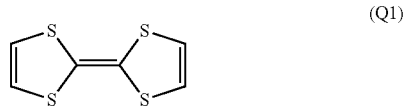

(Q1)

PTL 2 discloses organic compounds with a conjugated π electron cloud, such as 2,2'-ethanediylidene-bis-1,3-dithiol represented by the chemical structural formula (Q2) (hereinafter referred to as "EBDT"). EBDT has a high energy density of approximately 230 mAh/g. Also, the speed of the electrochemical reaction of EBDT is very high.

[Chem. 2]

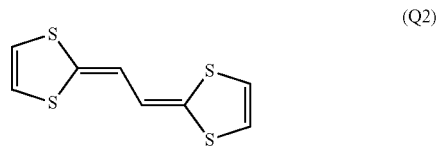

(Q2)

An electrolyte often contains a non-aqueous solvent (organic solvent) having the property of dissolving an organic compound of a low molecular weight. Therefore, in a system using an organic compound as an electrode active material, it may become necessary to suppress the dissolution of the electrode active material into an electrolyte. To solve this problem, PTL 3 discloses an electrode active material in which an organic compound having a conjugated π electron cloud is bonded to the main chain of a polymer compound. Examples of the polymer compound include polyacetylene and polymethyl methacrylate. An example of the organic compound having a conjugated π electron cloud is TTF.

PTL 4 discloses a TTF trimer represented by the chemical structural formula (Q3). Since the TTF trimer has an extended planar structure comprising a plurality of TTF skeletons, it is difficult to dissolve in an electrolyte. Therefore, an electrode active material for a power storage device including a TTF trimer has a high capacity, a high output, and good cycle characteristics.

[Chem. 3]

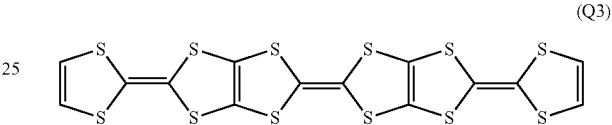

(Q3)

PTL 5 discloses organic compounds having skeletons represented by the chemical structural formulae (Q1), (Q2), and (Q3). Since these organic compounds have a planar molecular structure and have a conjugated π electron cloud in the direction perpendicular to the planar molecular structure, they tend to become crystalline upon charge/discharge. The use of an electrode active material including such an organic compound can provide a power storage device having a high capacity, a high output, and good cycle characteristics.

PTL 6 discloses a polymer having a main chain that includes the TTF skeleton represented by the chemical structural formula (Q1) as a repeat unit, and this polymer does not dissolve in an electrolyte. The use of the polymer of PTL 6 as an electrode active material can provide a power storage device having a high capacity, a high output, and good cycle characteristics.

CITATION LIST

Patent Literature

[PTL 1] Japanese Laid-Open Patent Publication No. 2004-111374
[PTL 2] Japanese Laid-Open Patent Publication No. 2004-342605
[PTL 3] Japanese Laid-Open Patent Publication No. 2007-305461
[PTL 4] Japanese Laid-Open Patent Publication No. 2008-159275
[PTL 5] International Publication No. WO 2007/132786
[PTL 6] International Publication No. WO 2010/013491

SUMMARY OF INVENTION

Technical Problem

The organic compounds having a conjugated π electron cloud recited in PTLs 1 and 2 are thought to have a high capacity, a high output, and good cycle characteristics, but they may dissolve in an electrolyte, depending on the composition of the electrolyte and the configuration of the power storage device. To suppress dissolution into an electrolyte, derivatization or polymerization is necessary. Derivatization is performed, for example, by introducing an insoluble functional group to both ends of the TTF skeleton or EBDT skeleton.

However, since the insoluble functional group does not participate in the oxidation-reduction reactions, the introduction of the insoluble functional group decreases the energy density of the reaction skeleton. Polymerization also requires the introduction of a functional group that does not participate in the oxidation-reduction reactions. Therefore, the resulting derivative or polymer has a lower energy density than the reaction skeleton, i.e., the TTF skeleton or EBDT skeleton, and it is difficult to heighten its energy density to that of the reaction skeleton.

In PTL 3, polymerization is performed by bonding the organic compound of PTL 1 having a conjugated π electron cloud to the main chain of the polymer compound. This polymerization does not require the introduction of a functional group that does not participate in the oxidation-reduction reactions. Therefore, the electrode active material of PTL 3 has a higher energy density than the electrode active material of PTL 1 or PTL 2 in which the insoluble functional group or the like is introduced. However, since the electrode active material of PTL 3 includes the main chain of the polymer compound, a further improvement in energy density is possible.

In the case of the TTF trimer of PTL 4, since the number of sites to which a functional group can be easily introduced is small, its molecular design is limited. Derivatives of the TTF trimer can be produced only by substituting the hydrogen atom bonded to the carbon atom contained in the TTF skeleton at the end of the molecule with a functional group. The characteristics of a power storage device, such as voltage and capacity, need to be changed according to the application. However, the TTF trimer does not allow such changes, since a large number of derivatives cannot be synthesized. That is, the TTF trimer has a problem in that the flexibility of material design is insufficient.

The organic compounds of PTL 5 are difficult to dissolve in an electrolyte and can provide power storage devices with good cycle characteristics, but a further improvement is possible.

The polymer of PTL 6 is synthesized through a coupling reaction carried out in the presence of a metal catalyst such as a Ni catalyst or a Pd catalyst. However, such a coupling reaction has the following problems:

(a) It is difficult to control the reaction, and the molecular-weight distribution of the resulting polymer tends to become outside the intended range.

(b) The resulting polymer tends to contain a metal catalyst, and the metal catalyst may affect battery performance.

(c) Such a metal catalyst as mentioned above is very expensive.

Also, depending on the kind of the polymer to be synthesized, the use of a reagent that is extremely reactive may become necessary, in which case a reaction must be carried out at a low temperature of, for example, −78° C. To carry out a reaction at a low temperature requires special reaction equipment. Also, such a reaction using a highly reactive reagent is difficult to control, thereby requiring a great deal of skill. Therefore, a further study is necessary for the industrial mass production of the polymer of PTL 6.

Also, to improve the cycle characteristics and output characteristics of a power storage device, it is thought to be effective to design a molecule that is crystalline, is difficult to dissolve in an electrolyte, and has a high energy density by derivatizing a molecule including a reaction skeleton such as an EBDT skeleton or TTF skeleton. However, PTLs 1 to 6 fail to provide sufficient information on what kind of molecular structure should be designed to obtain a synthesis method which is easy and convenient for scale up.

An object of the invention is to provide an electrode active material for a power storage device having a high energy density, a power storage device including the electrode active material and having good cycle characteristics and output characteristics, and electronic and transportation devices having the power storage device as a power source.

Solution to Problem

The electrode active material for a power storage device according to the invention includes a polymer or a compound having a repeat unit X represented by the following general formula (X) and a repeat unit Y. Adjacent two repeat units Y are linked by one or two repeat units X, and the repeat unit Y is at least one selected from the group consisting of a repeat unit Y1 represented by the following general formula (Y1), a repeat unit Y2 represented by the following general formula (Y2), a repeat unit Y3 represented by the following general formula (Y3), and a repeat unit Y4 represented by the following general formula (Y4).

In the description given below, the repeat unit X is abbreviated as the "unit X", the repeat unit Y as the "unit Y", the repeat unit Y1 as the "unit Y1", the repeat unit Y2 as the "unit Y2", the repeat unit Y3 as the "unit Y3", and the repeat unit Y4 as the "unit Y4".

[Chem. 4]

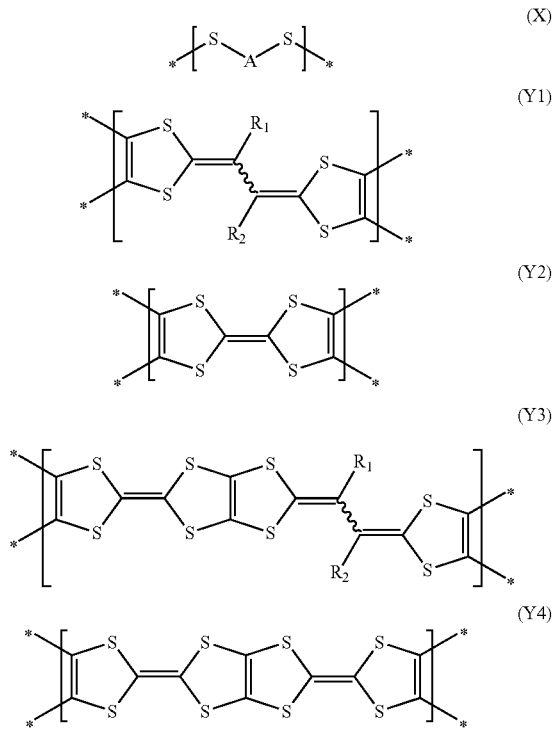

In the formula (X), A represents a divalent aliphatic group or a divalent group represented by the formula -E-D-E- where D represents a divalent alicyclic group, a divalent aromatic group, or a carbonyl group, and two Es each independently represent a divalent aliphatic group. In the formula (Y1) and the formula (Y3), $R_1$ and $R_2$ each independently represent a hydrogen atom, a fluorine atom, a monovalent aliphatic group, or a monovalent aromatic group. The monovalent and divalent aliphatic groups, the divalent alicyclic group, and the monovalent and divalent aromatic groups can each independently contain at least one kind of atom selected from the group consisting of halogen atom, nitrogen atom, oxygen atom, sulfur atom, and silicon atom.

The power storage device of the invention includes a positive electrode including a positive electrode active material, a negative electrode including a negative electrode active material, and an electrolyte, and at least one of the positive electrode active material and the negative electrode active material is the above-mentioned electrode active material for a power storage device.

The electronic device of the invention includes the above-mentioned power storage device as a power source.

The transportation device of the invention includes the above-mentioned power storage device as a power source.

Advantageous Effects of Invention

The electrode active material for a power storage device according to the invention (hereinafter referred to as simply the "electrode active material") has a high energy density, and is difficult to dissolve in an electrolyte although it includes a polymer that is an organic compound.

The power storage device of the invention uses such an electrode active material, thus having a high energy density and good cycle characteristics and output characteristics. Therefore, the power storage device of the invention is useful as the power source for, for example, electronic devices and transportation devices.

While the novel features of the invention are set forth particularly in the appended claims, the invention, both as to organization and content, will be better understood and appreciated, along with other objects and features thereof, from the following detailed description taken in conjunction with the drawings.

DESCRIPTION OF EMBODIMENTS

Figure 1:
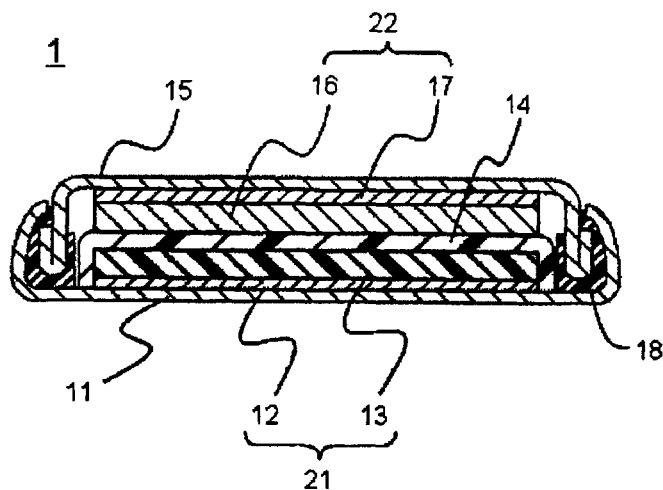
FIG. 1 is a longitudinal sectional view schematically showing the structure of a coin-shaped power storage device in an embodiment of the invention.

The inventors have conducted diligent studies to find new electrode active materials which can solve the problems with conventional art. As a result, they have found a polymer or compound (hereinafter collectively referred to as "polymer") comprising reaction skeletons such as EBDT skeletons or TTF skeletons linked by a specific divalent group. They have found that this polymer has a higher energy density than the reaction skeleton itself, has good cycle characteristics, is difficult to dissolve in an electrolyte, and is very useful as an electrode active material. Further, this polymer can be synthesized by a method that is very easy and convenient for scale up without requiring an expensive metal catalyst or an ultra-low temperature reaction in the synthesis process. This polymer has such good characteristics probably for the following reasons.

When reaction skeletons such as EBDT skeletons or TTF skeletons are linked by a specific divalent group, the electrochemical reaction of the reaction skeletons proceeds in the same manner as that of the reaction skeletons which are present alone, without being adversely affected by the bonding sites. Therefore, within the polymer, the reaction speed of the electrochemical reaction of the reaction skeletons does not become low. Also, linking the reaction skeletons by a specific divalent group can provide a polymer that is difficult to dissolve in an electrolyte. Thus, the cycle characteristics of the power storage device are improved. Also, linkage by a specific divalent group increases the reaction potential of the reaction skeletons themselves. As a result, the voltage becomes high, and a high energy density is achieved.

Further, a polymer comprising reaction skeletons linked by two specific divalent groups has two bonding sites in the molecule, and hence, rotation or twist of the molecule from the bonding sites is suppressed. Thus, such molecules tend to have a planar structure. When the molecules have a planar structure, the molecules are stacked to form a stack of molecules, and the molecules tend to become crystalline. Also, the length of the molecular chain becomes long, compared with the reaction skeleton itself, and the intermolecular force which acts between the molecules increases, and as a result, the stability as a crystal increases. For these reasons, a polymer comprising reaction skeletons linked by two specific divalent groups (a two-linking polymer described below) becomes even more difficult to dissolve in an electrolyte.

The inventors have completed the invention by finding that linking reaction skeletons such as EBDT skeletons or TTF skeletons by one or more specific divalent groups results in a polymer having a high energy density and being difficult to dissolve in an electrolyte, and that this polymer can significantly improve the cycle characteristics and output characteristics of a power storage device.

The electrode active material of the invention is characterized by including a specific polymer. This polymer includes a unit X and a unit Y, and adjacent two units Y are linked by one or two units X. The unit Y is at least one selected from the group consisting of a unit Y1, a unit Y2, a unit Y3, and a unit Y4.

The unit Y has four bonding sites, and preferably, at least two of the bonding sites are each bonded to the unit X, while the remaining bonding sites not bonded to the unit X are bonded to a group —R where R represents a hydrogen atom, a fluorine atom, a monovalent aliphatic group, or a monovalent aromatic group, and the monovalent aliphatic group and the monovalent aromatic group each independently contain at least one kind of atom selected from the group consisting of halogen atom, nitrogen atom, oxygen atom, sulfur atom, and silicon atom. When there are a plurality of bonding sites not bonded to the unit X and these bonding sides are substituted with a plurality of groups —R, the plurality of groups —R may be the same or different.

Also, when the unit Y is positioned at the end of the polymer, three of the four bonding sites of the unit Y may be each bonded to the group —R where R is as defined above.

Further, when the unit X is positioned at the end of the polymer, one of the two bonding sites of the unit X may be bonded to the unit Y, while the other bonding site may be bonded to the group —R where R is as defined above. When two units Y are bonded to the unit X, the two units Y may be the same or different.

The polymers included in the electrode active materials of the invention encompass one-linking polymers, one-linking polymers in a different mode, two-linking polymers, and irregularly-linking polymers. In a one-linking polymer, adjacent two units Y are linked by one unit X. In a two-linking polymer, adjacent two units Y are linked by two units X. An irregularly-linking polymer has a portion in which adjacent two units Y are linked by one unit X and a portion in which adjacent two units Y are linked by two units X.

The one-linking polymer preferably includes at least one selected from the group consisting of a repeat unit Z1 (unit Z1) represented by the following general formula (Z1), a repeat unit Z2 (unit Z2) represented by the following general formula (Z2), a repeat unit Z3 (unit Z3) represented by the following general formula (Z3), and a repeat unit Z4 (unit Z4) represented by the following general formula (Z4).

[Chem. 5]

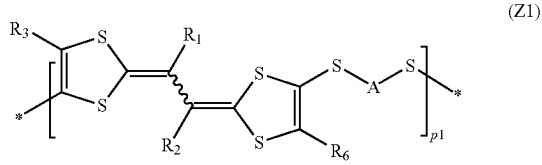

(Z1)

[Chem. 6]

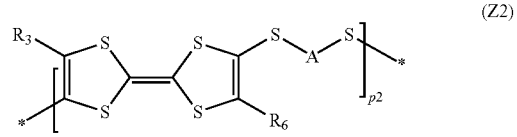

(Z2)

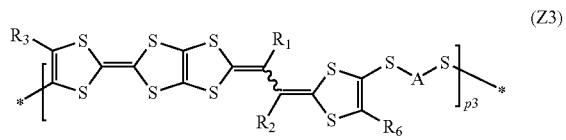

(Z3)

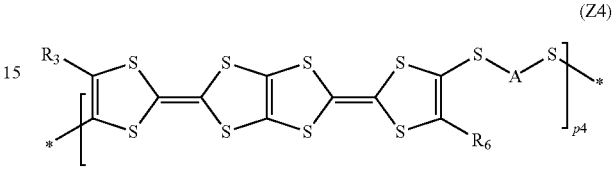

(Z4)

In the formulae (Z1) to (Z4), A represents a divalent aliphatic group or a divalent group represented by the formula -E-D-E- where D represents a divalent alicyclic group, a divalent aromatic group, or a carbonyl group, and two Es each independently represent a divalent aliphatic group. $R_1$ to $R_3$ and $R_6$ each independently represent a hydrogen atom, a fluorine atom, a monovalent aliphatic group, or a monovalent aromatic group. The monovalent and divalent aliphatic groups, the divalent alicyclic group, and the monovalent and divalent aromatic groups can each independently contain at least one kind of atom selected from the group consisting of halogen atom, nitrogen atom, oxygen atom, sulfur atom, and silicon atom. p1 to p4 each represent the total number of repetition of the units Z1 to Z4 in the one-linking polymer, and represent a real number of 2 or more.

The above respective formulae show repeat units with trans-type bonding positions for convenience sake; however, there are actually polymers comprising repeat units with trans-type bonding positions, polymers comprising repeat units with cis-type bonding positions, and polymers in which repeat units with trans-type bonding positions and repeat units with cis-type bonding positions are mixed. The polymers used in the invention encompass all of them.

Among the one-linking polymers, a one-linking polymer (1) is preferable. Examples of the one-linking polymer (1) include at least one selected from the group consisting of a polymer 1a represented by the following general formula (1a), a polymer 1b represented by the following general formula (1b), a polymer 1c represented by the following general formula (1c), a polymer 1d represented by the following general formula (1d), a polymer 1e represented by the following general formula (1e), and a polymer 1f represented by the following general formula (1f).

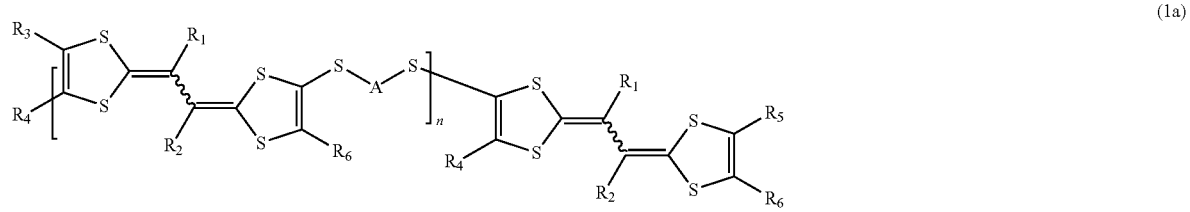

(1a)

-continued (1b)
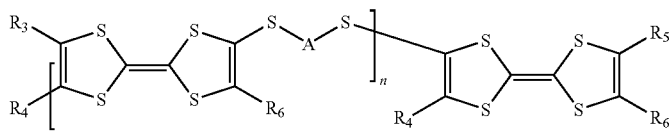

(1c)
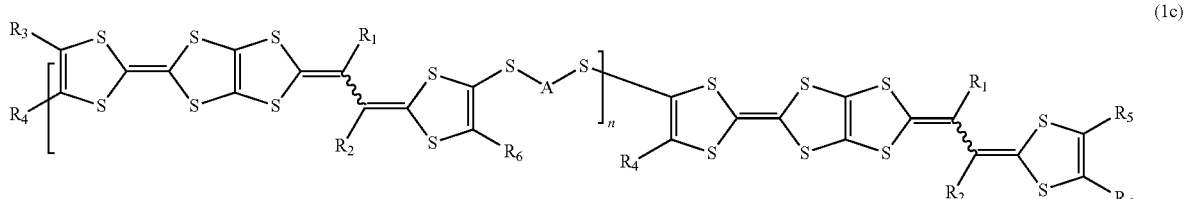

(1d)
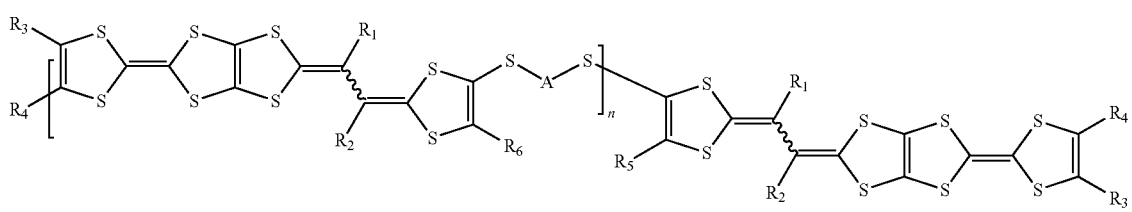

(1e)
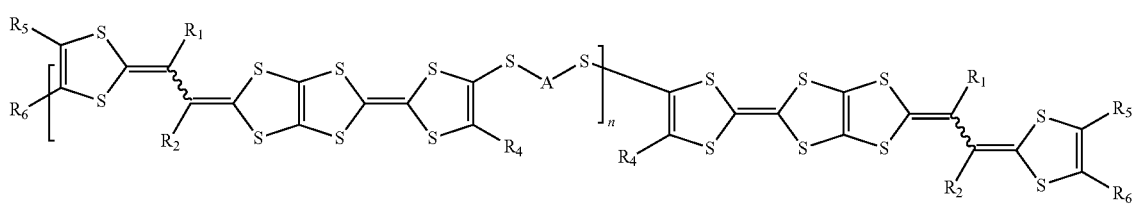

(1f)
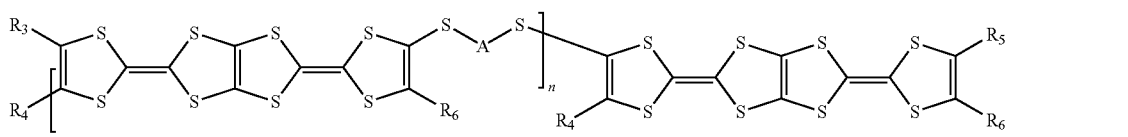

In the above respective formulae, A, $R_1$ to $R_3$, and $R_6$ are as defined above. $R_4$ and $R_5$ each independently represent a hydrogen atom, a fluorine atom, a monovalent aliphatic group, or a monovalent aromatic group. The monovalent aliphatic group and the monovalent aromatic group can contain at least one kind of atom selected from the group consisting of halogen atom, nitrogen atom, oxygen atom, sulfur atom, and silicon atom. $R_3$ and $R_4$ bonded to adjacent carbon atoms can be joined to form a ring, and $R_5$ and $R_6$ bonded to adjacent carbon atoms can be joined to form a ring. n represents a real number of 1 or more.

The one-linking polymer in a different mode preferably includes at least one selected from the group consisting of a repeat unit Z6 (unit Z6) represented by the following general formula (Z6), a repeat unit Z7 (unit Z7) represented by the following general formula (Z7), a repeat unit Z8 (unit Z8) represented by the following general formula (Z8), a repeat unit Z9 (unit Z9) represented by the following general formula (Z9), and a repeat unit Z10 (unit Z10) represented by the following general formula (Z10).

[Chem. 7]

(Z6)
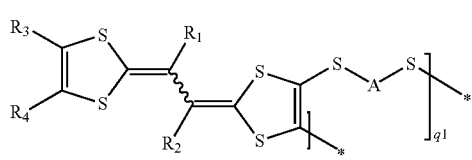

-continued (Z7)
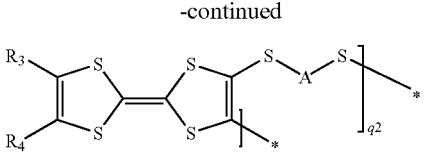

(Z8)
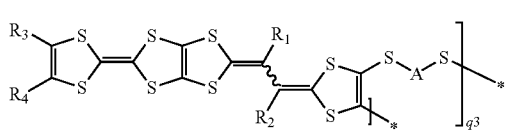

(Z9)
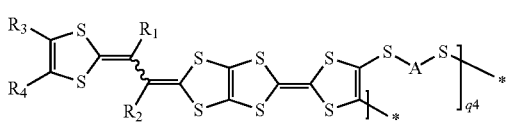

(Z10)
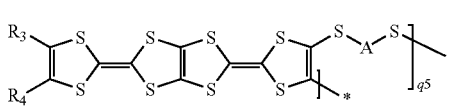

In the above respective formulae, A and $R_1$ to $R_4$ are as defined above. q1 to q5 each represent the total number of repetition of the units Z6 to Z10 in the one-linking polymer in the different mode, and represent a real number of 2 or more.

The above respective formulae show repeat units with trans-type bonding positions for convenience sake; however, there are actually polymers comprising repeat units with trans-type bonding positions, polymers comprising repeat units with cis-type bonding positions, and polymers in which repeat units with trans-type bonding positions and repeat units with cis-type bonding positions are mixed. The polymers used in the invention encompass all of them.

Among the one-linking polymers in the different mode, a one-linking polymer (2) is preferable. Examples of the one-linking polymer (2) include at least one selected from the group consisting of a polymer 2a represented by the following general formula (2a), a polymer 2b represented by the following general formula (2b), a polymer 2c represented by the following general formula (2c), a polymer 2d represented by the following general formula (2d), a polymer 2e represented by the following general formula (2e), and a polymer 2f represented by the following general formula (2f).

[Chem. 8]

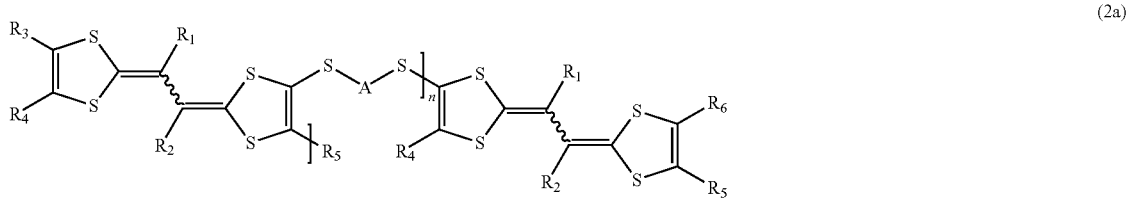

(2a)

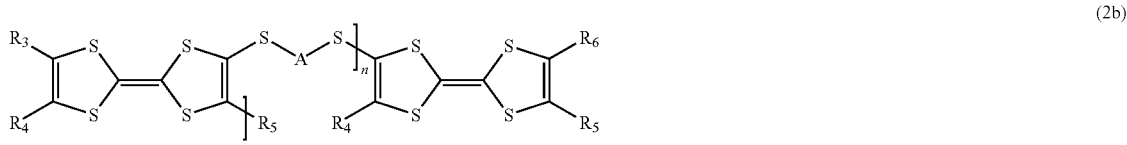

(2b)

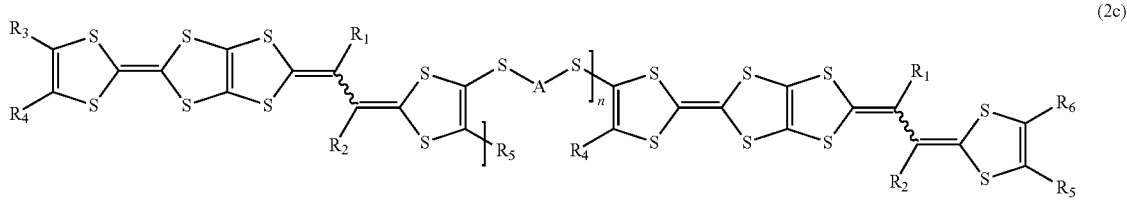

(2c)

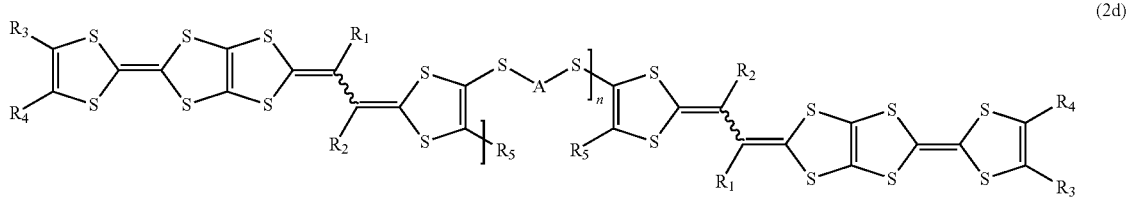

(2d)

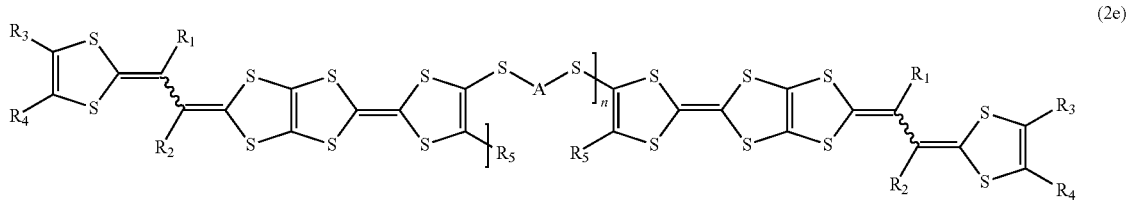

(2e)

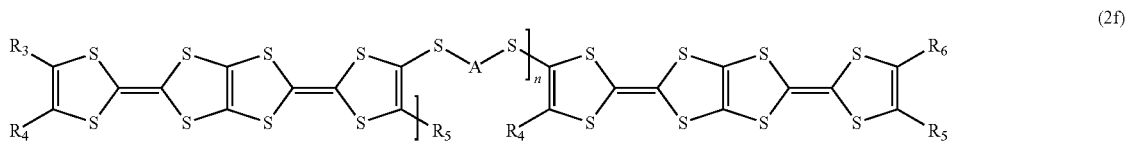

(2f)

In the above respective formulae, A, $R_1$ to $R_6$, and n are as defined above. $R_3$ and $R_4$ bonded to adjacent carbon atoms can be joined to form a ring, and $R_5$ and $R_6$ bonded to adjacent carbon atoms can be joined to form a ring.

The two-linking polymer preferably includes at least one selected from the group consisting of a repeat unit Z11 (unit Z11) represented by the following general formula (Z11), a repeat unit Z12 (unit Z12) represented by the following general formula (Z12), a repeat unit Z13 (unit Z13) represented by the following general formula (Z13), and a repeat unit Z14 (unit Z14) represented by the following general formula (Z14).

[Chem. 9]

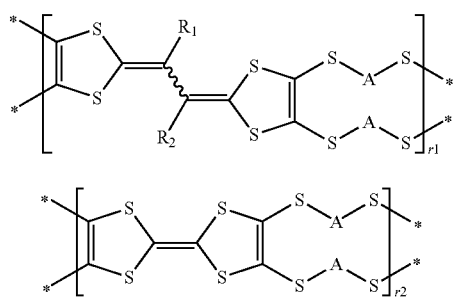

(Z11)

(Z12)

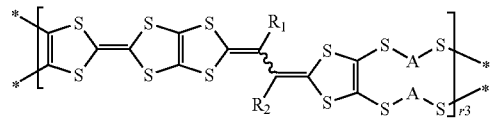

(Z13)

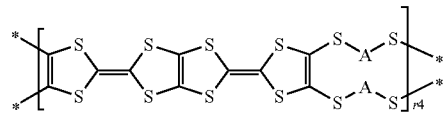

(Z14)

In the above respective formulae, A, $R_1$, and $R_2$ are as defined above. r1 to r4 each represent the total number of repetition of the units Z11 to Z14 in the two-linking polymer, and represents a real number of 2 or more.

Among the two-linking polymers, a two-linking polymer (3) is preferable. Examples of the two-linking polymer (3) include at least one selected from the group consisting of a polymer 3a represented by the following general formula (3a), a polymer 3b represented by the following general formula (3b), a polymer 3c represented by the following general formula (3c), a polymer 3d represented by the following general formula (3d), a polymer 3e represented by the following general formula (3e), and a polymer 3f represented by the following general formula (3f).

[Chem. 10]

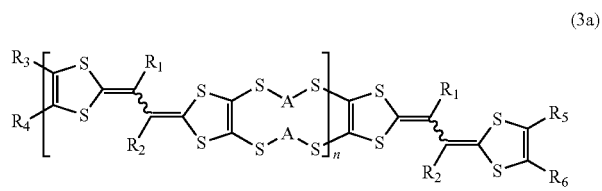 

(3a) (3b)

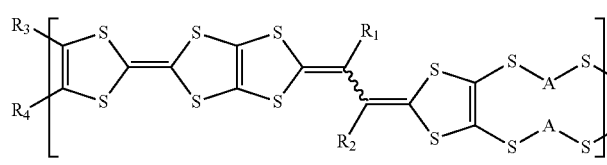

(3c)

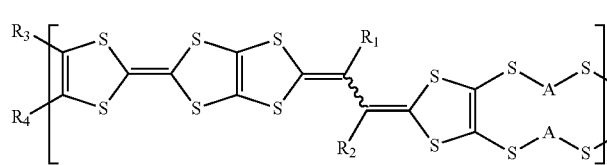

(3d)

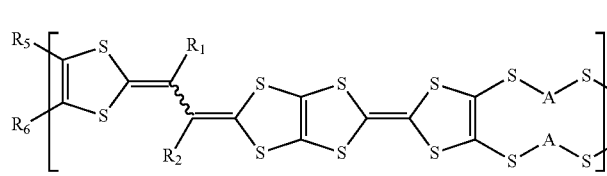

(3e)

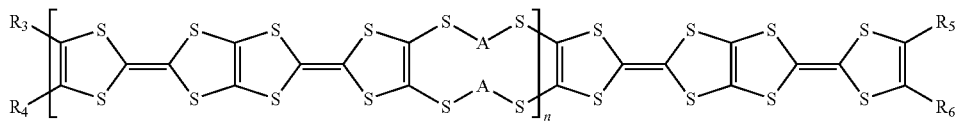

(3f)

In the above respective formulae, A, $R_1$ to $R_6$, and n are as defined above. $R_3$ and $R_4$ bonded to adjacent carbon atoms can be joined to form a ring, and $R_5$ and $R_6$ bonded to adjacent carbon atoms can be joined to form a ring.

A preferable example of the irregularly-linking polymer is an irregularly-linking polymer (4) including a repeat unit I and a repeat unit II. Examples of the repeat unit I include at least one selected from the group consisting of the unit Z1, the unit Z2, the unit Z3, and the unit Z4. Examples of the repeat unit II include at least one selected from the group consisting of the unit Z11, the unit Z12, the unit Z13, and the unit Z14.

In the respective general formulas recited herein, the divalent aliphatic group is preferably an alkylene group, an alkenylene group, or an alkynylene group.

In the divalent group -E-D-E-, the divalent alicyclic group represented by the character D is preferably a cycloalkylene group. Each of the divalent aliphatic groups represented by the character E is preferably an alkylene group, an alkenylene group, or an alkynylene group. Among them, the alkylene group is preferable, and a linear alkylene group having 1 to 4 carbon atoms is more preferable.

In the divalent group -E-D-E-, the divalent aromatic group represented by the character D is preferably an arylene group, more preferably a phenylene group, and even more preferably a p-phenylene group. Each of the divalent aliphatic groups represented by the character E is preferably an alkylene group, an alkenylene group, or an alkynylene group. Among them, the alkylene group is preferable, and a linear alkylene group having 1 to 4 carbon atoms is more preferable.

In the respective general formulae recited herein, the monovalent aliphatic group is preferably a monovalent group represented by the formula —$(S)_f$—Rb or the formula —$(S)_f$—Ra—(CO—O)$_g$—Rb where Ra represents an alkylene group, Rb represents a monovalent aliphatic group, the monovalent aliphatic group can contain at least one kind of atom selected from the group consisting of halogen atom, nitrogen atom, oxygen atom, sulfur atom, and silicon atom, and f and g each independently represent 0 or 1. The alkylene group represented by Ra is preferably a linear alkylene group having 1 to 6 carbon atoms, and more preferably a linear alkylene group having 1 to 4 carbon atoms. The monovalent aliphatic group represented by Rb is preferably an alkyl group having 1 to 6 carbon atoms, and more preferably a linear alkyl group having 1 to 6 carbon atoms. Examples of such monovalent aliphatic groups include an alkyl group, an alkylthio group, an alkyloxycarbonylalkyl group, and an alkyloxycarbonylalkylthio group.

In the respective general formulae recited herein, the monovalent aromatic group is preferably a monovalent group represented by the formula —$(S)_h$—(Ra)$_i$—Rc where Ra represents an alkylene group, Rc represents a monovalent aromatic group, the monovalent aromatic group can contain at least one kind of atom selected from the group consisting of halogen atom, nitrogen atom, oxygen atom, sulfur atom, and silicon atom, and h and i each independently represent 0 or 1. The alkylene group represented by Ra is preferably a linear alkylene group having 1 to 6 carbon atoms, and more preferably a linear alkylene group having 1 to 4 carbon atoms. The monovalent aromatic group represented by Rc is preferably an aryl group, and more preferably a phenyl group. Examples of such monovalent aromatic groups include an aryl group, an arylthio group, an arylalkyl group, and an arylalkylthio group.

In the above-mentioned polymers, the total number of repetition of the unit Y is preferably 6 or more. In this case, the resistance of the polymers to dissolution into an electrolyte and the energy density are further heightened.

The electrode active materials of the invention including these polymers have a high energy density in the battery reaction and are resistant to dissolution in an electrolyte. Thus, they are useful as the electrode active materials for various power storage devices. Also, since these polymers are organic compounds, they are light-weight, compared with electrode active materials comprising inorganic compounds. Therefore, the electrode active materials of the invention including these polymers also contribute to reduction in the weight of power storage devices.

Further, the power storage device of the invention includes a positive electrode including a positive electrode active material, a negative electrode including a negative electrode active material, and an electrolyte, and at least one of the positive electrode active material and the negative electrode active material is the above-described electrode active material. Due to the inclusion of the electrode active material, the power storage device has good cycle characteristics and output characteristics.

In the power storage device, the electrolyte preferably includes a non-aqueous solvent with a dielectric constant of 10 to 30 and a supporting salt comprising an anion and a cation dissolved in the non-aqueous solvent. The non-aqueous solvent is preferably a mixture of a non-aqueous solvent with a dielectric constant of 10 or less and a non-aqueous solvent with a dielectric constant of 30 or more. The non-aqueous solvent with a dielectric constant of 10 or less is preferably at least one selected from the group consisting of chain carbonic acid esters, chain carboxylic acid esters, and chain ethers, and the non-aqueous solvent with a dielectric constant of 30 or more is preferably at least one selected from the group consisting of cyclic carbonic acid esters and cyclic ethers.

The cation contained in the supporting salt is preferably a quaternary ammonium ion or a lithium ion. The negative electrode preferably includes lithium metal, a lithium alloy, or a material capable of absorbing and desorbing lithium ions.

Further, the electronic and transportation devices of the invention include the above-described power storage device as a power source, and are thus capable of performing their functions over a long period of time stably.

In the respective general formulae recited herein, the respective functional groups represented by the characters A, D, E, R, $R_1$ to $R_6$, and Ra to Rc are as follows.

Examples of divalent aliphatic groups include divalent chain saturated aliphatic groups, divalent cyclic saturated aliphatic groups, divalent chain unsaturated aliphatic groups, and divalent cyclic unsaturated aliphatic groups.

Examples of divalent chain saturated aliphatic groups include alkylene groups. Examples of alkylene groups include linear alkylene groups having 1 to 6 carbon atoms, such as methylene, ethylene, trimethylene, tetramethylene, pentamethylene, and hexamethylene. Among them, linear alkylene groups having 1 to 4 carbon atoms are preferable. Examples of divalent cyclic saturated aliphatic groups include cycloalkylene groups. Examples of cycloalkylene groups include cycloalkylene groups having 3 to 8 carbon atoms, such as cyclopropylene, cyclobutylene, cyclopentylene, and cyclohexylene.

Examples of divalent chain unsaturated aliphatic groups include alkenylene groups and alkynylene groups. Examples of alkenylene groups include linear or branched alkenylene groups having 2 to 6 carbon atoms, such as vinylene, 1-propenylene, 2-propenylene, 1-methyl-1-propenylene, 2-methyl-1-propenylene, 2-methyl-2-propenylene, 2-propenylene, 1-butenylene, 2-butenylene, and 3-butenylene. These alkenylene groups encompass both trans isomers and cis isomers. The divalent chain unsaturated aliphatic group represented by the character A is preferably a linear alkenylene group having a methylene group at each end.

Examples of alkynylene groups include linear or branched alkynylene groups having 2 to 6 carbon atoms, such as ethynylene, 2-propynylene, 1-methyl-2-propynylene, 2-butynylene, and 3-butynylene. These alkynylene groups encompass both trans isomers and cis isomers. The divalent chain unsaturated aliphatic group represented by the character A is preferably a linear alkynylene group having a methylene group at each end.

Examples of divalent cyclic unsaturated aliphatic groups include cycloalkenylene groups and cycloalkynylene groups. Examples of cycloalkenylene groups include cycloalkenylene groups having 3 to 8 carbon atoms, such as cyclopropenylene, cyclobutenylene, cyclopentenylene, and cyclohexenylene. Examples of cycloalkynylene groups include cycloalkynylene groups having 3 to 8 carbon atoms, such as cyclopropynylene, cyclobutynylene, cyclopentynylene, and cyclohexynylene.

Examples of divalent aromatic groups include arylene groups. Examples of arylene groups include arylene groups having 6 to 10 carbon atoms, such as phenylene, tolylene, and naphthylene.

Example of monovalent aliphatic groups include monovalent chain saturated aliphatic groups, monovalent cyclic saturated aliphatic groups, monovalent chain unsaturated aliphatic groups, and monovalent cyclic unsaturated aliphatic groups.

Examples of monovalent chain saturated aliphatic groups include alkyl groups. Examples of alkyl groups include linear or branched alkyl groups having 1 to 6 carbon atoms, such as methyl, ethyl, n-propyl, iso-propyl, n-butyl, iso-butyl, tert-butyl, n-pentyl, and n-hexyl.

Examples of monovalent cyclic saturated aliphatic groups include cycloalkyl groups. Examples of cycloalkyl groups include cycloalkyl groups having 3 to 8 carbon atoms, such as cyclopropyl, cyclobutyl, cyclopentyl, and cyclohexyl.

Examples of monovalent chain unsaturated aliphatic groups include alkenyl groups and alkynyl groups. Examples of alkenyl groups include linear or branched alkenyl groups having 2 to 6 carbon atoms, such as vinyl, 1-propenyl, 2-propenyl, 1-methyl-1-propenyl, 2-methyl-1-propenyl, 2-methyl-2-propenyl, 2-propenyl, 1-butenyl, 2-butenyl, and 3-butenyl. Examples of alkynyl groups include linear or branched alkynyl groups having 2 to 6 carbon atoms, such as ethynyl, 2-propynyl, 1-methyl-2-propynyl, 2-butynyl, and 3-butynyl. These alkenyl groups and alkynyl groups encompass both trans isomers and cis isomers.

Examples of monovalent cyclic unsaturated aliphatic groups include cycloalkenyl groups. Examples of cycloalkenyl groups include cycloalkenyl groups having 3 to 8 carbon atoms, such as cyclopropenyl, cyclobutenyl, cyclopentenyl, cyclohexenyl, methyl cyclopentenyl, and methyl cyclohexenyl.

Examples of monovalent aromatic groups include aryl groups. Examples of aryl groups include aryl groups having 6 to 10 carbon atoms, such as phenyl, tolyl, and naphthyl.

The monovalent and divalent aliphatic groups (hereinafter may also be referred to as collectively "aliphatic groups") and the monovalent and divalent aromatic groups (hereinafter may also be referred to as collectively "aromatic groups") can contain one or more atoms (hereinafter may also be referred to as collectively "atoms G") selected from the group consisting of halogen atom, nitrogen atom, oxygen atom, sulfur atom, and silicon atom. One halogen atom is substituted for one hydrogen atom bonded to a carbon atom in an aliphatic group or an aromatic group. Examples of halogen atoms include fluorine, chlorine, bromine, and iodine. An oxygen atom serving as an oxo group is substituted for two hydrogen atoms bonded to carbon atoms in an aliphatic group or an aromatic group.

Further, a group containing one or more atoms G other than halogen atoms may be substituted for hydrogen atoms bonded to carbon atoms in an aliphatic group or an aromatic group. Examples of nitrogen-atom containing groups include a nitro group, an amino group, an amide group, an imino group, and a cyano group. Examples of oxygen-atom containing groups include a hydroxyl group and a carboxyl group. Examples of sulfur-atom containing groups include a sulfo group, a sulfino group, a sulfeno group, and a mercapto group. Examples of silicon-atom containing groups include a silyl group. The aliphatic groups and the aromatic groups can contain at least one selected from the various functional groups mentioned above.

Further, the aliphatic groups and the aromatic groups can contain an aryl group such as a phenyl group as a substituent.

Some of the chemical structural formulae recited herein may contain the following structure in which the bond between adjacent two carbon atoms is shown by the wavy line.

[Chem. 11]

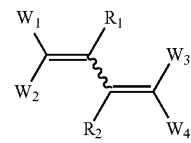

In the formula, $R_1$ and $R_2$ are as defined above. $W_1$ to $W_4$ each independently represent an organic group.

Herein, this structure includes the following three structures.

[Chem. 12]

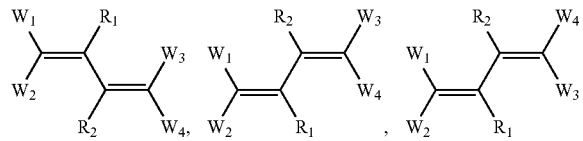

In the formula, $R_1$, $R_2$, and $W_1$ to $W_4$ are as defined above.

Next, the electrode active materials, the power storage device, and the electronic and transportation devices according to the invention are described more specifically one by one.

[Electrode Active Material]

The polymers used as the electrode active materials in the invention include units X and units Y, and adjacent two units Y are linked by one or two units X. That is, the units X and the units Y are alternately linked. These polymers may end with either one of the units X and Y, but they preferably end with the unit Y.

The polymers of the invention have a high energy density, because the units X and the units Y that cause an electrochemical reaction (oxidation-reduction reaction) are alternately linked, thereby suppressing a decrease in the oxidation/reduction performance of the units Y. Also, since the units X and the units Y are alternately linked, the symmetry and flatness of the molecular structure are increased, and the polymers of the invention stably exhibit resistance to dissolution in the non-aqueous solvent contained in an electrolyte. In addition, the polymers of the invention have an extended long flat molecule compared with a monomer of a reaction skeleton such as TTF or EBDT. Thus, the molecules are stacked, and a strong attraction occurs between the molecules. The intermolecular attraction is a cause of the resistance to dissolution in an electrolyte.

Further, the polymers of the invention are characterized by high flexibility in material design. In the case of the polymers of the invention, a large number of derivatives having different molecular structures can be synthesized relatively easily by selecting the structure of the -A- portion in the unit X or substituting the hydrogen atom bonded to the carbon atom forming the carbon-carbon single bond included in the unit Y with a monovalent aliphatic group or a monovalent aromatic group. Therefore, even if the specifications of the power storage device are changed, a derivative having a suitable molecular structure can be easily selected according to the change in specifications.

The unit X is a divalent group represented by the formula —S-A-S— where A is as defined above. The unit Y is at least one selected from the group consisting of the unit Y1, the unit Y2, the unit Y3, and the unit Y4. The unit Y1 is a tetravalent group comprising EBDT or a derivative thereof from which four hydrogen atoms at predetermined positions are removed. The unit Y2 is a tetravalent group comprising TTF or a derivative thereof from which four hydrogen atoms at predetermined positions are removed. The unit Y3 is a tetravalent group comprising a condensation product of EBDT and TTF or a derivative thereof from which four hydrogen atoms at predetermined positions are removed. The unit Y4 is a tetravalent group comprising a condensation product of two TTF (hereinafter referred to as "TTP") or a derivative thereof from which four hydrogen atoms at predetermined positions are removed.

The polymers of the invention are characterized in that the molecular structure is symmetrical and flat and that the structure does not change significantly upon oxidation-reduction reaction. Also, the polymers of the invention have a reaction skeleton such as an EBDT skeleton or a TTF skeleton in the molecule, and a conjugated n electron cloud capable of donating and accepting electrons is formed on the molecule. Donation and acceptance of electrons proceed through oxidation-reduction reactions of the reaction skeleton. For example, upon an oxidation reaction (charge reaction), the reaction skeleton is oxidized, and the anion in the electrolyte is coordinated to the conjugated n electron cloud. Upon a reduction reaction (discharge reaction), the anion coordinated to the conjugated n electron cloud is released. This reaction can be utilized as a power storage reaction.

Also, it is the reaction skeleton such as an EBDT skeleton or a TTF skeleton itself that is important for good oxidation/reduction characteristics. Thus, the functional groups the reaction skeleton has, i.e., the functional groups represented by the characters $R_1$ and $R_2$ in the unit Y1 and the unit Y3, are not particularly limited in terms of the kind and structure. It should be noted that an EBDT skeleton and a TTF skeleton with various functional groups have oxidation/reduction characteristics equivalent to those of an EBDT skeleton and a TTF skeleton without any functional groups, and this has been reported, for example, in a document such as "TTF chemistry, Fundamentals and Applications of Tetrathiafulvalene" (edited by Junichi Yamada and Toyonari Sugimoto and published in 2004 by Kodansha Scientific Ltd.).

The polymers of the invention do not undergo a large structural change such as bond cleavage or recombination upon oxidation-reduction reactions. Due to such oxidation-reduction reactions, the electrode active materials of the invention can provide power storage devices with a high capacity, a high output, and good cycle characteristics and output characteristics. Examples of the polymers of the invention include one-linking polymers, one-linking polymers in a different mode, two-linking polymers, and irregularly-linking polymers.

A one-linking polymer is a polymer in which at least one selected from the units Z1, Z2, Z3, and Z4 is linked in the form of a chain. Among the one-linking polymers, a one-linking polymer (1) is preferable. Examples of the one-linking polymer (1) include the above-mentioned polymers 1a to 1f. Of the polymers 1a to 1f, polymers in which $R_1$ to $R_6$ are the same functional group are more preferable. Of the polymers 1a and 1c to 1e, polymers in which $R_1$ and $R_2$ are a hydrogen atom, a phenyl group, or a phenylthio group are preferable. Also, in the general formulae (1a) to (1f), when the value n is sufficiently high, these polymers are copolymers including the unit X and the unit Y.

Each of the units Z1 to Z4 contains one reaction skeleton such as a TTF skeleton, an EBDT skeleton, a fused skeleton of EBDT and TTF, or a TTP skeleton (hereinafter referred to as collectively "reaction skeleton" unless otherwise specified). The number of repetition (degree of polymerization) of the units Z1 to Z4 in the one-linking polymer is not particularly limited if it is 2 or more, but it is preferably a real number of 2 to 100. More preferably, the lower limit value for the number of repetition of the units Z1 to Z4 is 3. In a more preferable mode, the one-linking polymer contains the units Z1 to Z4, with the number of repetition being in the above range, and the end on the —S-A-S— side is bonded to the unit Y.

When the number of repetition of the units Z1 to Z4 is small, it is preferable to suitably select the composition of the non-aqueous solvent contained in the electrolyte, the configuration of the power storage device, the functional groups introduced into each unit, etc. in consideration of the dissolution into the electrolyte. On the other hand, when the number of repetition of the units Z1 to Z4 is large, a power storage device can be configured without any such limitations. When the number of repetition of the units Z1 to Z4 is large, the average molecular weight of the polymer is desirably 10,000 or more. When the reaction skeleton is an EBDT skeleton, the number of repetition of the reaction skeleton in the polymer is desirably approximately 25 or more.

Of the one-linking polymers 1a to 1f, the one-linking polymers 1a, 1b, 1d, and 1f are preferable.

More preferable examples of the one-linking polymer 1a include polymers (10) to (20) shown in Table 1 and Table 2 below. The polymers (10) to (14) are dimers of EBDT or derivatives thereof. The polymers (15) and (16) are trimers of EBDT or a derivative thereof. The polymers (17) to (20) are multimers of EBDT or derivatives thereof.

More preferable examples of the one-linking polymer 1b include polymers (21) to (26) shown in Table 3 below. The polymers (21) to (23) are dimers of TTF or derivatives thereof. The polymers (24) to (26) are multimers of TTF derivatives.

More preferable examples of the one-linking polymer 1d include polymers (27) to (31) shown in Table 4 below. The polymers (27) and (28) are dimers of a condensation product of EBDT and TTF or a derivative thereof. The polymers (29) to (31) are multimers of a condensation product of EBDT and TTF or derivatives thereof.

More preferable examples of the one-linking polymer 1f include a polymer (32) shown in Table 4 below. The polymer (32) is a dimer of a TTP derivative.

TABLE 1

| No. | Chemical structural formula |
|---|---|
| 10 | 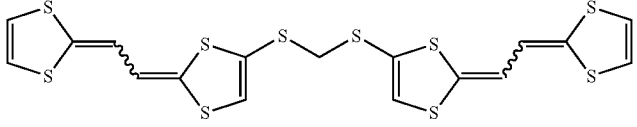 [SMILES: C1=CSC(=CC=C2SC=C(SCSC3=CSC(=CC=C4SC=CS4)S3)S2)S1] general formula (1a); A = methyl group, $R_1$ to $R_6$ = hydrogen atom, n = 1 |
| 11 | 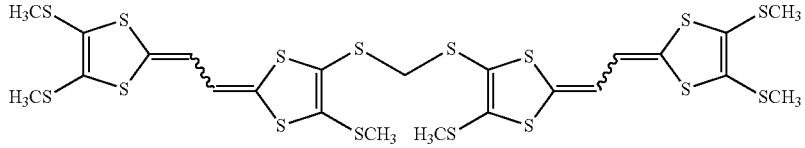 general formula (1a); A = methylene group, $R_1$ to $R_2$ = hydrogen atom, $R_3$ to $R_6$ = methylthio group, n = 1 |
| 12 | 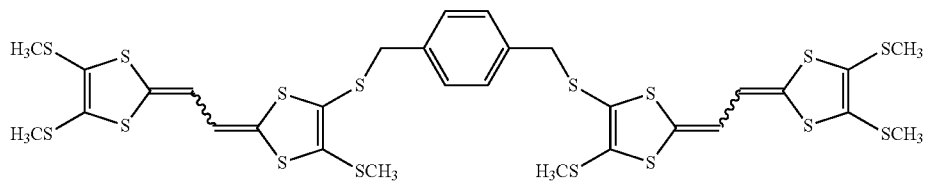 general formula (1a); A = —$CH_2$—Ph—$CH_2$— where —Ph— is phenylene group, $R_1$ to $R_2$ = hydrogen atom, $R_3$ to $R_6$ = methylthio group, n = 1, |
| 13 | 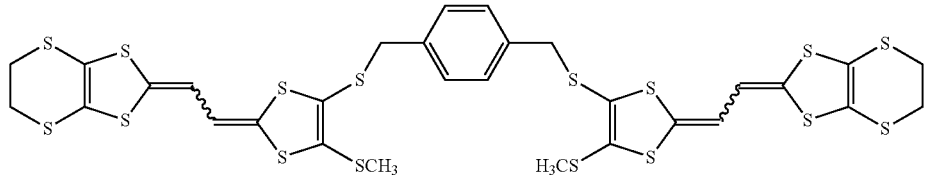 general formula (1a): A = —$CH_2$—Ph—$CH_2$— where —Ph— is phenylene group, $R_1$ to $R_2$ = hydrogen atom, $R_4$ not at end and $R_6$ = methylthio group, $R_3$ and $R_4$, $R_5$ and $R_6$ at end = joined to form ethylenedithio group, n = 1 |
| 14 | 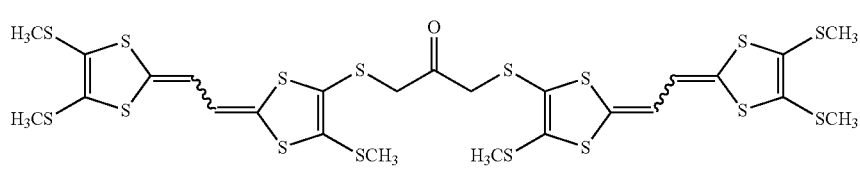 general formula (1a): A = —$CH_2$—CO—$CH_2$—, $R_1$ to $R_2$ = hydrogen atom, $R_3$ to $R_6$ = methylthio group, n = 1 |

TABLE 1-continued

| No. | Chemical structural formula |
|---|---|
| 15 | *(structure shown)* general formula (1a); A = methylene group, $R_1$ to $R_6$ = hydrogen atom, n = 2 |
| 16 | *(structure shown)* general formula (1a); A = methylene group, $R_1$ to $R_2$ = hydrogen atom, $R_3$ to $R_6$ = methylthio group, n = 2 |

TABLE 2

| No. | Chemical structural formula |
|---|---|
| 17 | *(structure shown)* general formula (1a); A = methylene group, $R_1$ to $R_6$ = hydrogen atom, n = real number of 3 or more |
| 18 | *(structure shown)* general formula (1a); A = methylene group, $R_1$ to $R_2$ = hydrogen atom, $R_3$ to $R_6$ = methylthio group, n = real number of 3 or more |
| 19 | *(structure shown)* general formula (1a): A = methylene group, $R_1$ to $R_2$ = hydrogen atom, $R_3$ to $R_6$ = —S(CH$_2$)$_2$COOC$_2$H$_5$, n = real number of 1 or more |
| 20 | *(structure shown)* general formula (1a): A = —CH$_2$—Ph—CH$_2$— where —Ph— is phenylene group, $R_1$ to $R_2$ = hydrogen atom, $R_3$ and $R_5$ = methylthio group, $R_4$ and $R_6$ = —S(CH$_2$)$_2$COOC$_2$H$_5$, n = real number of 1 or more |

TABLE 3

| No. | Chemical structural formula |
|---|---|
| 21 | general formula (1b): A = methylene group, $R_3$ to $R_6$: methylthio group, n = 1 |
| 22 | general formula (1b): A = —$CH_2$—Ph—$CH_2$— where —Ph— = phenylene group, $R_3$ to $R_6$ = thio methyl group, n = 1 |
| 23 | general formula (1b): A = —$CH_2$—CO—$CH_2$—, $R_3$ to $R_6$: methylthio group, n = 1 |
| 24 | general formula (1b): A = methylene group, $R_3$ to $R_6$: —$S(CH_2)_2COOC_2H_5$, n = real number of 1 or more |
| 25 | general formula (1b): A = ethylene group, $R_3$ to $R_6$: methylthio group, n = real number of 1 or more |
| 26 | general formula (1b): A = —$CH_2$—Ph—$CH_2$— where —Ph— = phenylene group, $R_3$ and $R_5$ = thio methyl group, $R_4$ and $R_6$ = —$S(CH)_2COOC_2H_5$, n = real number of 1 or more |

TABLE 4

| No. | Chemical structural formula |
|---|---|
| 27 | *[structure]*<br>general formula (1d); A = methylene group, $R_1$ to $R_6$ = hydrogen atom, n = 1 |
| 28 | *[structure]*<br>general formula (1d): A = methylene group, $R_1$ to $R_2$ = hydrogen atom,<br>$R_3$ to $R_6$ = methylthio group, n = 1 |
| 29 | *[structure]*<br>general formula (1d); A = methylene group, $R_1$ to $R_6$ = hydrogen atom,<br>n = real number of 3 or more |
| 30 | *[structure]*<br>general formula (1d): A = methylene group, $R_1$ to $R_2$ = hydrogen atom,<br>$R_3$ to $R_6$ = methylthio group, n = real number of 3 or more |
| 31 | *[structure]*<br>general formula (1d): A = methylene group, $R_1$ to $R_2$ = hydrogen atom,<br>$R_3$ at end and $R_5$ and $R_6$ not at end = methylthio group,<br>$R_4$ at end = —$S(CH_2)_2COOC_2H_5$, n = real number of 1 or more |
| 32 | *[structure]*<br>general formula (1f): A = methylene group,<br>$R_3$ to $R_6$ at end = methylthio group,<br>$R_4$ and $R_6$ not at end = —$S(CH_2)_2COOC_2H_5$, n = 1 |

The one-linking polymer in a different mode is preferably a polymer in which at least one selected from the units Z6, Z7, Z8, Z9, and Z10 is linked in a zigzag. Among such one-linking polymers, the one-linking polymer (2) is preferable. Examples of the one-linking polymer (2) include the above-mentioned polymers 2a to 2f. Of the polymers 2a to 2f, polymers in which $R_1$ to $R_6$ are the same functional group are more preferable.

Of the polymers 2a and 2c to 2e, polymers in which $R_1$ and $R_2$ are a hydrogen atom, a phenyl group, or a phenylthio group are preferable. Also, in the general formulae (2a) to (2f), when the value n is sufficiently high, these polymers are copolymers including the unit X and the unit Y.

Each of the units Z6 to Z10 contains one reaction skeleton. The number of repetition (degree of polymerization) of the units Z6 to Z10 in the one-linking polymer in the different mode is not particularly limited if it is 2 or more, but it is preferably a real number of 2 to 100. More preferably, the lower limit value for the number of repetition of the units Z6 to Z10 is 6. In a more preferable mode, the one-linking polymer contains the units Z6 to Z10, with the number of repetition being in the above range, and the end on the —S-A-S— side is bonded to the unit Y.

When the number of repetition of the units Z6 to Z10 is small, it is preferable to suitably select the composition of the non-aqueous solvent contained in the electrolyte, the configuration of the power storage device, the functional groups introduced into each unit, etc. in consideration of the dissolution into the electrolyte. On the other hand, when the number of repetition of the units Z6 to Z10 is large, a power storage device can be configured without any such limitations. When the number of repetition of the units Z6 to Z10 is large, the average molecular weight of the polymer is desirably 10,000 or more. When the reaction skeleton is an EBDT skeleton, the number of repetition of the reaction skeleton in the polymer is desirably approximately 25 or more.

Of the one-linking polymers 2a to 2f, the one-linking polymer 2a, the one-linking polymer 2b, and the one-linking polymer 2d are preferable. Preferable examples of the one-linking polymer 2a include polymers (33) to (37) shown in Table 5 below. The polymers (33) to (35) are trimers of EBDT or derivatives thereof. The polymers (36) to (37) are multimers of EBDT or derivatives thereof. Preferable examples of the one-linking polymer 2b include a polymer (38), which is a trimer of a TTF derivative shown in Table 6 below. Preferable examples of the one-linking polymer 2d include a polymer (39), which is a multimer of a derivative of a condensation product of EBDT and TTF shown in Table 6 below.

TABLE 5

| No. | Chemical structural formula |
|---|---|
| 33 | 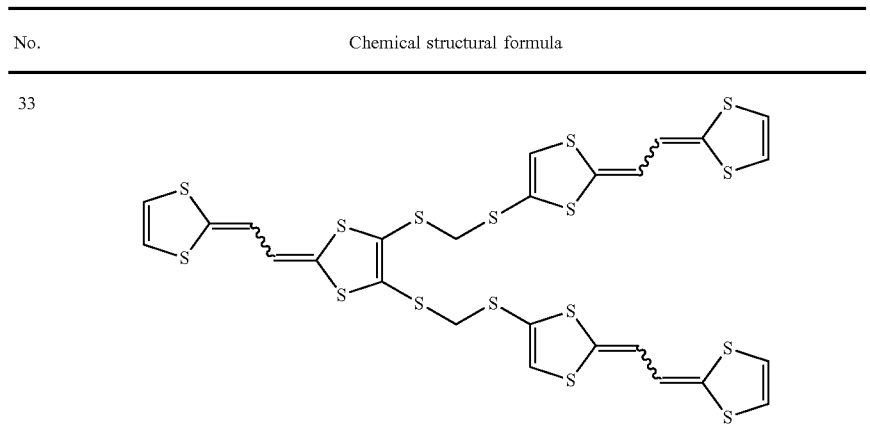 | general formula (2a); A = methylene group, $R_1$ to $R_5$ = hydrogen atom, n = 2

| 34 | 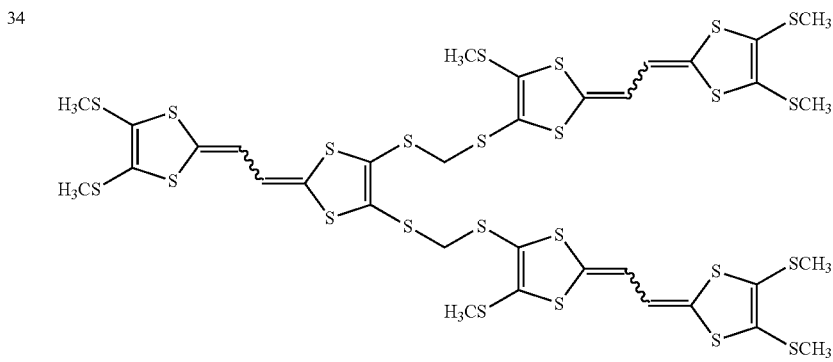 | general formula (2a); A = methylene group, $R_1$ to $R_2$ = hydrogen atom, $R_3$ to $R_5$ = methylthio group, n = 2

TABLE 5-continued

| No. | Chemical structural formula |
|---|---|
| 35 | 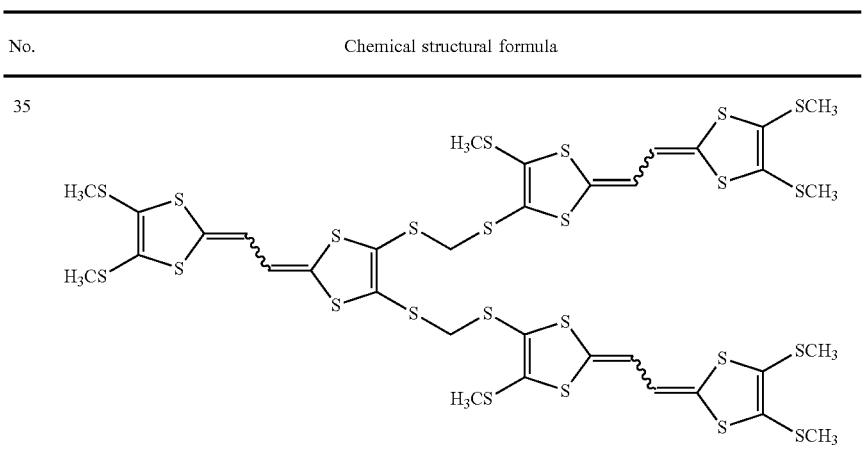 general formula (2a); A = methylene group, $R_1$ to $R_2$ = hydrogen atom, $R_3$ to $R_5$ = methylthio group, n = 2 |
| 36 | 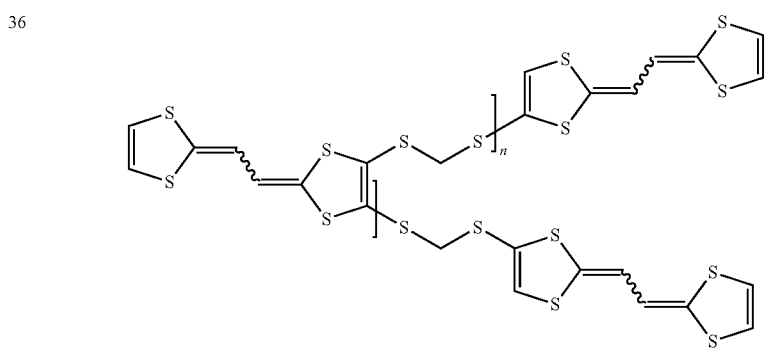 general formula (2a); A = methylene group, $R_1$ to $R_5$ = hydrogen atom, n = real number of 3 or more |
| 37 | 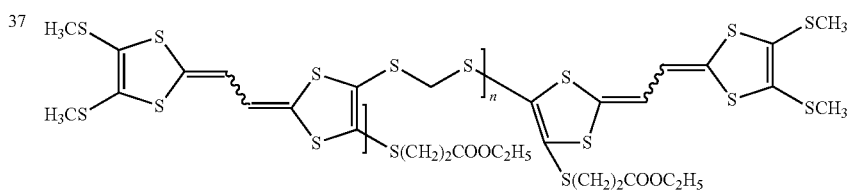 general formula (2a); A = methylene group, $R_1$ to $R_2$ = hydrogen atom, $R_3$ and $R_4$ = methylthio group, $R_5$ = —S(CH$_2$)$_2$COOC$_2$H$_5$, n = real number of 1 or more |

TABLE 6

| No. | Chemical structural formula |
| --- | --- |
| 38 | general formula (2b); A = methylene group, $R_3$ to $R_6$ = methylthio group, n = 2 |
| 39 | general formula (2d); A = methylene group, $R_1$ to $R_2$ = hydrogen atom, $R_3$ to $R_4$ = hexylthio group, n = real number of 1 or more |

The two-linking polymer is preferably a polymer in which at least one selected from the units Z11, Z12, Z13, and Z14 is linked in the form of a chain. Among the two-linking polymers, the two-linking polymer (3) is preferable. Examples of the two-linking polymer (3) include the above-mentioned polymers 3a to 3f. Of the polymers 3a to 3f, polymers in which $R_1$ to $R_6$ are the same functional group are preferable. Of the polymers 3a and 3c to 3e, polymers in which $R_1$ and $R_2$ are a hydrogen atom, a phenyl group, or a phenylthio group are preferable. Also, in the general formulas (3a) to (3f), if the value n is sufficiently high, such two-linking polymers are copolymers of the unit X and the unit Y.

Each of the units Z11 to Z14 contains one reaction skeleton. The number of repetition (degree of polymerization) of the units Z11 to Z14 in the two-linking polymer is not particularly limited if it is 2 or more, but it is preferably a real number of 2 to 100. More preferably, the lower limit value for the number of repetition of the units Z11 to Z14 is 3. In a more preferable mode, the two-linking polymer contains the units Z11 to Z14, with the number of repetition being in the above range, and the end on the —S-A-S— side is bonded to the unit Y.

When the number of repetition of the units Z11 to Z14 is small, it is preferable to suitably select the composition of the non-aqueous solvent contained in the electrolyte, the configuration of the power storage device, the functional groups introduced into each unit, etc. in consideration of the dissolution into the electrolyte. On the other hand, when the number of repetition of the units Z11 to Z14 is large, a power storage device can be configured without any such limitations. When the number of repetition of the units Z11 to Z14 is large, the average molecular weight of the polymer is desirably 10,000 or more. When the reaction skeleton is an EBDT skeleton, the number of repetition of the reaction skeleton in the polymer is desirably approximately 25 or more.

Among the two-linking polymers (3), the polymers 3a to 3d and 3f are preferable. More preferable examples of the two-linking polymer 3a include polymers (40) to (44) shown in Table 7 below. The polymers (40) to (42) are dimers of EBDT derivatives. The polymer (43) is a trimer of an EBDT derivative. The polymer (44) is a multimer of an EBDT derivative.

More preferable examples of the two-linking polymer 3b include polymers (45) to (50), which are a dimer, a trimer, or a multimer of a TTF derivative shown in Table 8 below. More preferable examples of the two-linking polymer 3c include polymers (51), (52), and (56), which are a dimer or a multimer of a derivative of a condensation product of EBDT and TTF shown in Table 9 below. More preferable examples of the two-linking polymer 3d include polymers (53) to (55), which are a dimer of a derivative of a condensation product of EBDT and TTF shown in Table 9 below. More preferable examples of the two-linking polymer 3f include polymers (57) to (61), which are a dimer or a trimer of TTP or a derivative thereof shown in Table 10.

TABLE 7

| No. | Chemical structural formula |
|---|---|
| 40 | general formula (3a); A = methylene group, $R_1$ to $R_2$ = hydrogen atom, $R_3$ to $R_6$ = methylthio group, n = 1 |
| 41 | general formula (3a); A = —$CH_2$—Ph—$CH_2$— where —Ph— is phenylene group, $R_1$ to $R_2$ = hydrogen atom, $R_3$ to $R_6$ = methylthio group, n = 1 |
| 42 | general formula (3a); A = methylene group, $R_1$ to $R_2$: —Ph (phenyl group), $R_3$ to $R_6$: methylthio group, n = 1 |
| 43 | in general formula (3a), A: methylene group, $R_1$ to $R_2$: hydrogen atom, $R_3$ to $R_6$: methylthio group, n = 2 |
| 44 | general formula (3a); A = methylene group, $R_1$ to $R_2$ = hydrogen atom, $R_3$ to $R_6$ = —$S(CH_2)_2COOC_2H_5$, n = real number of 1 or more |

The polymer (42) shown in Table 7 is a polymer containing an EBDT skeleton, and is a derivative of the polymer (40). In the polymer (42), all the carbon atoms forming the carbon-carbon single bond are each substituted with a phenyl group. The addition of the phenyl group makes it possible to control the oxidation reduction potential of the polymer (42) and design a power storage device suitable for the application, performance, or the like. Also, since the benzene ring of the phenyl group can be substituted with various functional groups, the addition of the phenyl group makes it possible to synthesize various derivatives through various synthesis routes. Therefore, the polymer (42) is particularly flexible in material design.

TABLE 8

| No. | Chemical structural formula |
|---|---|
| 45 | general formula (3b); A = methylene group, $R_3$ to $R_6$ = methylthio group, n = 1 |
| 46 | general formula (3b); A = methylene group, $R_3$ to $R_4$, $R_5$ to $R_6$ = joined to form ethylenedithio group, n = 1 |
| 47 | general formula (3b); A = methylene group, $R_3$ to $R_6$ = methylthio group, n = 2 |
| 48 | general formula (3b); A = methylene group, $R_3$ to $R_6$ = methylthio group, n = 3 |
| 49 | general formula (3b); A = —$CH_2$—Ph—$CH_2$— where —Ph— is phenylene group, $R_3$ to $R_6$: methylthio group, n = 2 |
| 50 | general formula (3b); A = methylene group, $R_3$ to $R_6$ = —S(CH$_2$)$_4$COOC$_2$H$_5$, n = real number of 1 or more |

The polymer (46) shown in Table 8 is a polymer containing a TTF skeleton, and a derivative of the polymer (45). In the polymer (46), $R_3$ and $R_4$ at one end of the molecule are joined to form a 1,4-dithia-cyclohexane ring, and $R_5$ and $R_6$ at the other end of the molecule are joined to form a 1,4-dithia-cyclohexane ring. The addition of the 1,4-dithia-cyclohexane ring to each end of the molecule makes it possible to control the dissolution of the polymer (46) into an electrolyte and design a power storage device suitable for the application.

TABLE 9

| No. | Chemical structural formula |
|---|---|
| 51 | 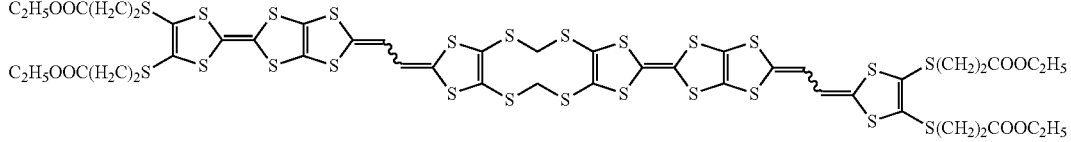<br>general formula (3c); A = methylene group, $R_1$ to $R_2$ = hydrogen atom, $R_3$ to $R_6$ = —S(CH$_2$)$_2$COOC$_2$H$_5$, n = 1 |
| 52 | 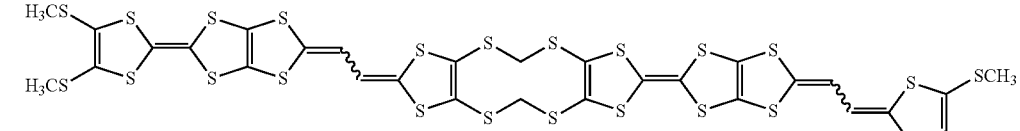<br>general formula (3c); A = methylene group, $R_1$ to $R_2$ = hydrogen atom, $R_3$ to $R_6$ = methylthio group, n = 1 |
| 53 | 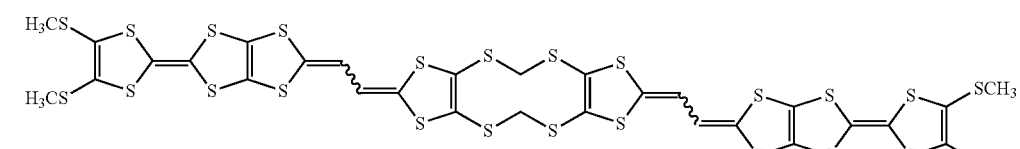<br>general formula (3d); A = methylene group, $R_1$ to $R_2$ = hydrogen atom, $R_3$ to $R_6$ = methylthio group, n = 1 |
| 54 | 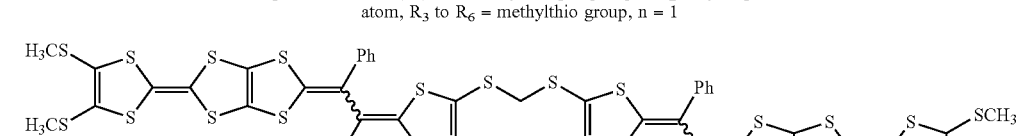<br>general formula (3d); A = methylene group, $R_1$ to $R_2$ = —Ph (phenyl group), $R_3$ to $R_6$ = methylthio group, n = 1 |
| 55 | 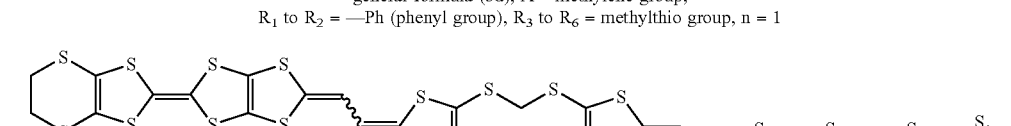<br>general formula (3d); A = methylene group, $R_1$ to $R_2$ = hydrogen atom, $R_3$ to $R_4$, $R_5$ to $R_6$ = joined to form ethylenedithio group, n = 1 |
| 56 | 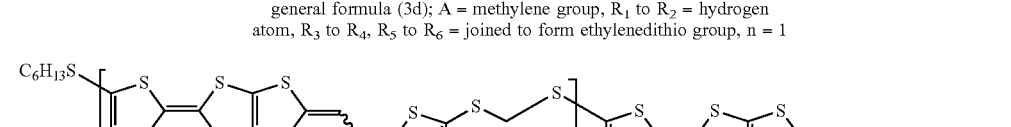<br>general formula (3c); A = methylene group, $R_1$ to $R_2$ = hydrogen atom, $R_3$ to $R_6$ = hexylthio group, n = real number of 1 or more |

The polymer (54) shown in Table 9 is a polymer containing a fused skeleton of EBDT and TTF, and is a derivative of the polymer (53). In the polymer (54), all the carbon atoms forming the carbon-carbon single bond are each substituted with a phenyl group. Thus, similarly to the polymer (42), the use of the polymer (54) makes it easy to control the oxidation reduction potential and design a power storage device suitable for the application, performance, or the like, and hence, the material design becomes particularly flexible. Also, in the polymer (55), since a 1,4-dithiacyclohexane ring is formed at each end of the molecule, it becomes possible to control the dissolution into an electrolyte and design a power storage device suitable for the application, similarly with the polymer (46).

TABLE 10

| No. | Chemical structural formula |
|---|---|
| 57 | *(structure)* general formula (3f); A = methylene group, $R_3$ to $R_6$ = hydrogen atom, n = 1 |
| 58 | *(structure with $H_3CS$ and $SCH_3$ end groups)* general formula (3f); A = methylene group, $R_3$ to $R_6$ = methylthio group, n = 1 |
| 59 | *(structure with $C_6H_{13}S$ and $SC_6H_{13}$ end groups)* general formula (3f); A = methylene group, $R_3$ to $R_6$: hexylthio group, n = 1 |
| 60 | *(structure)* general formula (3f); A = methylene group, $R_3$ to $R_6$: hydrogen atom, n = 2 |
| 61 | *(structure with $H_3CS$ and $SCH_3$ end groups)* general formula (3f); A = methylene group, $R_3$ to $R_6$ = methylthio group, n = 2 |

Preferable examples of the irregularly-linking polymer (4) include a polymer 4a containing a unit Z1 and a unit Z11, a polymer 4b containing a unit Z2 and a unit Z12, a polymer 4c containing a unit Z3 and a unit Z13, and a polymer 4d containing a unit Z4 and a unit Z14. Examples of the polymers 4a to 4d are shown in Table 11 below. In Table 11, the units Z1 to Z4 having one divalent group —S-A-S— where A is as defined above are designated as one-linking units. The units Z11 to Z14 having two divalent groups —S-A-S— where A is as defined above are designated as two-linking units.

In the following general formulae (4a) to (4d), the number of repetition of the one-linking unit and the number of repetition of the two-linking unit are not particularly limited if they are a real number of 1 or more. Each of the one-linking unit and the two-linking unit contains one reaction skeleton. Therefore, the total number of repetition of the units Z1 to Z4 and the units Z11 to Z14 in the polymer is not particularly limited if it is 2 or more. The total number of repetition in the polymer is preferably a real number in the range of 2 to 100. The lower limit value for the total number of repetition is more preferably 3. In a more preferable embodiment, the irregularly-linking polymer (4) contains a one-linking unit and a two-linking unit, with the number of repetition being in the above range, and the end on the —S-A-S— side is bonded to the unit Y.

When the total number of repetition of the one-linking unit and the two-linking unit is small, it is preferable to suitably select the composition of the non-aqueous solvent contained in the electrolyte, the configuration of the power storage device, the functional groups introduced into each unit, etc. in consideration of the dissolution into the electrolyte. On the other hand, when the total number of repetition of the one-linking unit and the two-linking unit is large, a power storage device can be configured without any such limitations. When the total number of repetition is large, the average molecular weight of the polymer is desirably 10,000 or more. When the reaction skeleton is an EBDT skeleton, the number of the reaction skeletons in the polymer is desirably approximately 25 or more.

In the irregularly-linking polymer (4), the contents of the one-linking unit and the two-linking unit are not particularly limited; however, the content of the one-linking unit is preferably 95 mol % to 5 mol %, and more preferably 95 mol % to 50 mol %, while the content of the two-linking unit is preferably 5 mol % to 95 mol %, and more preferably 5 mol % to 50 mol %. That is, desirably, the polymer is composed mainly of the one-linking unit and partially contains the two-linking unit. In this case, the dissolution of the polymer into the non-aqueous solvent can be controlled freely. More specifically, it is possible to prepare a polymer that is, for example, insoluble into the non-aqueous solvent contained in the electrolyte of a power storage device and is soluble into the organic solvent used for synthesis and purification. Thus, a highly pure polymer with good cycle characteristics can be prepared easily.

TABLE 11
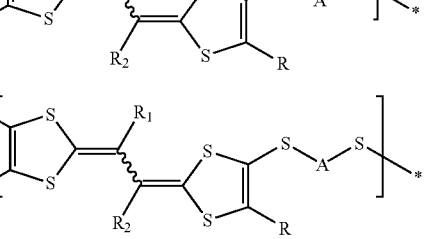

TABLE 11-continued

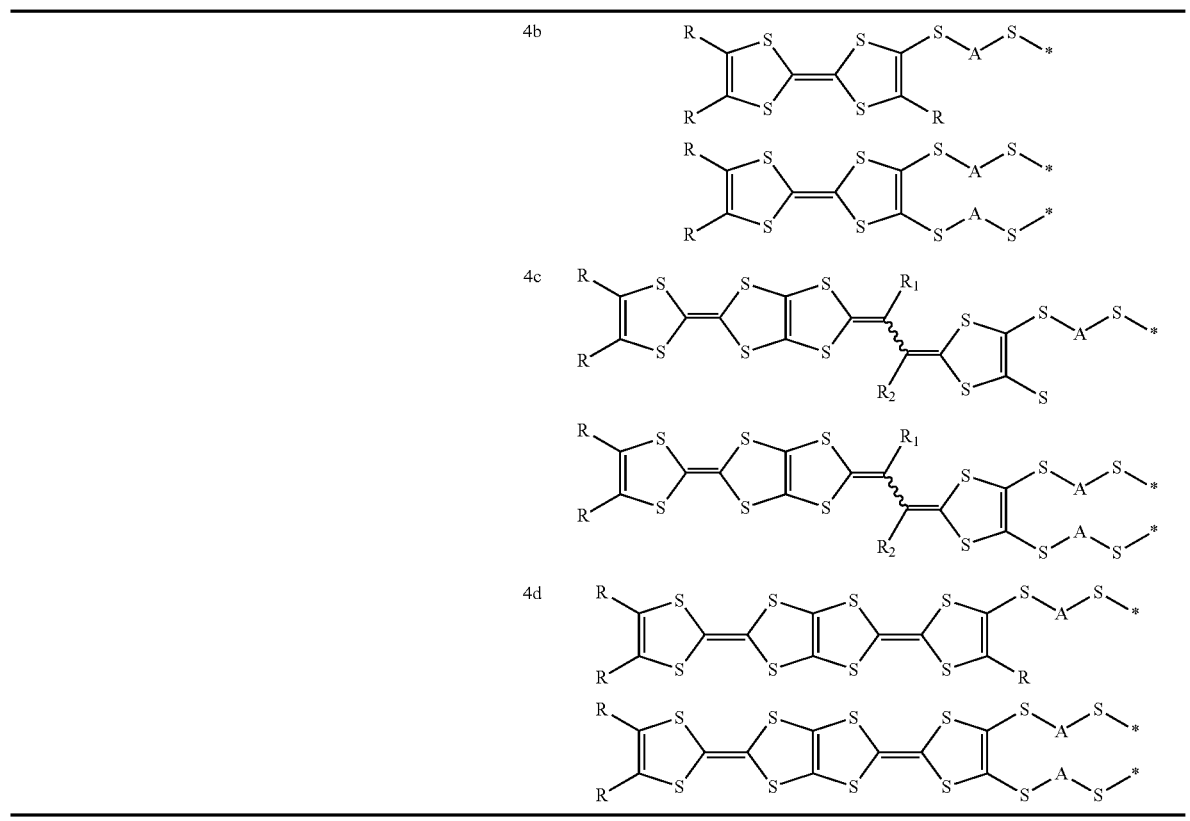

In the formulae (4a) to (4d), A, $R_1$, $R_2$, and R are as defined above.

As described above, the polymers of the invention having reaction skeletons linked by divalent groups —S-A-S where A is as defined above allow synthesis of a large number of derivatives. Among them, polymers having EBDT skeletons or fused skeletons of EBDT and TTF linked by divalent groups —S-A-S where A is as defined above allow synthesis of a larger number of derivatives. This is because the EBDT skeleton has a carbon-carbon single bond in the molecule, and hydrogen atoms bonded to the carbon atoms forming the carbon-carbon single bond can be substituted with other functional groups.

Also, the respective polymers shown above have a 1,3-dithiol ring at the end of the molecule. Hydrogen atoms bonded to two carbon atoms forming the carbon-to-carbon unsaturated bond in the 1,3-dithiol ring can be substituted with various functional groups such as a methylthio group. In this manner, by suitably selecting an electron donating group, an electron withdrawing group, or the like as a functional group substituted on the 1,3-dithiol ring, it becomes possible to control oxidation reduction potential. As a result, an electrode active material suitable for the application, specifications, etc. of a power storage device can be designed.

Further, in the general formulae (1a) to (1f), (2a) to (2f), and (3a) to (3f), n represents the number of repetition (degree of polymerization) in each polymer, as mentioned above. As the number of repetition increases, the polymers of the invention are more resistant to dissolution in an electrolyte. Therefore, when the polymers of the invention are used as electrode active materials, as the number of repetition increases, the dissolution into an electrolyte is suppressed more effectively, and good cycle characteristics and storage characteristics are obtained. As a result, the design flexibility of the power storage device increases.

When the number of repetition is small, the composition of the solvent of the electrolyte, the configuration of the power storage device, the functional groups introduced into the polymer of the invention, etc. are limited in consideration of dissolution into the electrolyte. However, the polymers of the invention represented by the general formulae (1a) to (1f), (2a) to (2f), and (3a) to (3f) where the number n of repetition is a real number of 1 or more are highly resistant to dissolution into the electrolyte. Thus, they can be advantageously used as electrode active materials even when the degree of polymerization is small, i.e., when the molecular weight is not large.

The polymers included in the electrode active materials of the invention can be prepared by simple synthesis methods that do not require an expensive metal catalyst or a special environment such as an ultra-low temperature range. Various synthesis methods shown below are easy for scale up and suited for industrial mass production.

The one-linking polymers can be synthesized by carrying out at least one reaction selected from the group consisting of, for example, the coupling reaction represented by the following reaction formula 1, the Witting reaction represented by the following reaction formula 2, and the coupling reaction represented by the following reaction formula 3. These reactions can be carried out repeatedly, if necessary. The reactions of the reaction formulae 1 and 2 allow synthesis of polymers containing an EBDT skeleton. The reaction of the reaction formula 2 is a synthesis method for forming a carbon-carbon double bond from aldehyde or ketone. The reaction formula 3 allows synthesis of a polymer containing a fused skeleton of EBDT and TTF.

[Chem. 13]

Reaction formula 1

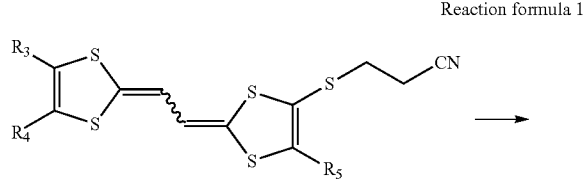

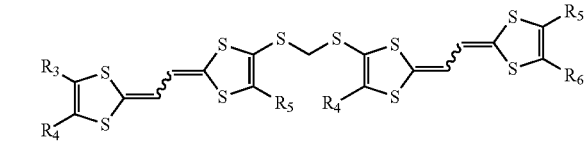

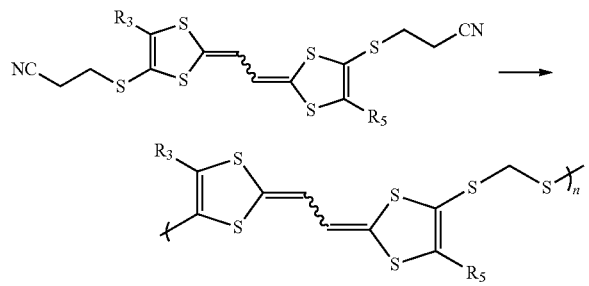

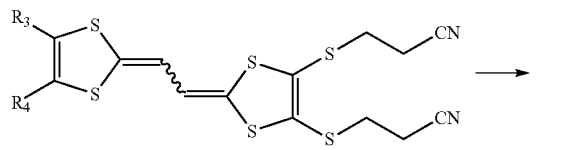

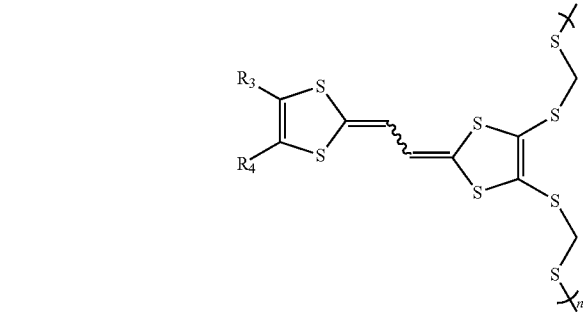

[Chem. 14]

Reaction formula 2

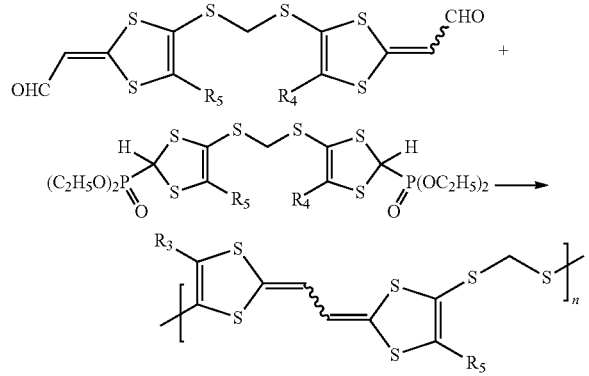

Reaction formula 3

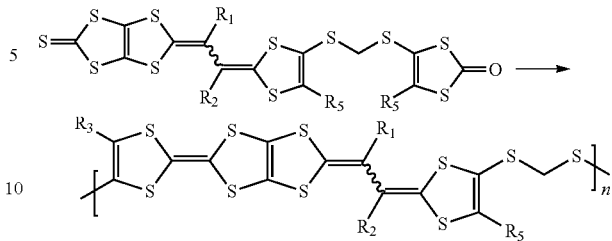

In the reaction formulae 1 to 3, $R_1$ to $R_6$ and n are as defined above.

In the polymers prepared through the reaction formulae 1 to 3, $R_3$ or $R_5$ at the end may not be a monovalent aliphatic group or a monovalent aromatic group. For example, the end group may be a cyano group or the like in the reaction formula 1, may be a tertiary phosphine group such as a triethylphosphine oxide group, an aldehyde group, or the like in the reaction formula 2, or may be a carboxyl group, a ketone group, a thione group, or the like in the reaction formula 3. A polymer having such an end group may be used as it is as the polymer of the invention. Alternatively, such an end group may be substituted with a monovalent aliphatic group or a monovalent aromatic group by a known method.

The two-linking polymers can be synthesized by carrying out at least one reaction selected from the group consisting of, for example, the coupling reaction represented by the following reaction formula 4, the coupling reaction represented by the following reaction formula 5, and the Witting reaction represented by the following reaction formula 6. These reactions can be carried out repeatedly, if necessary. The reactions of the reaction formulae 4 and 5 allow synthesis of polymers containing a TTF skeleton. The reaction of the reaction formula 6 allows synthesis of a polymer containing an EBDT skeleton.

[Chem. 15]

Reaction formula 4

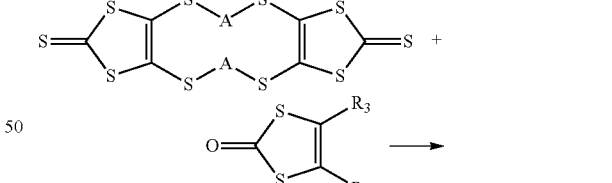

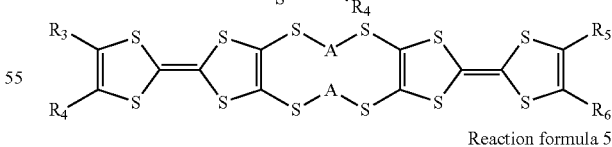

Reaction formula 5

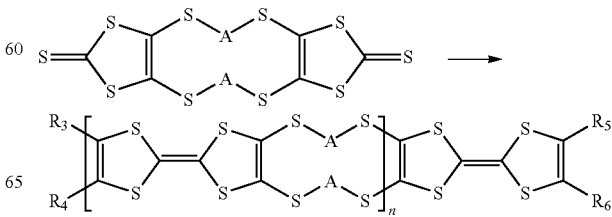

-continued

Reaction formula 6

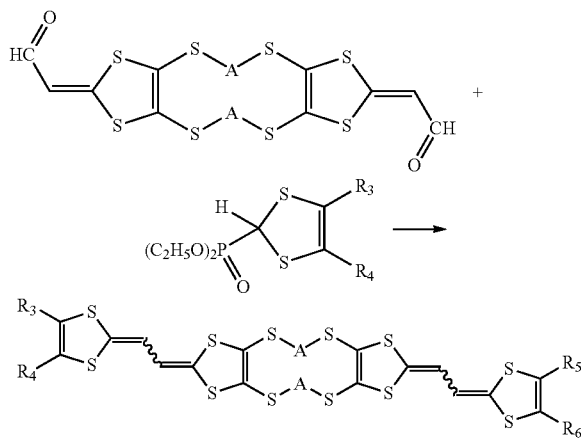

In the reaction formulae 4 to 6, A, $R_3$ to $R_6$, and n are as defined above.

In the polymers prepared through the reaction formulae 4 to 6, the end group may not be a monovalent aliphatic group or a monovalent aromatic group. For example, the end group may be a carbonyl group, a thione group, or the like in the reaction formula 4, may be a thione group or the like in the reaction formula 5, or may be a tertiary phosphine group such as a triethylphosphine oxide group, an aldehyde group, or the like in the reaction formula 6. A polymer having such an end group may be used as it is as the polymer of the invention. Alternatively, such an end group may be substituted with a monovalent aliphatic group or a monovalent aromatic group by a known method.

Further, using the same raw material compound and the same reaction, a one-linking polymer, a two-linking polymer, and an irregularly-linking polymer can be synthesized, for example, through the reaction represented by the reaction formula 7.

groups —S-A-S. Such a polymer has a molecular weight corresponding to that of a high polymer even when it is, for example, a two-linking polymer of a TTF derivative.

The reaction mechanism of the reaction formula 7 is as follows. In the substituents (Rs, Rt, Rv, and Rw) of the TTF derivative, the moiety other than the sulfur atom directly bonded to the carbon atom in the TTF derivative functions as a blocking group for the sulfur atom. When the TTF derivative is reacted with an alkali, a deprotection reaction occurs, so that the moiety other than the sulfur atom is removed from the substituents of the TTF derivative. As a result, a TTF derivative having a thiolate ion is produced. At the same time, the dihalogen compound is dehalogenated by the alkali, so that it becomes -A-. The thiolate ion and -A- are bonded to form a polymer included in the electrode active material of the invention.

In the reaction of the reaction formula 7, by controlling the amounts of the alkali and the dihalogen compound added and the like, it is possible to prepare an intended one of a one-linking polymer, a two-linking polymer, and an irregularly-linking polymer. Specifically, to synthesize a one-linking polymer, it is desirable to set the amount of the alkali to approximately 1 equivalent relative to the TTF derivative, and set the amount of the dihalogen compound to approximately 1 to 2 equivalents relative to the TTF derivative. When the TTF derivative is reacted with one equivalent of the alkali, about two of the four substituents of the TTF derivative undergo a deprotection reaction to produce a TTF derivative having two thiolate ions. In this manner, a one-linking polymer can be prepared.

Also, to synthesize a two-linking polymer, it is desirable to set the amount of the alkali to an excessive amount of 2 equivalents or more relative to the TTF derivative, and set the amount of the dihalogen compound to approximately 2 to 4 equivalents relative to the TTF derivative. When the TTF derivative is reacted with not less than 2 equivalents of the alkali, the four substituents of the TTF derivative undergo a deprotection reaction to produce a TTF derivative having four thiolate ions. In this manner, a two-linking

[Chem. 16]

Reaction formula 7

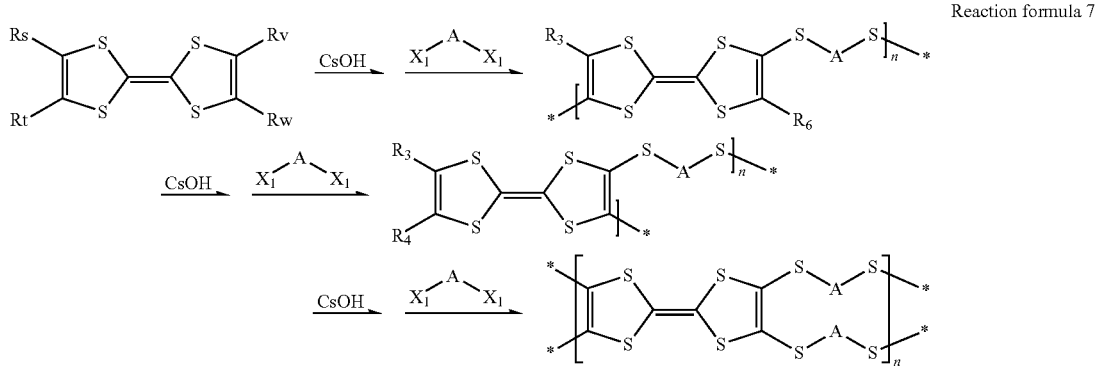

In the reaction formula 7, A, $R_3$, $R_4$, $R_5$, and n are as defined above. Rs, Rt, Rv, and Rw each independently represent —$SC_2H_4COOCH_3$, —$SC_2H_4COOC_2H_5$, or —$SC_2H_4CN$. $X_1$ represents a halogen atom.

In the reaction formula 7, in the presence of an alkali (CsOH), a TTF derivative and a dihalogen compound ($X_1$-A-$X_1$) such as a dihalogen alkane are reacted to synthesize a polymer in which the TTF derivative is linked by divalent polymer can be prepared. Also, an irregularly-linking polymer can be prepared by selecting the amounts of the alkali and the dihalogen compound between the amounts used to synthesize a one-linking polymer and the amounts used to synthesize a two-linking polymer.

After the synthesis of a one-linking polymer or an irregularly-linking polymer, the substituents (Rs, Rt, Rv, and Rw) may remain bonded to the TTF skeleton contained in the polymer. In this case, the substituents can be converted to unreactive sites by alkylthiolation or the like. Also, by changing part of the dihalogen compound to a monohalogen compound, it is possible to facilitate alkylthiolation and control polymerization reaction to produce a polymer having a desired number of repetition. In terms of preparing an intended one of a one-linking polymer, a two-linking polymer, and an irregularly-linking polymer from the same starting material by only a synthesis method, the substituents $R_3$, $R_4$, $R_6$ of the polymers as the synthesized products of the reaction formula 7 are desirably sulfur-containing aliphatic groups. Further, they are desirably thioalkyl groups. In this embodiment, a TTF derivative was used as an example to describe the synthesis method. However, instead of the TTF derivative, EBDT or a derivative thereof, a condensation product of EBDT and TTF or a derivative thereof, or TTP or a derivative thereof may be used to synthesize a polymer having an EBDT skeleton, a fused skeleton of EBDT and TTF, or a TTP skeleton in the same manner as described above.

To synthesize a polymer having a different structure, it is common to use a different raw material compound or a different reagent under a different reaction condition for synthesis. Contrary to this, in the case of synthesizing a polymer contained in the electrode active material of the invention, the same raw material compound and reagent can be used to synthesize a one-linking polymer, a two-linking polymer, or an irregularly-linking polymer merely by changing the ratio of these materials used.

Also, to synthesize a polymer according to the invention, the reaction skeleton is selected from a TTF skeleton, an EBDT skeleton, a fused skeleton of EBDT and TTF, and a TTP skeleton, and the linking structure is selected from a one-linking structure, a two-linking structure, and an irregularly-linking structure. Therefore, many kinds of polymers which can be used as electrode active materials can be synthesized. As such, an electrode active material suitable for designing a power storage device can be readily prepared.

Specifically, to suppress dissolution into an electrolyte and enhance reliability as an electrode active material, for example, a two-linking polymer or a polymer having a large number of repetition of a reaction skeleton can be designed. To heighten energy density, for example, a polymer having a TTF skeleton or a fused skeleton of EBDT and TTF can be designed. To heighten the output of a power storage device, for example, a polymer containing a TTF skeleton or an EBDT skeleton can be designed.

When a polymer of the invention is synthesized, the synthesized polymer may be a mixture of a plurality of polymers having different numbers of repetition. In this case, the average number of repetition may be a decimal fraction.

[Power Storage Device]

The power storage device of the invention is characterized in that at least one of the positive electrode and the negative electrode uses the above-described electrode active material of the invention. For example, one of the positive electrode and the negative electrode uses the electrode active material of the invention, while the other electrode uses a conventional electrode active material used in a conventional power storage device. Of course, each of the positive electrode and the negative electrode may use the electrode active material of the invention. It is preferable to use the electrode active material of the invention as a positive electrode active material.

The power storage device of the invention includes, for example, a positive electrode, a negative electrode, a separator, and an electrolyte. The positive electrode and the negative electrode are disposed so as to face each other, with the separator interposed therebetween.

The positive electrode includes a positive electrode current collector and a positive electrode active material layer, and the positive electrode active material layer is disposed on the separator side. The positive electrode current collector is not particularly limited, and can be, for example, a porous sheet or non-porous sheet comprising a metal material, such as nickel, aluminum, gold, silver, copper, stainless steel, an aluminum alloy, or a copper alloy. Examples of the porous sheet include mesh, woven fabric, and non-woven fabric. An example of the non-porous sheet includes metal foil.

A carbon material such as carbon may be applied to the surface of the positive electrode current collector. This allows the positive electrode active material layer and the positive electrode current collector to be bonded chemically or physically. As a result, for example, the resistance value of the positive electrode decreases, the carbon material produces a catalytic effect, and the bond between the positive electrode active material layer and the positive electrode current collector is strengthened.

The positive electrode active material layer is provided on at least one surface of the positive electrode current collector. It includes a positive electrode active material and, if necessary, contains an electron conductive agent, an ion conductive agent, a binder, etc. When the electrode active material of the invention is used as the positive electrode active material, the preferable negative electrode active material is, for example, a graphite material such as natural graphite or artificial graphite; an amorphous carbon material such as graphitized carbon (graphite) or activated carbon; lithium metal; a lithium-containing composite nitride; a lithium-containing titanium oxide; a silicon material such as silicon, a silicon oxide, or a silicon alloy; a tin material such as tin, a tin oxide, or a tin alloy.

The electron conductive agent and the ion conductive agent decrease, for example, the resistance of the electrode. Examples of the electron conductive agent include, but are not limited to, carbon materials such as carbon black, graphite, and acetylene black, and conductive polymer compounds such as polyaniline, polypyrrole, and polythiophene. Examples of the ion conductive agent include, but are not limited to, solid electrolytes such as polyethylene oxide and gel electrolytes such as polymethyl methacrylate.

The binder increases, for example, the adhesion of the constituent materials of the electrode. Examples of the binder include, but are not limited to, polyvinylidene fluoride, vinylidene fluoride-hexafluoropropylene copolymers, vinylidene fluoride-tetrafluoroethylene copolymers, polytetrafluoroethylene, styrene-butadiene copolymer rubber, polypropylene, polyethylene, and polyimide.

The positive electrode active material layer can be formed, for example, by mixing a positive electrode active material, an electron conductive agent, an ion conductive agent, a binder, etc., and pressing the resulting mixture onto a positive electrode current collector. Also, the positive electrode active material layer can be formed by mixing the above-mentioned materials with a dispersion medium to prepare a positive electrode mixture slurry, applying the positive electrode mixture slurry onto a surface of a positive electrode current collector, drying the resulting coating, and rolling it. The dispersion medium contained in the positive electrode mixture slurry is the same as the dispersion medium contained in the negative electrode mixture slurry. Also, when the positive electrode active material includes the above-mentioned polymer and an organic solvent capable of dissolving the polymer is present, an electron conductive agent, an ion conductive agent, a binder, etc. may be dissolved in the organic solvent solution of the positive electrode active material to prepare a positive electrode mixture slurry. By using such a positive electrode mixture slurry to form a positive electrode active material layer, an electrode with a high energy density can be produced with high efficiency.

The negative electrode includes a negative electrode current collector and a negative electrode active material layer, and the negative electrode active material layer is disposed on the separator side. The negative electrode current collector can be a porous sheet or non-porous sheet comprising the same metal material as that used for the positive electrode current collector. A carbon material such as carbon may also be applied to a surface of the negative electrode current collector to decrease the resistance value, produce a catalytic effect, and strengthen the bond between the negative electrode active material layer and the negative electrode current collector.

The negative electrode active material layer is provided on at least one surface of the negative electrode current collector. It includes a negative electrode active material and, if necessary, contains an electron conductive agent, an ion conductive agent, a binder, etc. When the electrode active material of the invention is used as the negative electrode active material, the positive electrode active material is not particularly limited, but preferable examples include lithium-containing composite metal oxides such as $LiCoO_2$, $LiNiO_2$, and $LiMn_2O_4$, and olivine-type lithium phosphate. The electron conductive agent, the ion conductive agent, and the binder are the same as the electron conductive agent, ion conductive agent, and binder contained in the positive electrode active material layer.

The negative electrode active material layer can be formed, for example, by applying a negative electrode mixture slurry on a surface of the negative electrode current collector, drying the resulting coating, and rolling it. The negative electrode mixture slurry can be prepared by mixing a negative electrode active material and, if necessary, an electron conductive agent, an ion conductive agent, a binder, a thickener, etc., with a dispersion medium. Examples of the dispersion medium include dimethylformamide, dimethyl acetamide, methyl formamide, N-methyl-2-pyrrolidone, dimethyl amine, acetone, cyclohexanone, and water.

Without using any dispersion medium, the negative electrode active material layer can be formed by mixing a negative electrode active material and, if necessary, an electron conductive agent, an ion conductive agent, a binder, etc. and pressing the resulting mixture to a negative electrode current collector. Also, when a silicon material or tin material is used as the negative electrode active material, the negative electrode active material layer can be formed by vacuum deposition, sputtering, or the like. Further, the negative electrode may be a laminate of a lithium metal plate and a negative electrode current collector.

The separator is disposed between the positive electrode and the negative electrode. The separator can be a porous sheet having predetermined ion permeability, mechanical strength, an insulating property, and the like. Examples of the porous sheet include a micro-porous film, woven fabric, and non-woven fabric. Various resin materials can be used as the material for the separator; in consideration of durability, shut down function, battery safety, etc., polyolefins such as polyethylene and polypropylene are preferable.

The electrolyte is typically a liquid electrolyte with which the separator is to be impregnated. The liquid electrolyte includes a non-aqueous solvent and a supporting salt capable of dissolving in the non-aqueous solvent. The supporting salt is composed of a cation and an anion. Examples of the cation include cations of alkali metals such as lithium, sodium, and potassium, cations of alkaline earth metals such as magnesium, and quaternary ammonium cations such as tetraethyl ammonium and 1,3-ethyl methyl imidazolium. These cations can be used singly or in combination. Among them, the lithium cation and quaternary ammonium cations are preferable, and the lithium cation (lithium ion) is more preferable.

Examples of the anion include a halide anion, a perchlorate anion, a trifluoromethylsulfonate anion, a tetrafluoroborate anion, a trifluorohexafluorophosphate anion, a bis(trifluoromethylsulfonyl)imide anion, and a bis(perfluoroethylsulfonyl)imide anion. These anions can be used singly or in combination.

Examples of the supporting salt include lithium chloride, lithium perchlorate, lithium trifluoromethylsulfonate, lithium tetrafluoroborate, lithium hexafluorophosphate, lithium bistrifluoromethylsulfonyl imide, lithium thiocyanate, magnesium perchlorate, magnesium trifluoromethylsulfonate, and sodium tetrafluoroborate ($NaBF_4$). These supporting salts can be used singly or in combination.

In order to cause an electrochemical reaction in the power storage device, for example, the supporting salt needs to be dissolved in a non-aqueous solvent such that it is dissociated into a cation and an anion. Thus, the non-aqueous solvent needs to have a high dielectric constant. Also, some of the electrode active materials of the invention easily dissolve in a non-aqueous solvent with a high dielectric constant. Therefore, in the power storage device of the invention, it is preferable to use a non-aqueous solvent with a suitable dielectric constant for the electrolyte.

In this respect, the non-aqueous solvent is preferably a non-aqueous solvent with a dielectric constant of 10 to 30. As the non-aqueous solvent with a dielectric constant of 10 to 30, a non-aqueous solvent having a dielectric constant in this range may be used as it is. It is also possible to mix a plurality of non-aqueous solvents with different dielectric constants to adjust the dielectric constant of the resulting solvent mixture in this range. Preferably, a non-aqueous solvent with a dielectric constant of 10 or less and a non-aqueous solvent with a dielectric constant of 30 or more are mixed to form a non-aqueous solvent having a dielectric constant in the above range.

If the dielectric constant of the non-aqueous solvent is significantly lower than 10, the dissolution of the supporting salt in the non-aqueous solvent may lower and the electrochemical oxidation-reduction reaction may not proceed smoothly. To cause an electrochemical oxidation-reduction reaction in a power storage device using a liquid electrolyte, the non-aqueous solvent needs to dissolve the supporting salt so that the cation and anion of the supporting salt can be reversibly bonded and dissociated. If the dielectric constant of the non-aqueous solvent is significantly higher than 30, the electrode active material of the invention may dissolve in the non-aqueous solvent. Although the electrode active material of the invention is derivatized, it may dissolve in a non-aqueous solvent having a dielectric constant of significantly higher than 30 so that it may decrease the performance of the power storage device.

Examples of the solvent with a dielectric constant of 10 or less include chain carbonic acid esters, chain carboxylic acid esters, and chain ethers. Among them, one or more can be used. Examples of the solvent with a dielectric constant of 30 or more include cyclic carbonic acid esters and cyclic ethers. Among them, one or more can be used.

Examples of chain carbonic acid esters include dimethyl carbonate, diethyl carbonate, n-propyl carbonate, dibutyl carbonate, diisopropyl carbonate, and methyl ethyl carbonate. Examples of chain carboxylic acid esters include methyl formate, ethyl formate, methyl acetate, ethyl acetate, propyl acetate, methyl propionate, methyl butyrate, and methyl valerate. Examples of chain ethers include 1,2-dimethoxyethane, 1,2-diethoxyethane, diethyl ether, dimethyl ether, methyl ethyl ether, and dipropyl ether.

Examples of cyclic carbonic acid esters include propylene carbonate and ethylene carbonate. Examples of cyclic ethers include tetrahydrofuran, 2-methyltetrahydrofuran, 1,4-dioxane, 1,3-dioxolane, 3-methyl-1,3-dioxolane, and 2-methyl-1,3-dioxolane.

A solid electrolyte or a gel polymer electrolyte may also be used as the electrolyte.

Examples of solid electrolytes include $Li_2S$—$SiS_2$—lithium compound (the lithium compound is at least one selected from $Li_3PO_4$, LiI, and $Li_4SiO_4$), $Li_2S$—$P_2O_5$, $Li_2S$—$B_2S_5$, $Li_2S$—$B_2S_5$, $Li_2S$—$P_2S_5$—$GeS_2$, sodium/alumina ($Al_2O_3$), amorphous polyethers with a low phase transition temperature (Tg), amorphous vinylidene fluoride copolymers, blends of different polymers, and polyethylene oxide.

The gel polymer electrolyte can be one prepared by gelling a liquid electrolyte by using a polymer. The liquid electrolyte preferably contains a non-aqueous solvent of a low molecular weight such as ethylene carbonate or propylene carbonate. The polymer can be, for example, polyacrylonitrile, a copolymer of ethylene and acrylonitrile, a crosslinked polymer thereof.

The power storage device of the invention is an apparatus capable of storing electrical energy produced by an electrochemical oxidation-reduction reaction. Examples of the power storage device include primary batteries, secondary batteries, electrochemical capacitors, electrolytic capacitors, sensors, and electrochromic devices.

[Electronic and Transportation Devices]

The electronic device of the invention has the same configuration as conventional electronic devices except that it uses the power storage device of the invention as the power source. Also, the transportation device of the invention has the same configuration as conventional transportation devices except that it uses the power storage device of the invention as the power source. When the power storage device of the invention is used as the power source of an electronic device or a transportation device, the power storage device of the invention is preferably a secondary battery. Further, the electronic device and transportation device of the invention may have a power source other than the power storage device of the invention.

EXAMPLES

The invention is hereinafter described specifically by way of Examples, Comparative Examples, and Test Examples.

Example 1

A coin-shaped power storage device 1 illustrated in FIG. 1 was produced as a power storage device of this embodiment. FIG. 1 is a longitudinal sectional view schematically showing the structure of the coin-shaped power storage device 1 in an embodiment of the invention.

(1) Preparation of Positive Electrode Active Material

A one-linking polymer (11) was synthesized by the following synthesis process.

[Chem. 17]

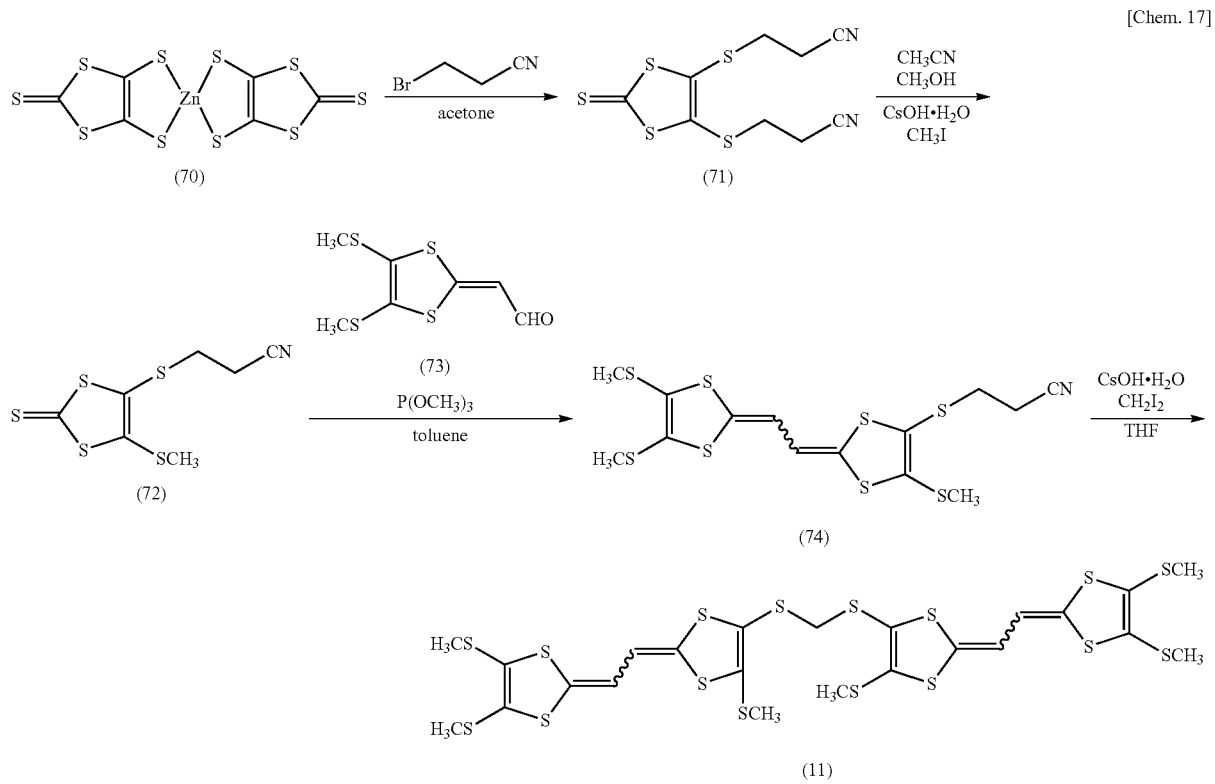

Synthesis of Compound (71)

36 g of a compound (70) was introduced into a 1-liter two-necked eggplant flask, and the atmosphere inside the eggplant flask was replaced with argon. Subsequently, 440 ml of acetone and 17 ml of 3-bromopropionitrile were added, stirred at 70° C. for 5 hours, and stirred at room temperature all night. The resulting reaction mixture was filtered through celite, and the resulting filtrate was concentrated by an evaporator and separated by column chromatography (silica gel, methylene chloride). After removal of the solvent by the evaporator, it was vacuum dried to give 28.1 g of a compound (71). The yield was 92.5%.

Synthesis of Compound (72)

20.0 g of the compound (71) was introduced into a 500-ml two-necked eggplant flask, and the atmosphere inside the eggplant flask was replaced with argon. Subsequently, 250 ml of tetrahydrofuran was added, and a solution of 11.0 g of cesium hydroxide monohydrate in 100 ml of methanol was added, followed by stirring at room temperature for 30 minutes. Then, 20.5 ml of iodomethane and 100 ml of acetonitrile were added, followed by stirring for 2 hours. The resulting reaction mixture was extracted with water and methylene chloride, washed, and dehydrated and dried with sodium sulfate. Thereafter, it was concentrated by an evaporator and reprecipitated by using methanol. The resulting solid was washed and vacuum dried to give 14.66 g of a compound (72). The yield was 84.1%.

Synthesis of Compound (74)

1.69 g of the compound (72) and 1.0 g of a compound (73) were introduced into a 200-ml two-necked eggplant flask, followed by argon replacement. 40 ml of dry toluene and 40 ml of dry trimethyl phosphite were added and stirred at 110° C. for 2 hours. Upon completion of the reaction, the resulting reaction mixture was concentrated by an evaporator and separated by column chromatography (silica gel, methylene chloride). This was concentrated by the evaporator and reprecipitated by using hexane. The resulting solid was washed and vacuum dried to give 1.61 g of a compound (74). The yield was 83.7%.

[Synthesis of One-Linking Polymer (11)]

1.0 g of the compound (74) and 80 ml of dry tetrahydrofuran were introduced into a 300-ml eggplant flask, and a solution of 0.45 g of cesium hydroxide monohydrate in 40 ml of methanol was added, followed by stirring at room temperature for 30 minutes. Then, 1.8 ml of diiodomethane was added, followed by stirring for 2 hours. The resulting reaction mixture was extracted with water and methylene chloride, washed with water, and filtered. The resulting filtrate was concentrated by an evaporator and reprecipitated by using hexane. The resulting solid was washed and dried to give 0.58 g of a yellow solid one-linking polymer (11). An NMR analysis (hereinafter referred to as "NMR") confirmed the presence of the one-linking polymer (11). The yield was 64.7%.

$^1$H NMR (270 MHz, CDCl$_3$) δ=5.75 (t, J=1.0 Hz, 4H), 4.12 (d, J=1.6 Hz, 2H), 2.39 to 2.45 (18H, m).

(2) Production of Power Storage Device

The one-linking polymer (11) thus obtained was crushed in a mortar. The particle size of the crushed one-linking polymer (11) was approximately 10 μm. This was used as a positive electrode active material. A positive electrode mixture was prepared by homogeneously mixing 12.5 mg of the one-linking polymer (11) and 100 mg of acetylene black (conductive agent) and further mixing 25 mg of polytetrafluoroethylene (binder).

This positive electrode mixture was pressed onto a positive electrode current collector 12 comprising an aluminum mesh and vacuum dried to form a positive electrode active material layer 13 on the positive electrode current collector 12. This was punched out into a 13.5-mm diameter disc to produce a positive electrode 21. The weight of the positive electrode active material applied was 1.5 mg/cm$^2$ per unit area of the positive electrode 21.

A lithium metal plate (thickness 300 μm) was punched out into a 15-mm diameter disc as a negative electrode active material layer 16, and this was laminated on a stainless steel negative electrode current collector 17 in the form of a 15-mm diameter disc, to produce a negative electrode 22.

An electrolyte was prepared by dissolving lithium tetrafluoroborate (LiBF$_4$) as a supporting salt at a concentration of 1 mol/L in a solvent mixture of ethylene carbonate and diethyl carbonate (volume ratio 1:5, dielectric constant: 18).

The positive electrode 21 was disposed on a case 11 so that the positive electrode current collector 12 was in contact with the inner face of the case 11. A separator 14 comprising a porous polyethylene sheet was disposed on the positive electrode 21. The electrolyte prepared in the above manner was injected into the case 11. The negative electrode 22 was pressed to the inner face of a seal plate 15, and a resin seal ring 18 was fitted to the circumference of the seal plate 15. The seal plate 15 was fitted to the opening of the case 11 so that the positive electrode 21 faced the negative electrode 22 with the separator 14 interposed therebetween. Using a press, the open edge of the case 11 was crimped onto the circumference of the seal plate 15 with the seal ring 18 interposed therebetween, to seal the case 11 with the seal plate 15. In this manner, a coin-shaped power storage device 1 was produced.

Example 2

(1) Preparation of Positive Electrode Active Material

A one-linking polymer (12) was synthesized by the following synthesis process.

[Chem. 18]

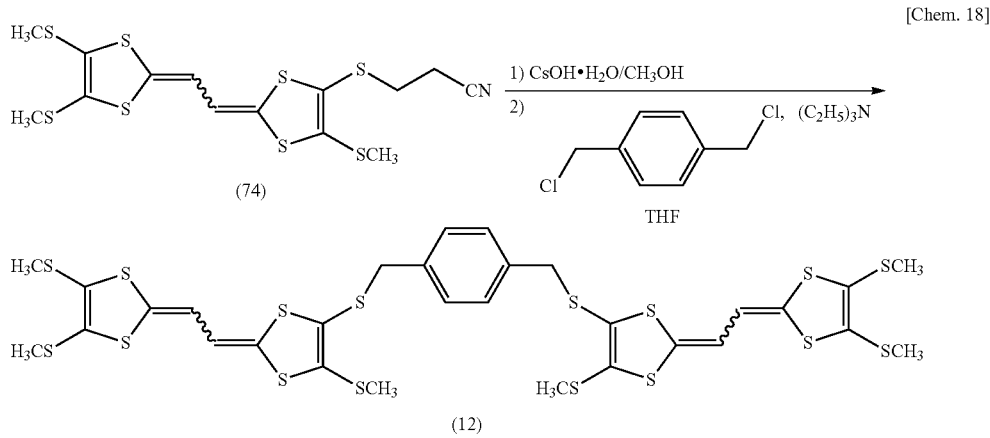

[Synthesis of One-Linking Polymer (12)]

The one-linking polymer (12) was synthesized in the same manner as in Example 1, except that in the synthesis process of the one-linking polymer (11) of Example 1, diiodomethane was replaced with the same equivalents of 1,4-bischloromethylbenzene and that 3 ml of triethylamine was further used. An NMR and an elemental analysis confirmed the presence of the one-linking polymer (12).

$^1$H NMR (270 MHz, CDCl$_3$) δ=2.80, 4.60, 6.26, 6.32, 7.79

Elemental analysis: C: 40.73, H: 3.56

(2) Production of Power Storage Device

A coin-shaped power storage device was produced in the same manner as in Example 1 except for the use of the one-linking polymer (12).

Example 3

(1) Preparation of Positive Electrode Active Material

A one-linking polymer (13) was synthesized by the following synthesis process.

[Chem. 19]

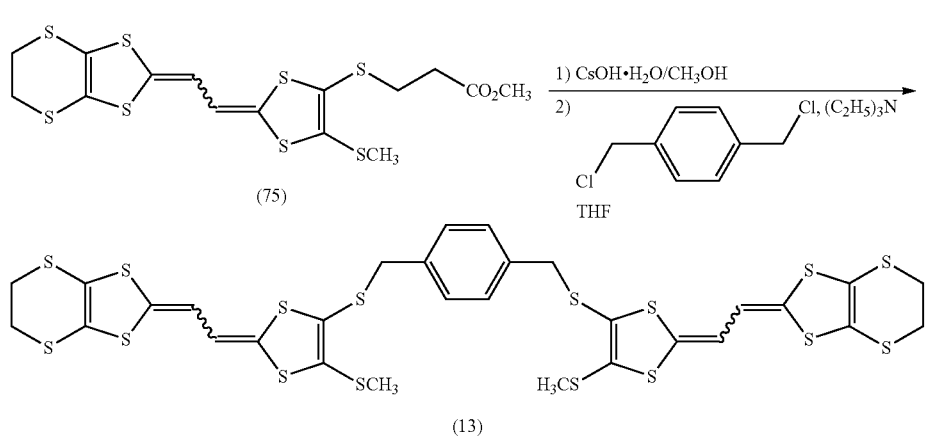

(75)

(13)

[Synthesis of One-Linking Polymer (13)]

The one-linking polymer (13) was synthesized in the same manner as in Example 2, except that in the synthesis process of the one-linking polymer (12) of Example 2, the compound (74) was replaced with a compound (75). An NMR and an elemental analysis (S) confirmed the presence of the one-linking polymer (13).

$^1$H-NMR (270 Hz, CDCl$_3$) δ=2.80, 4.60, 6.26, 6.32, 7.79

Elemental analysis: S; 58.13

(2) Production of Power Storage Device

A coin-shaped power storage device was produced in the same manner as in Example 1 except for the use of the one-linking polymer (13).

Example 4

(1) Preparation of Positive Electrode Active Material

A one-linking polymer (14) was synthesized by the following synthesis process.

[Chem. 20]

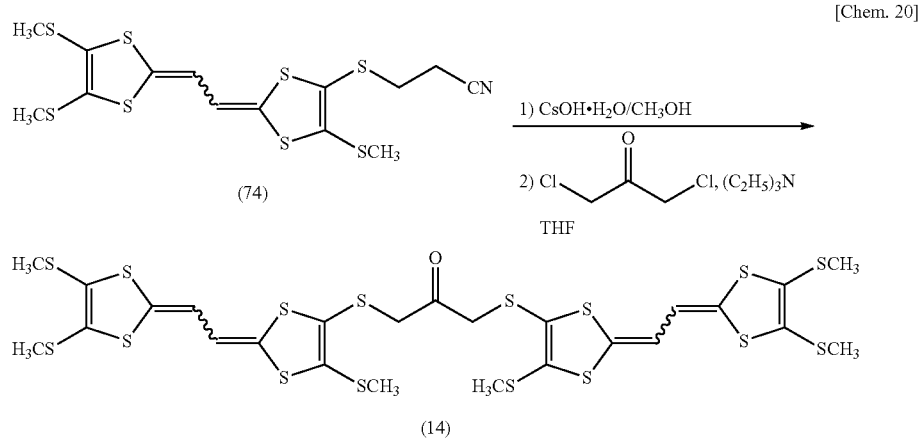

(74)

(14)

[Synthesis of One-Linking Polymer (14)]

The one-linking polymer (14) was synthesized in the same manner as in Example 2, except that in the synthesis process of the one-linking polymer (12) of Example 2, 1,4-bischloromethylbenzene was replaced with the same equivalents of 1,3-dichloropropane-2-one. An elemental analysis (S, C, H) confirmed the presence of the one-linking polymer (14).

Elemental analysis: C; 35.10, H; 3.06, S; 59.97
$^1$H-NMR (270 Hz, CDCl$_3$) δ=2.80, 4.03, 6.07

(2) Production of Power Storage Device

A coin-shaped power storage device was produced in the same manner as in Example 1 except for the use of the one-linking polymer (14).

Example 5

(1) Preparation of Positive Electrode Active Material

A one-linking polymer (19) was synthesized by the following synthesis process.

temperature for 2 hours. The resulting reaction mixture was extracted with water and dichloromethane, washed, and dehydrated and dried with sodium sulfate to give a yellow powder.

An elemental analysis and an NMR confirmed that the yellow powder was the one-linking polymer (19). A gel permeation chromatography (hereinafter referred to as "GPC") showed that the one-linking polymer (19) had a molecular weight of 33650 in terms of polystyrene standard. Since the molecular weight per one reaction skeleton is approximately 571, it was confirmed that the one-linking polymer (19) was a 59-mer with the number n of repetition being approximately 58. Also, the result of an elemental analysis (S) confirmed that it was a one-linking polymer.

$^1$H NMR (270 MHz, CDCl$_3$) δ=1.25, 2.61, 3.09, 3.80
Elemental analysis: S; 43.78

(2) Production of Power Storage Device

A coin-shaped power storage device was produced in the same manner as in Example 1 except for the use of the one-linking polymer (19).

[Chem. 21]

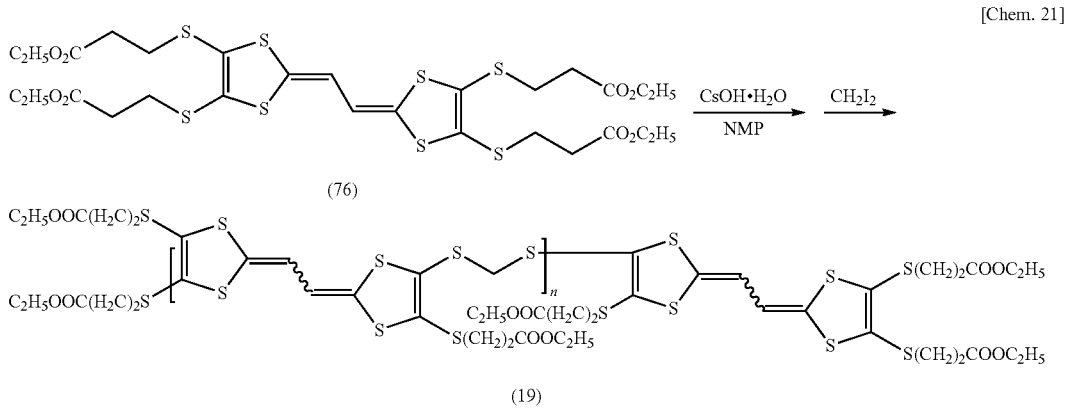

[Synthesis of One-Linking Polymer (19)]

106 mg of an EBDT derivative (76), 20 ml of N-methyl-2-pyrrolidone (NMP), and 51 mg of cesium hydroxide monohydrate were introduced into a 50-ml eggplant flask replaced with argon, and they were stirred at room temperature for 30 minutes. The resulting reaction mixture was mixed with 52 μl of diiodomethane and stirred at room Example 6

(1) Preparation of Positive Electrode Active Material

A one-linking polymer (20) was synthesized by the following synthesis process.

[Chem. 22]

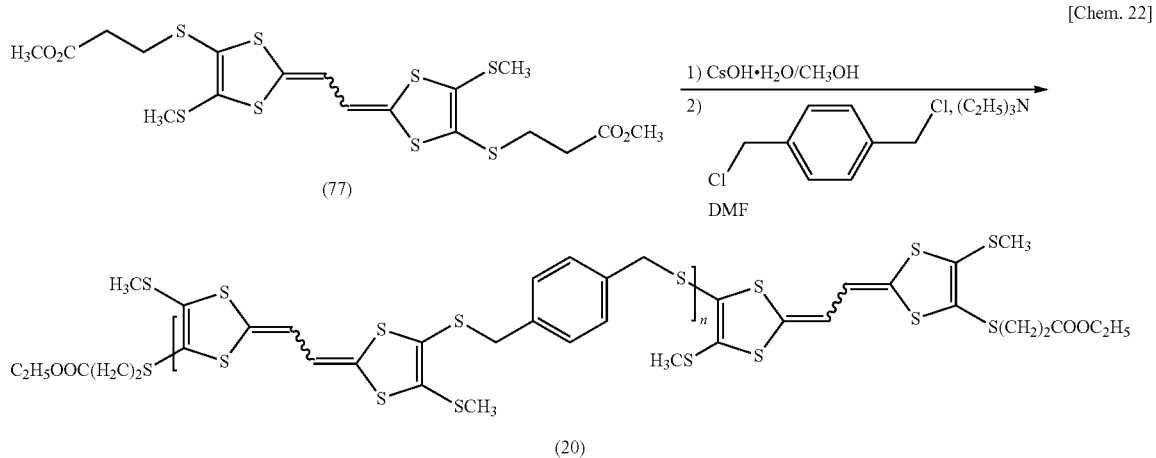

[Synthesis of One-Linking Polymer (20)]

The one-linking polymer (20) was synthesized in the same manner as in Example 2, except that in the synthesis process of the one-linking polymer (12) of Example 2, the compound (74) was replaced with a compound (77). An infrared absorption spectrum (hereinafter referred to as an "IR"), an elemental analysis, and a GPC confirmed the presence of the one-linking polymer (20). The GPC confirmed that the one-linking polymer (20) had a molecular weight of 8400 in terms of polystyrene standard and was an approximately 17-mer (n≈16).

IR (KBr): 1520, 1260, 850, 620 cm$^{-1}$

Elemental analysis: S; 51.00

(2) Production of Power Storage Device

A coin-shaped power storage device was produced in the same manner as in Example 1 except for the use of the one-linking polymer (20).

Example 7

(1) Preparation of Positive Electrode Active Material

A one-linking polymer (21) was synthesized by the following synthesis process.

[Chem. 23]

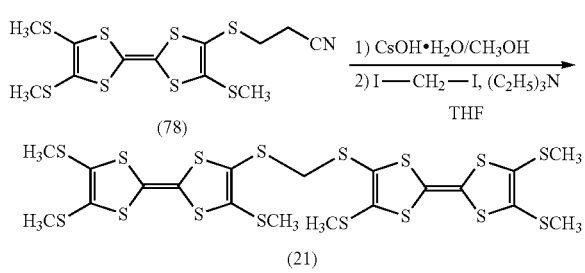

[Synthesis of One-Linking Polymer (21)]

The one-linking polymer (21) was synthesized in the same manner as in Example 1, except that in the synthesis process of the one-linking polymer (11) of Example 1, the compound (74) was replaced with a compound (78) and that triethylamine was used. An NMR confirmed the presence of the one-linking polymer (21).

$^1$H NMR (270 MHz, CDCl$_3$) δ=2.43, 4.16

(2) Production of Power Storage Device

A coin-shaped power storage device was produced in the same manner as in Example 1 except for the use of the one-linking polymer (21).

Example 8

(1) Preparation of Positive Electrode Active Material

A one-linking polymer (22) was synthesized by the following synthesis process.

[Chem. 24]

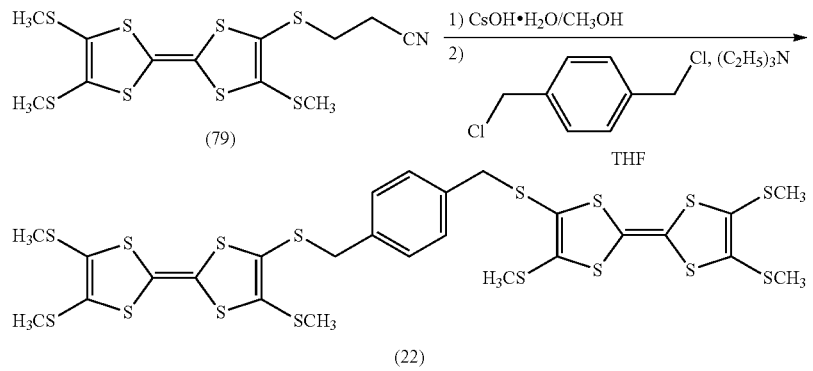

[Synthesis of One-Linking Polymer (22)]

The one-linking polymer (22) was synthesized in the same manner as in Example 2, except that in the synthesis process of the one-linking polymer (12) of Example 2, the compound (74) was replaced with a compound (79). An NMR and an elemental analysis showed the presence of the one-linking polymer (22).

Elemental analysis: C; 38.67, H; 3.08

$^1$H NMR (270 MHz, CDCl$_3$) δ=2.80, 4.59, 7.11

(2) Production of Power Storage Device

A coin-shaped power storage device was produced in the same manner as in Example 1 except for the use of the one-linking polymer (22).

Example 9

(1) Preparation of Positive Electrode Active Material

A one-linking polymer (23) was synthesized by the following synthesis process.

[Chem. 25]

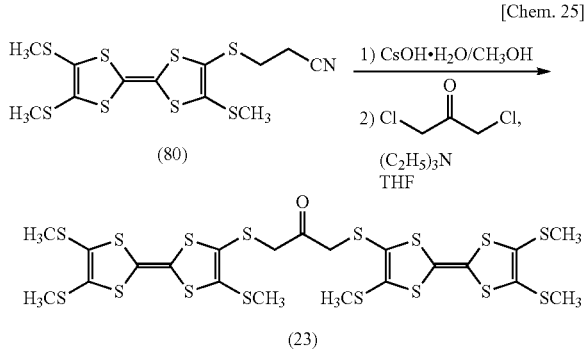

[Synthesis of One-Linking Polymer (23)]

The one-linking polymer (23) was synthesized in the same manner as in Example 4, except that in the synthesis process of the one-linking polymer (14) of Example 4, the compound (74) was replaced with a compound (80). An NMR and an elemental analysis confirmed the presence of the one-linking polymer (23).

Elemental analysis: C; 33.39, H; 3.06

$^{1}$H NMR (270 MHz, CDCl$_3$) δ=2.80, 4.04

(2) Production of Power Storage Device

A coin-shaped power storage device was produced in the same manner as in Example 1 except for the use of the one-linking polymer (23).

Example 10

(1) Preparation of Positive Electrode Active Material

A one-linking polymer (24) was synthesized by the following synthesis process.

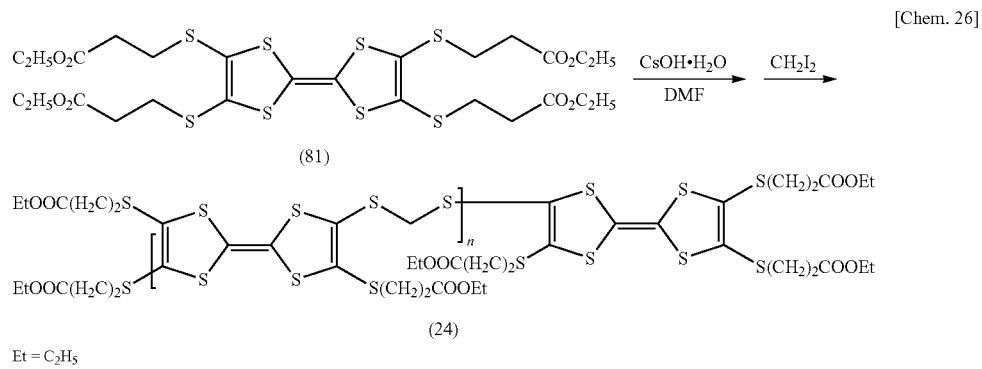

[Chem. 26]

[Synthesis of One-Linking Polymer (24)]

The one-linking polymer (24) was synthesized in the same manner as in Example 1, except that in the synthesis process of the one-linking polymer (11) of Example 1, the compound (74) was replaced with a compound (81) and that tetrahydrofuran (THF) was replaced with dimethylformamide (DMF). An NMR and an elemental analysis confirmed the presence of the one-linking polymer (24). Also, a GPC confirmed that the one-linking polymer (24) had a molecular weight of 40000 in terms of polystyrene standard and was an approximately 80-mer (n=approximately 79).

Elemental analysis: C; 30.30, H; 3.30

$^{1}$H-NMR (270 Hz, CDCl$_3$) δ=1.19, 2.54, 3.26, 4.04

(2) Production of Power Storage Device

A coin-shaped power storage device was produced in the same manner as in Example 1 except for the use of the one-linking polymer (24).

Example 11

(1) Preparation of Positive Electrode Active Material

A one-linking polymer (25) was synthesized by the following synthesis process.

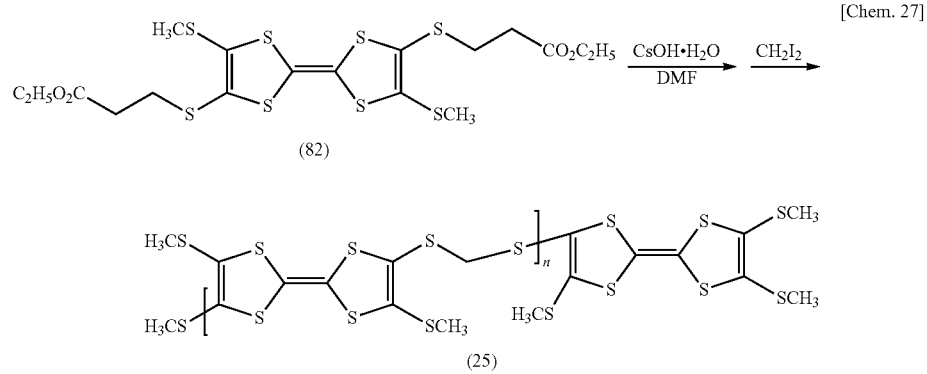

[Chem. 27]

[Synthesis of One-Linking Polymer (25)]

100 mg of a TTF derivative (82) and 20 ml of dimethylformamide (DMF) were introduced into a 50-ml Schlenk flask replaced with argon. Then, 71 mg of cesium hydroxide monohydrate and 76 μl of diiodomethane were added and stirred at room temperature for 2 hours. The resulting reaction mixture was washed with methanol and water to give 41 mg of a yellow solid. An NMR and an elemental analysis confirmed the presence of the one-linking polymer (25). A GPC confirmed that the one-linking polymer (25) had a molecular weight of 19200 in terms of polystyrene standard and was an approximately 51-mer (n=approximately 50).

Elemental analysis: C; 29.26, H; 3.03

$^1$H-NMR (270 Hz, CDCl$_3$): δ=2.30, 4.00

(2) Production of Power Storage Device

A coin-shaped power storage device was produced in the same manner as in Example 1 except for the use of the one-linking polymer (25).

Example 12

(1) Preparation of Positive Electrode Active Material

A one-linking polymer (26) was synthesized by the following synthesis process.

[Chem. 28]

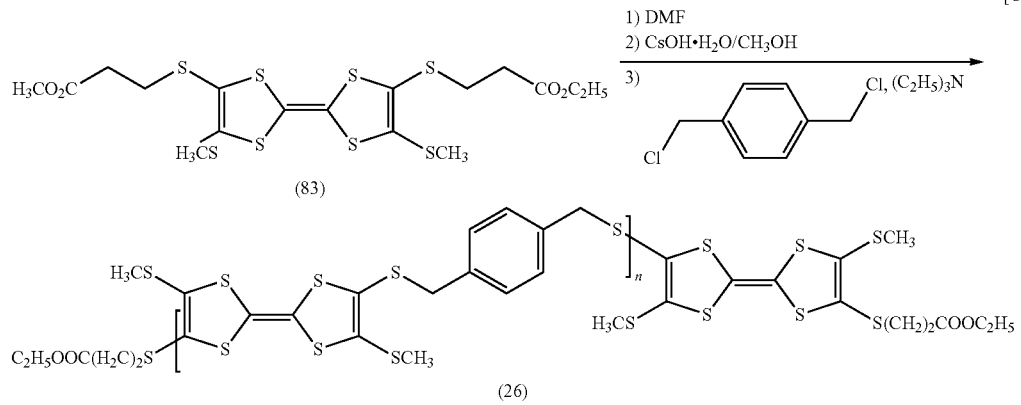

[Synthesis of One-Linking Polymer (26)]

304 mg of a TTF derivative (83) and 15 ml of dimethylformamide (DMF) were introduced into a 200-ml eggplant flask replaced with argon and stirred. Subsequently, a methanol solution of 230 mg of cesium hydroxide monohydrate was added and stirred at room temperature for 30 minutes. The resulting reaction mixture was mixed with 100 mg of 1,4-bischloromethylbenzene and 2.3 ml of triethylamine and stirred at room temperature for 5 hours. The resulting reaction mixture was filtered to isolate a solid, and the solid was washed with methanol and water, dehydrated with sodium sulfate, and dried to give a solid of 70.7 g.

An NMR confirmed that the solid was the one-linking polymer (26). Also, a GPC confirmed that the one-linking polymer (26) had a molecular weight of 5200 in terms of polystyrene standard and was an approximately decamer (n=approximately 9).

$^1$H-NMR (270 Hz, CDCl$_3$) δ=4.06, 2.30, 7.28

Elemental analysis: C; 43.29, H; 3.99

(2) Production of Power Storage Device

A coin-shaped power storage device was produced in the same manner as in Example 1 except for the use of the one-linking polymer (26).

Example 13

(1) Preparation of Positive Electrode Active Material

A one-linking polymer (28) was synthesized by the following synthesis process.

[Chem. 29]

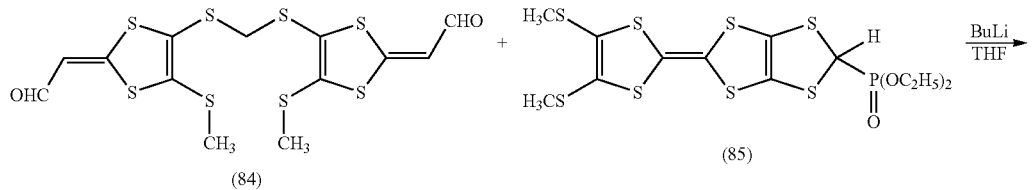

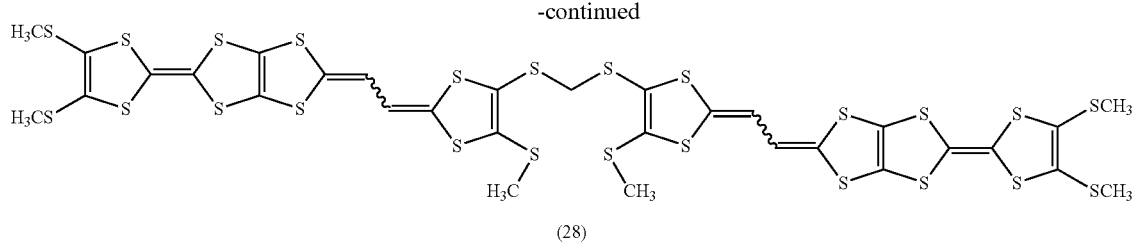

(28)

[Synthesis of One-Linking Polymer (28)]

0.1 mmol of a compound (84) and 0.25 mmol of a compound (85) were introduced into a 50-ml eggplant flask replaced with argon, and 20 ml of dry tetrahydrofuran was further added, followed by stirring at −70° C. for 20 minutes. BuLi (0.18 ml) was slowly added dropwise to the resulting reaction mixture, which was stirred for 1 hour and heated to −30° C. The resulting reaction mixture was mixed with methanol to precipitate a solid, which was then filtered out and dried to give 0.0779 g of an orange one-linking polymer (28) (yield 66.8%).

(2) Production of Power Storage Device

A coin-shaped power storage device was produced in the same manner as in Example 1 except for the use of the one-linking polymer (28).

Example 14

(1) Preparation of Positive Electrode Active Material

A one-linking polymer (32) was synthesized by the following synthesis process.

[Chem. 30]

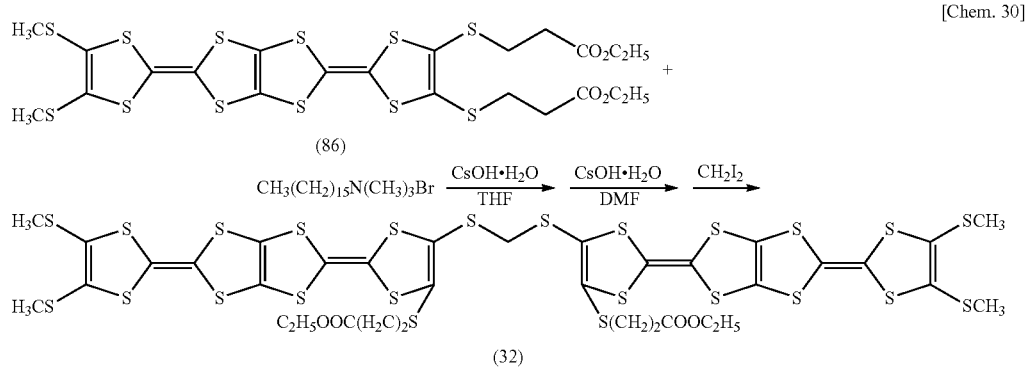

[Synthesis of One-Linking Polymer (32)]

116 mg of a TTP derivative (86), 73 mg of hexadecyltrimethylammonium bromide, and 20 ml of tetrahydrofuran (THF) were introduced into a 200-ml eggplant flask replaced with argon, and 24.6 mg of cesium hydroxide monohydrate was further added with stirring. The resulting reaction mixture was mixed with 2.2 mg of cesium hydroxide monohydrate and 10 ml of dimethylformamide (DMF) with stirring, and 53 μl of diiodomethane was further added with stirring. The resulting reaction mixture was filtered to isolate a solid, and the solid was washed with methanol and water and vacuum-dried to give 82.8 mg of a red solid. An NMR and an elemental analysis confirmed the presence of the one-linking polymer (32).

Elemental analysis: C; 27.76, H; 1.96

$^1$H-NMR (270 Hz, CDCl$_3$): δ=0.90, 1.26, 1.36, 2.52, 2.72, 2.96, 4.01, 7.20

(2) Production of Power Storage Device

A coin-shaped power storage device was produced in the same manner as in Example 1 except for the use of the one-linking polymer (32).

Example 15

(1) Preparation of Positive Electrode Active Material

A one-linking polymer (34) was synthesized by the following synthesis process.

[Chem. 31]

Synthesis of Compound (88)

0.52 g of a compound (87) was introduced into a 200-ml two-necked eggplant flask, and the atmosphere inside the flask was replaced with argon. Subsequently, 50 ml of acetonitrile was added, and a solution of 0.19 g of cesium hydroxide monohydrate in 30 ml of methanol was added, followed by stirring at room temperature for 30 minutes. Since some remained undissolved, 30 ml of tetrahydrofuran was added and further stirred at room temperature for 30 minutes. 0.5 ml of chloroiodomethane was added thereto and stirred for 2 hours.

The resulting reaction mixture was extracted with water and methylene chloride, washed, dehydrated with sodium sulfate, and dried. Thereafter, it was concentrated by an evaporator and separated by column chromatography (silica gel, methylene chloride). It was further concentrated by the evaporator and reprecipiated by using hexane. The resulting solid was washed and vacuum dried to give 0.41 g of a compound (88). The yield was 80.3%. A compound (89) was synthesized in the same manner as described above except for the use of the compound (88) instead of the compound (87).

[Synthesis of One-Linking Polymer (34)]

0.22 g of the compound (89) was introduced into a 100-ml three-necked eggplant flask, and the atmosphere inside the flask was replaced with argon. Subsequently, 10 ml of tetrahydrofuran (THF) was added, and a solution of 0.18 g of cesium hydroxide monohydrate in 10 ml of methanol was added, followed by stirring at room temperature for 30 minutes. A solution prepared by dissolving 0.40 g of the compound (88) in 15 ml of tetrahydrofuran in an argon atmosphere and 3 ml of triethylamine were added and stirred all night. The resulting reaction mixture was extracted with water and methylene chloride, washed, dehydrated with sodium sulfate, and dried. Thereafter, it was concentrated by an evaporator and separated by column chromatography (silica gel, methylene chloride:hexane=1:2). It was further concentrated by the evaporator and reprecipitated by using methanol. The resulting solid was washed and vacuum dried to give 0.26 g of the one-linking polymer (34). The yield was 49.0%.

(2) Production of Power Storage Device

A coin-shaped power storage device was produced in the same manner as in Example 1 except for the use of the one-linking polymer (34).

Example 16

(1) Preparation of Positive Electrode Active Material

A one-linking polymer (37) was synthesized by the following synthesis process.

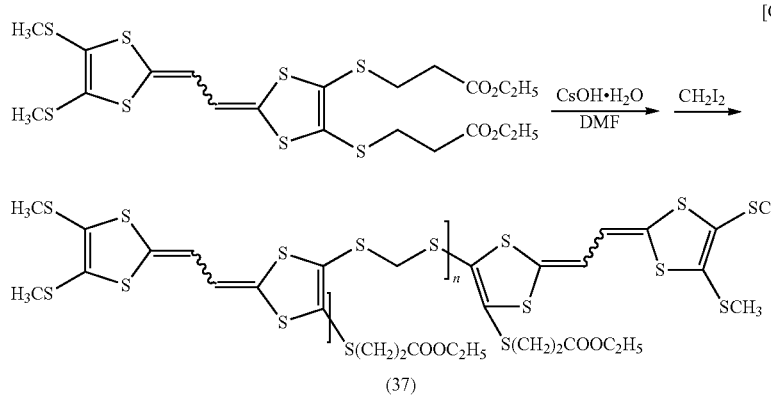

[Chem. 32]

[Synthesis of One-Linking Polymer (37)]

100 mg of an EBDT derivative (90) and 20 ml of dimethylformamide (DMF) were introduced into a 50-ml Schlenk flask replaced with argon, and 71 mg of cesium hydroxide monohydrate and 76 μl of diiodomethane were added thereto and stirred at room temperature for 2 hours. The resulting reaction mixture was washed with methanol and water and filtered to isolate a solid. An NMR and an elemental analysis confirmed that the solid thus obtained was the one-linking polymer (37). A GPC confirmed that the one-linking polymer (37) had a molecular weight of 3500 in terms of polystyrene standard and was an approximately hexamer (n=approximately 5).

$^1$H NMR (270 MHz, CDCl$_3$) δ=1.56, 2.40, 4.21, 5.68
Elemental analysis: C; 32.92, H; 2.72

(2) Production of Power Storage Device

A coin-shaped power storage device was produced in the same manner as in Example 1 except for the use of the one-linking polymer (37).

Example 17

(1) Preparation of Positive Electrode Active Material

A one-linking polymer (38) was synthesized by the following synthesis process.

[Chem. 33]

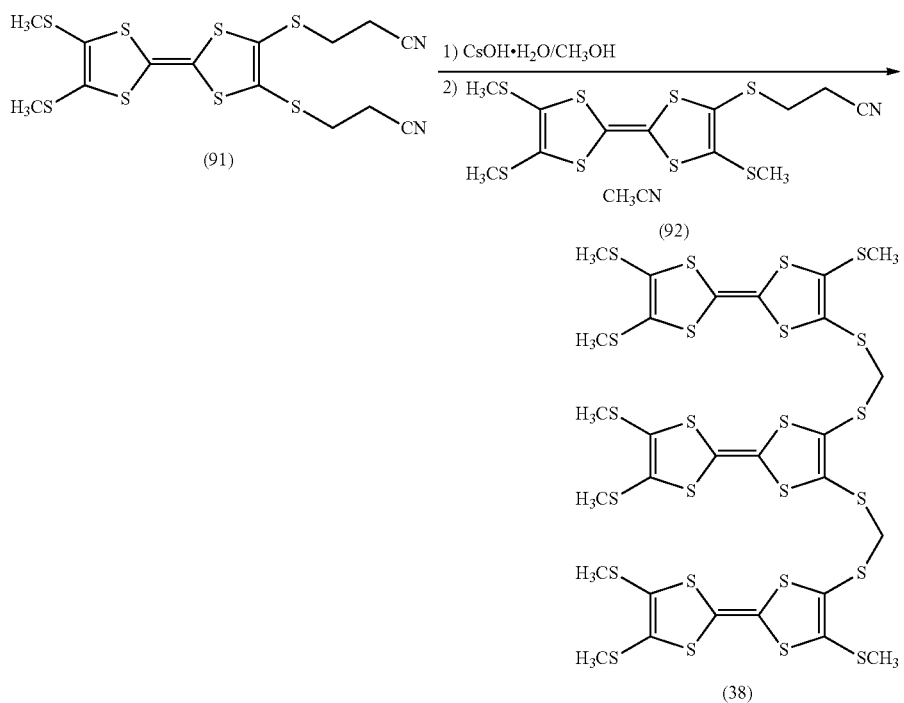

[Synthesis of One-Linking Polymer (38)]

108 mg of a TTF derivative (91) and 25 ml of acetonitrile were introduced into a 50-ml eggplant flask replaced with argon, and a methanol solution of 43.6 mg of cesium hydroxide monohydrate was further added and stirred for 30 minutes. The resulting reaction mixture was mixed with a TTF derivative (92) and stirred at room temperature all night. The resulting reaction mixture was extracted with dichloromethane, washed with water and sodium chloride, and dried to give 32 mg of a powder. An NMR and an elemental analysis confirmed that the powder was the one-linking polymer (38).

$^1$H NMR (270 MHz, CDCl$_3$) δ=2.45, 4.79

Elemental analysis: C; 29.53, H; 2.54

(2) Production of Power Storage Device

A coin-shaped power storage device was produced in the same manner as in Example 1 except for the use of the one-linking polymer (38).

Example 18

(1) Preparation of Positive Electrode Active Material

A one-linking polymer (39) was synthesized by the following synthesis process.

filtered to isolate a solid, and the solid was washed with water and sodium chloride and dried to give 13 mg of a powder.

An NMR and an elemental analysis confirmed that the powder was the one-linking polymer (39). A GPC confirmed that the one-linking polymer (39) had a molecular weight of 48500 in terms of polystyrene standard and was an approximately 68-mer (n=approximately 66). The one-linking polymer (39) is a polymer in which reaction skeletons comprising a derivative of a condensation product of EBDT and TTF are linked in a zigzag. Since the number of the reaction skeletons in the zigzag portion was approximately 66, n=approximately 66. In fact, since each end has one reaction skeleton, the one-linking polymer (39) as a whole is an approximately 68-mer.

$^1$H NMR (270 MHz, CDCl$_3$) δ=1.27, 3.15, 6.07

Elemental analysis: S; 49.08

[Chem. 34]

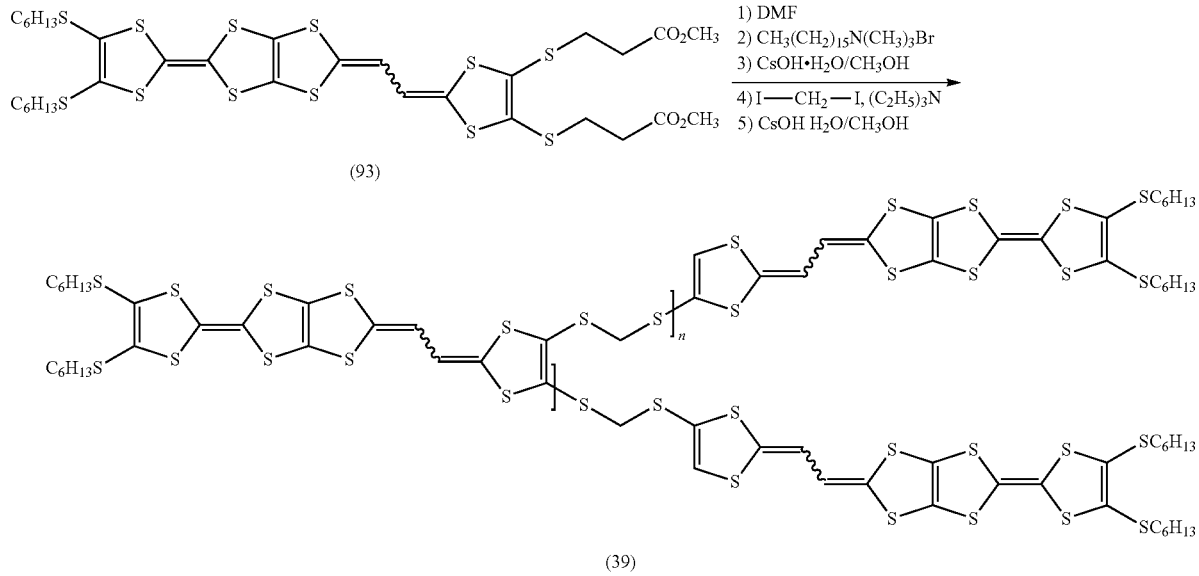

[Synthesis of One-Linking Polymer (39)]

100 mg of a derivative (93) of a condensation product of TTF and EBDT and 60 ml of dimethylformamide (DMF) were introduced into a 200-ml eggplant flask replaced with argon. 110 mg of hexadecyltrimethylammonium bromide and a methanol solution of 38 mg of cesium hydroxide monohydrate were added and stirred for 30 minutes. The resulting reaction mixture was mixed with 46 μl of diiodomethane, a methanol solution of 168 mg of cesium hydroxide monohydrate, and 3 ml of triethylamine and stirred for 2 hours. The resulting reaction mixture was (2) Production of Power Storage Device A coin-shaped power storage device was produced in the same manner as in Example 1 except for the use of the one-linking polymer (39).

Example 19

(1) Preparation of Electrode Active Material

A two-linking polymer (40) was synthesized by the following synthesis process.

[Chem. 35]

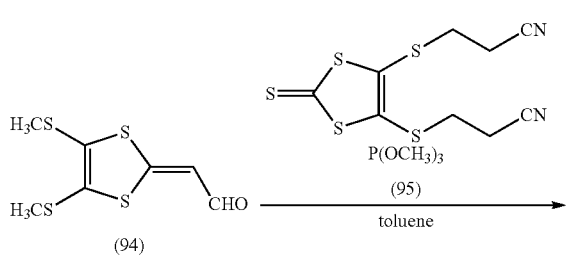

-continued

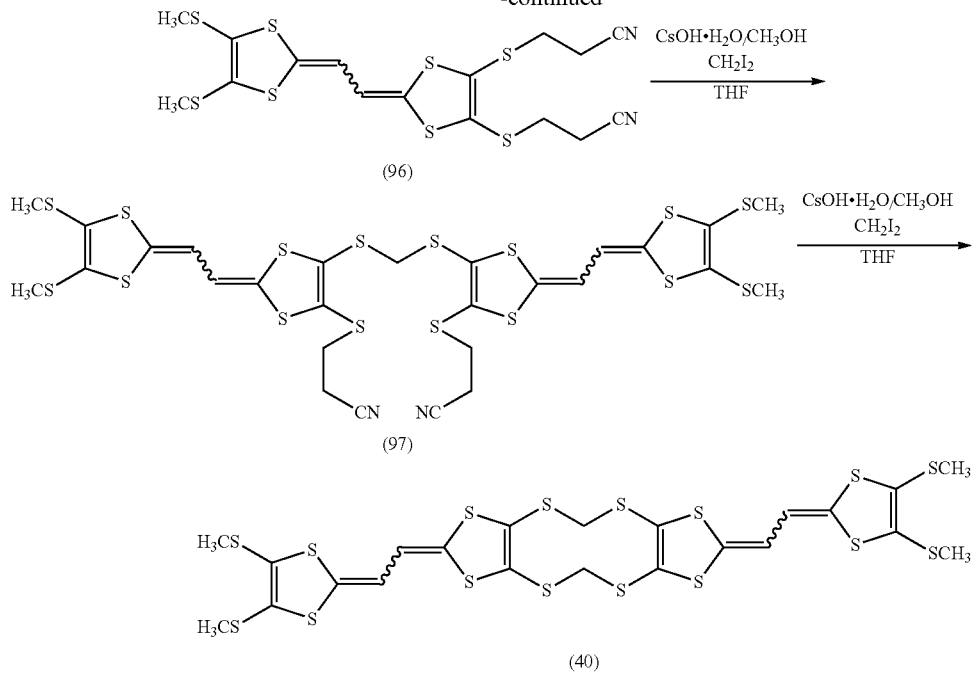

Synthesis of Compound (96)

0.75 g of a compound (94) and 1.45 g of a compound (95) were introduced into a 200-ml two-necked eggplant flask, followed by argon replacement. 13 ml of dry toluene and 13 ml of dry trimethyl phosphite were added thereto and stirred at 110° C. for 2 hours. Upon completion of the reaction, the reaction mixture was concentrated by an evaporator and separated by column chromatography (silica gel, methylene chloride). After removal of the solvent by the evaporator, it was vacuum dried to give 0.85 g of a compound (96). The yield was 54.9%.

Synthesis Method of Compound (97)

0.61 g of the compound (96) was introduced into a 200-ml two-necked eggplant flask, followed by argon replacement. 45 ml of tetrahydrofuran was added, and a solution of 0.21 g of cesium hydroxide monohydrate in 10 ml of methanol was further added, followed by stirring at room temperature for 30 minutes. The resulting reaction mixture was mixed with 1.0 ml of diiodomethane, stirred for 2 hours, extracted with water and methylene chloride, washed, and dehydrated with sodium sulfate, and dried. Thereafter, it was concentrated by an evaporator and separated by column chromatography (silica gel, methylene chloride). After removal of the solvent by the evaporator, it was vacuum dried to give 0.48 g of a compound (97). The yield was 88.5%.

[Synthesis of Two-Linking Polymer (40)]

0.47 g of the compound (97) and 50 ml of tetrahydrofuran were introduced into a 200-ml eggplant flask, and a solution of 0.22 g of cesium hydroxide monohydrate in methanol (20 ml) was added thereto and stirred at room temperature for 30 minutes. The resulting reaction mixture was mixed with 0.05 ml of diiodomethane and stirred for 2 hours. The reaction mixture was developed in methanol, filtered, washed with water and methanol, and vacuum dried to give a two-linking polymer (40). An IR confirmed the presence of the two-linking polymer (40).

IR (KBr) 2913, 1522, 1489, 1421 $cm^{-1}$

Also, an X-ray diffraction analysis of the two-linking polymer (40) showed a diffraction pattern derived from the compound, thereby confirming that the two-linking polymer (40) was crystalline. The X-ray diffraction analysis was performed using Cu—Kα radiation as the incident X-ray according to the 2θ/θ method in a measurement angle range of 1° to 34° (2θ) at a scanning speed of 1°/min.

(2) Production of Power Storage Device

A coin-shaped power storage device was produced in the same manner as in Example 1 except for the use of the two-linking polymer (40).

Example 20

A two-linking polymer (41) was synthesized by the following synthesis process.

[Chem. 36]

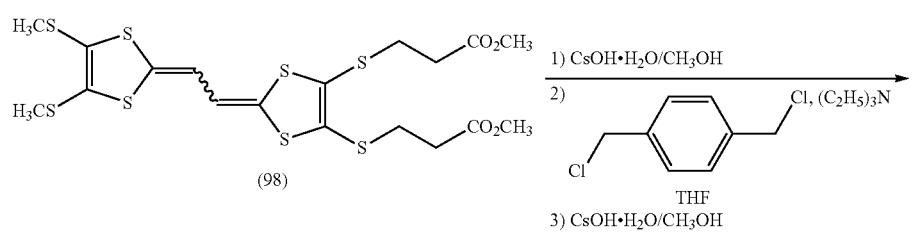

-continued

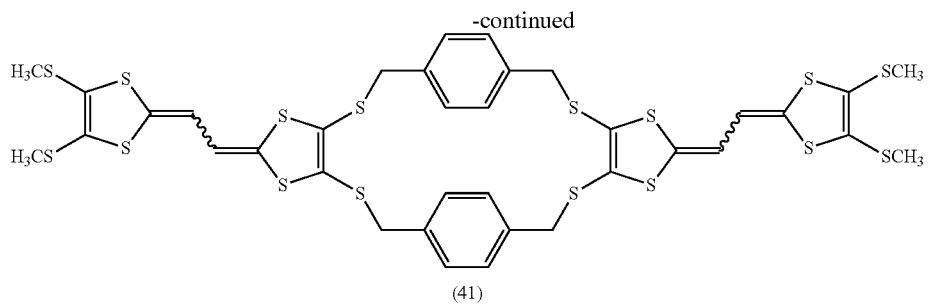

(41)

[Synthesis of Two-Linking Polymer (41)]

The two-linking polymer (41) was synthesized in the same manner as in Example 2, except that in the synthesis process of the one-linking polymer (12) of Example 2, the compound (74) was replaced with a compound (98). An NMR confirmed the presence of the two-linking polymer (41).

$^1$H NMR (270 MHz, CDCl$_3$) δ=2.33, 4.53, 5.70, 7.20, 7.30

(2) Production of Power Storage Device

A coin-shaped power storage device was produced in the same manner as in Example 1 except for the use of the two-linking polymer (41).

Example 21

A two-linking polymer (59) was synthesized by the following synthesis process.

plant flask replaced with argon. Subsequently, 64 mg of hexadecyltrimethylammonium bromide and 38 mg of cesium hydroxide monohydrate were added, and 56 ml of dimethylformamide (DMF) was further added, followed by stirring for 1 hour. The resulting reaction mixture was mixed with 22.9 μl of diiodomethane and stirred for 1 hour. The reaction mixture was filtered to isolate a solid, which was then washed with water and methanol and dried to give 58 mg of an orange solid. The yield was 74%. An elemental analysis confirmed that the solid was the two-linking polymer (59).

Elemental analysis: C; 40.08, H; 4.12; S: 55.23

(2) Production of Power Storage Device

A coin-shaped power storage device was produced in the same manner as in Example 1 except for the use of the two-linking polymer (59).

[Chem. 37]

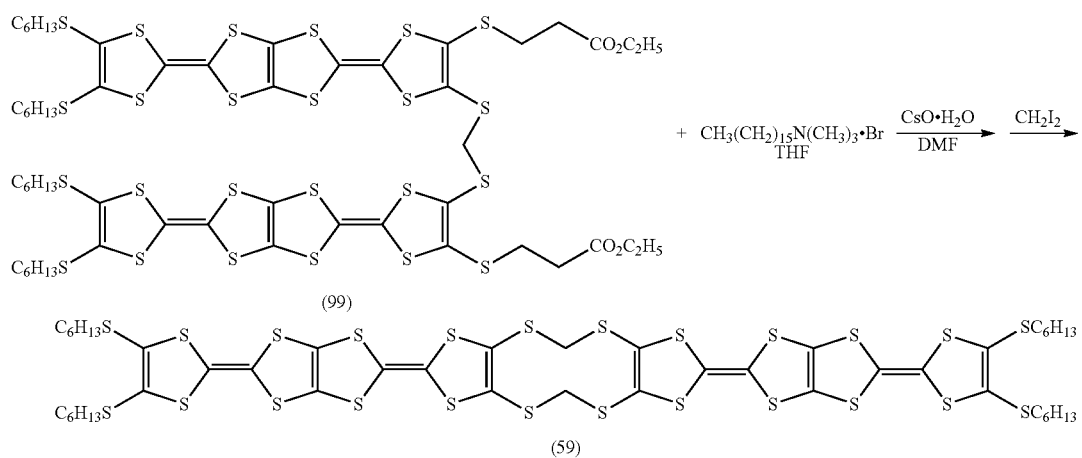

[Synthesis of Two-Linking Polymer (59)]

89 mg of a derivative (99) of a dimer of TTP synthesized in the same manner as in Example 17 and 112 ml of tetrahydrofuran (THF) were introduced into a 200-ml egg- Example 22

A two-linking polymer (44) was synthesized by the following synthesis process.

[Chem. 38]

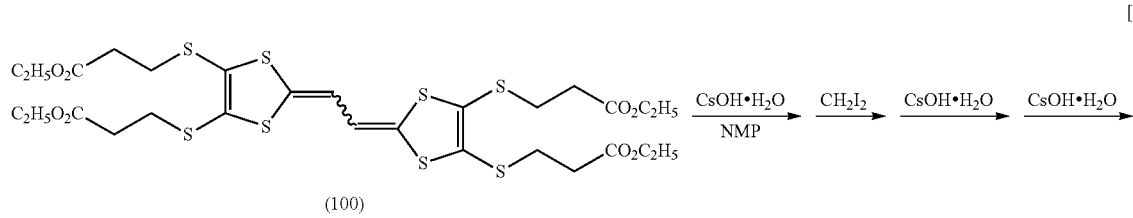

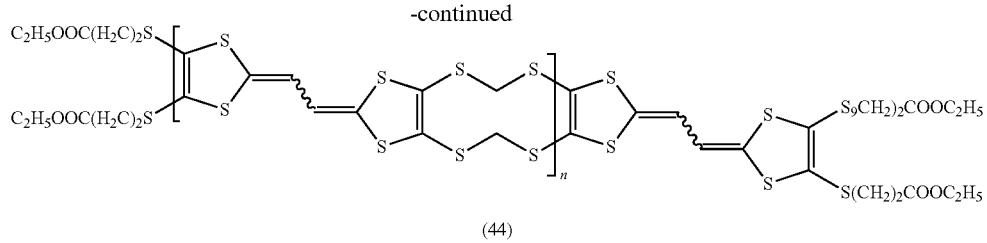

(44)

[Synthesis of Two-Linking Polymer (44)]

49 mg of an EBDT derivative (100), 30 ml of N-methyl-2-pyrrolidone (NMP), and 49 mg of cesium hydroxide monohydrate were introduced into a 50-ml eggplant flask replaced with argon, and stirred for 30 minutes. Subsequently, 52 μl of diiodomethane was added and stirred at room temperature for 2 hours. The resulting reaction mixture was mixed with 51 mg of cesium hydroxide monohydrate and stirred for 1 hour. Further, 49 mg of cesium hydroxide monohydrate was added and stirred for 1 hour. The resulting reaction mixture was filtered to isolate a solid, and the solid was washed with water and methanol and dried to give a powder.

An NMR and an elemental analysis confirmed that the powder was the two-linking polymer (44). Also, a GPC confirmed that the two-linking polymer (44) had a molecular weight of 33000 in terms of polystyrene standard, and was an approximately 80-mer (n=approximately 79).

Elemental analysis: C; 32.06, H; 2.68, S; 65.30

(2) Production of Power Storage Device

A coin-shaped power storage device was produced in the same manner as in Example 1 except for the use of the two-linking polymer (44).

Example 23

(1) Preparation of Electrode Active Material

A two-linking polymer (45) was synthesized by the following synthesis process.

[Chem. 39]

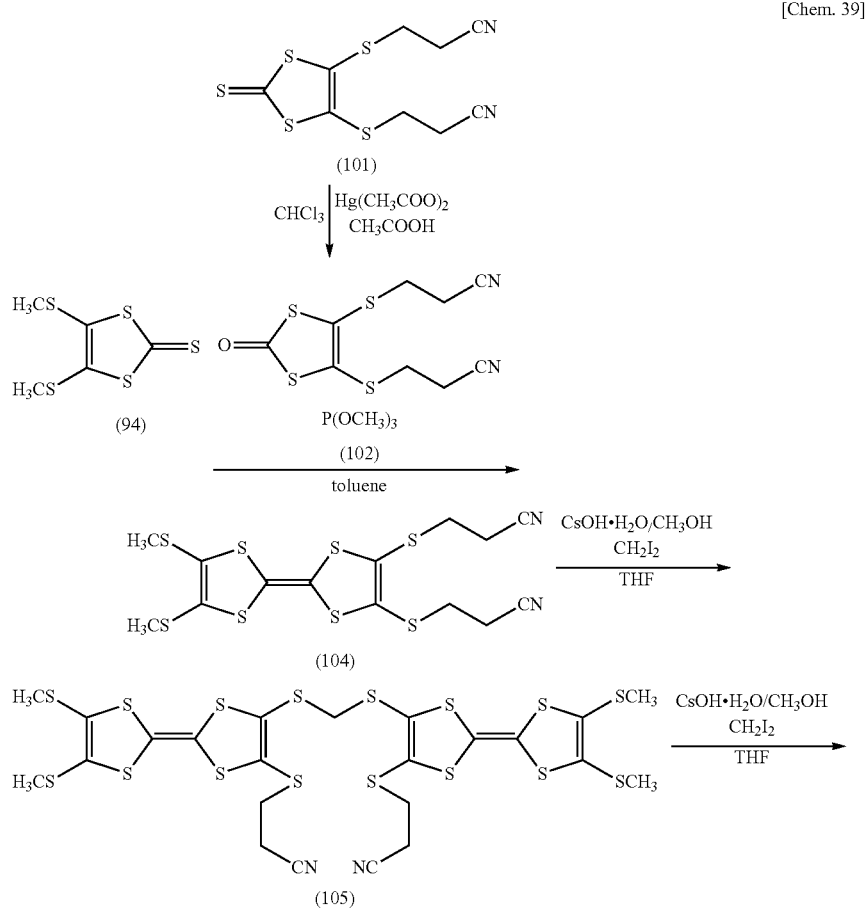

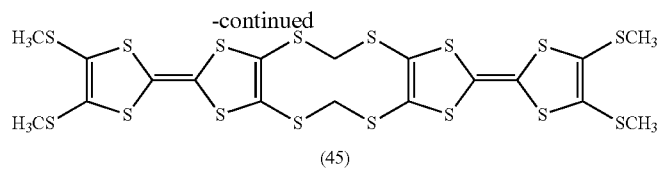

(45)

Synthesis of Compound (102)

15.0 g of a compound (101) was introduced into a 500-ml two-necked eggplant flask, followed by argon replacement. 350 ml of chloroform, 23.5 g of mercury acetate, and 83 ml of acetic acid were added and stirred at room temperature for 2 hours. The resulting reaction mixture was filtered, extracted with the addition of water and an aqueous solution of sodium hydrogen carbonate, washed, dehydrated with sodium sulfate, and dried. Thereafter, it was concentrated by an evaporator and separated by column chromatography (silica gel, methylene chloride). After removal of the solvent by the evaporator, it was vacuum dried to give 3.02 g of a compound (102). The yield was 21.3%.

Synthesis of Compound (104)

1.15 g of the compound (102) and 0.90 g of a compound (103) were introduced into a 100-ml two-necked eggplant flask, followed by argon replacement. 20 ml of dry triethyl phosphite was added thereto, and stirred in toluene at 110° C. for 2 hours. Upon completion of the reaction, the resulting reaction mixture was mixed with hexane and cooled, and the resulting precipitate was filtered. The resulting solid was dissolved in methylene chloride and separated by column chromatography (silica gel, methylene chloride). After removal of the solvent by an evaporator, it was vacuum dried to give 1.25 g of a compound (104). The yield was 67.1%.

Synthesis of Compound (105)

1.0 g of the compound (104) was introduced into a 200-ml two-necked eggplant flask, followed by argon replacement. 50 ml of tetrahydrofuran was added, and a solution of 0.36 g of cesium hydroxide monohydrate in methanol (30 ml) was added and stirred at room temperature for 30 minutes. The resulting reaction mixture was mixed with 0.09 ml of diiodomethane and stirred for 2 hours. The reaction mixture was extracted with water and methylene chloride, washed, and dehydrated with sodium sulfate, and dried. Thereafter, it was concentrated by an evaporator and separated by column chromatography (silica gel, methylene chloride:hexane=2:1). After removal of the solvent by the evaporator, it was vacuum dried to give 0.80 g of a compound (105). The yield was 89.0%.

[Synthesis of Two-Linking Polymer (45)]

0.78 g of the compound (105) and 40 ml of tetrahydrofuran were introduced into a 200-ml eggplant flask. A solution of 0.37 g of cesium hydroxide monohydrate in 20 ml of methanol was added thereto, followed by stirring at room temperature for 30 minutes. Thereafter, 0.1 ml of diiodomethane was added, followed by stirring for 2 hours. The resulting reaction mixture was developed in methanol, filtered, washed with water and methanol, and vacuum dried to give the two-linking polymer (45). An IR confirmed the presence of the two-linking polymer (45).

IR (KBr) 2916, 1654, 1420, 1203 cm$^{-1}$

An X-ray diffraction analysis of the two-linking polymer (45) showed a diffraction pattern derived from the two-linking polymer (45), thereby confirming that the two-linking polymer (45) was crystalline. The X-ray diffraction analysis was performed using Cu—Kα radiation as the incident X-ray according to the 2θ/θ method in a measurement angle range of 1° to 34° (2θ) at a scanning speed of 1°/min.

(2) Production of Power Storage Device

A coin-shaped power storage device was produced in the same manner as in Example 1 except for the use of the two-linking polymer (45).

Example 24

(1) Preparation of Electrode Active Material

A two-linking polymer (48) was synthesized by the following synthesis process.

[Chem. 40]

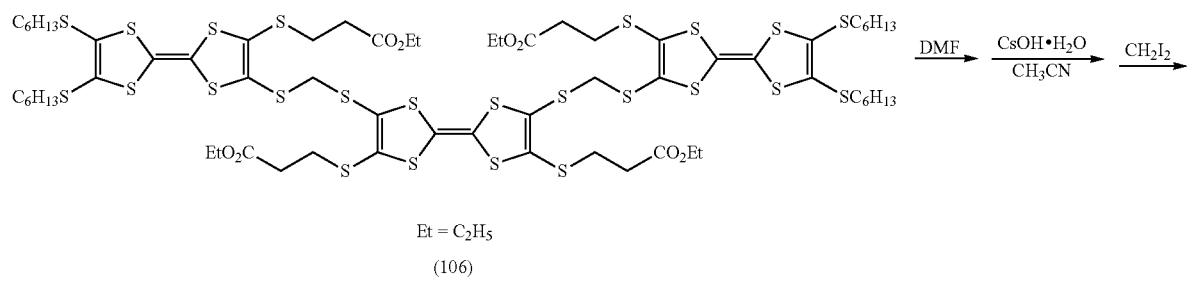

Et = C$_2$H$_5$
(106)

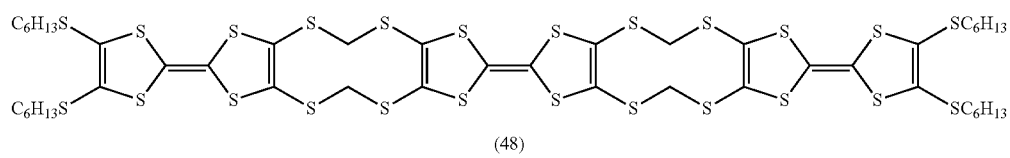

(48)

[Synthesis of Two-Linking Polymer (48)]

85.5 mg of a TTF derivative (106) and 15 ml of dimethylformamide (DMF) were introduced into a 100-ml eggplant flask replaced with argon. Further, 51.3 mg of cesium hydroxide monohydrate and 3 ml of acetonitrile were added and stirred for 30 minutes. Subsequently, 43.4 μl of diiodomethane was added and stirred at room temperature all night. The resulting reaction mixture was put into methanol, and the resulting precipitate was washed with methanol and dried to give 44.6 mg of a red powder. An elemental analysis confirmed that the red powder was the two-linking polymer (48).

Elemental analysis: C; 39.96, H; 4.37, S; 55.66

(2) Production of Power Storage Device

A coin-shaped power storage device was produced in the same manner as in Example 1 except for the use of the two-linking polymer (48).

Example 25

(1) Preparation of Electrode Active Material

A two-linking polymer (49) was synthesized by the following synthesis process.

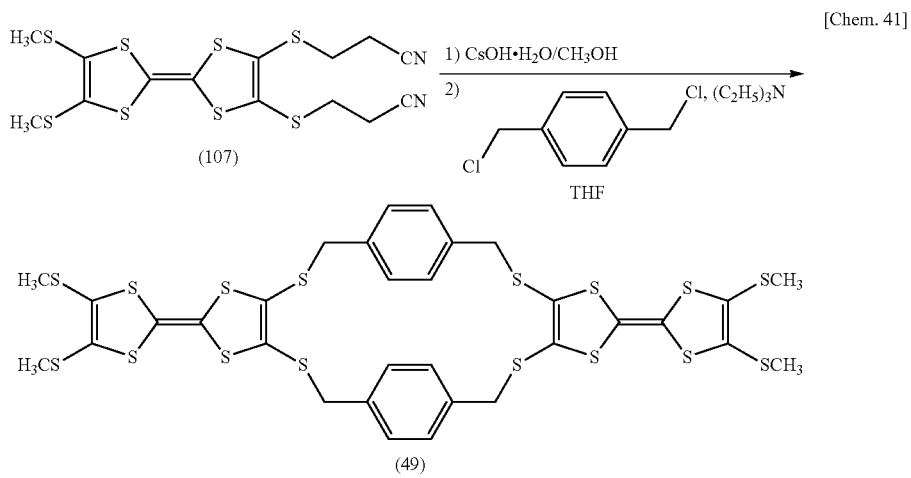

[Chem. 41]

[Synthesis of Two-Linking Polymer (49)]

The two-linking polymer (49) was synthesized in the same manner as in Example 2, except that in the synthesis process of the one-linking polymer (12) of Example 2, the compound (74) was replaced with a compound (107). An NMR confirmed the presence of the two-linking polymer (49).

$^1$H-NMR (270 Hz, CDCl$_3$): 2.44, 3.83, 7.18, 7.26

(2) Production of Power Storage Device

A coin-shaped power storage device was produced in the same manner as in Example 1 except for the use of the two-linking polymer (49).

Example 26

(1) Preparation of Electrode Active Material

A two-linking polymer (50) was synthesized by the following synthesis process.

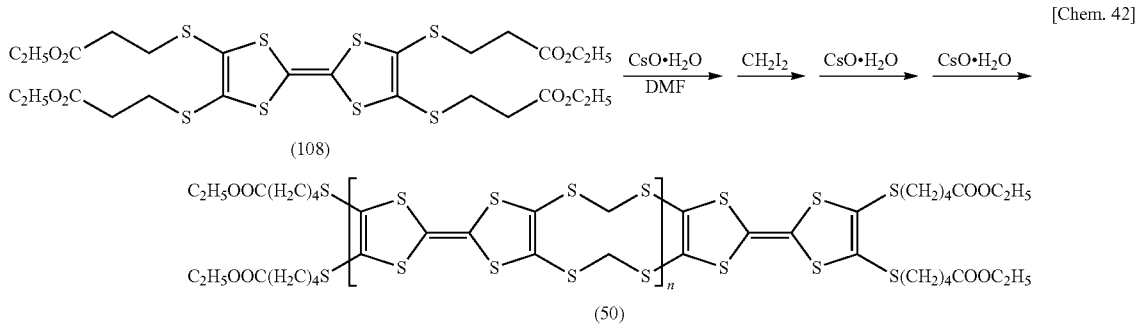

[Chem. 42]

[Synthesis of Two-Linking Polymer (50)]

The two-linking polymer (50) was synthesized in the same manner as in Example 22, except that the EBDT derivative (100) was replaced with a TTF derivative (108). An NMR and an elemental analysis confirmed the presence of the two-linking polymer (50).

$^1$H-NMR (270 Hz, CDCl$_3$): 1.19, 2.54, 3.26, 4.04

Elemental analysis: C; 27.30, H; 2.30, S; 70.12

(2) Production of Power Storage Device

A coin-shaped power storage device was produced in the same manner as in Example 1 except for the use of the two-linking polymer (50).

Example 27

(1) Preparation of Electrode Active Material

A two-linking polymer (52) was synthesized by the following synthesis process.

[Chem. 43]

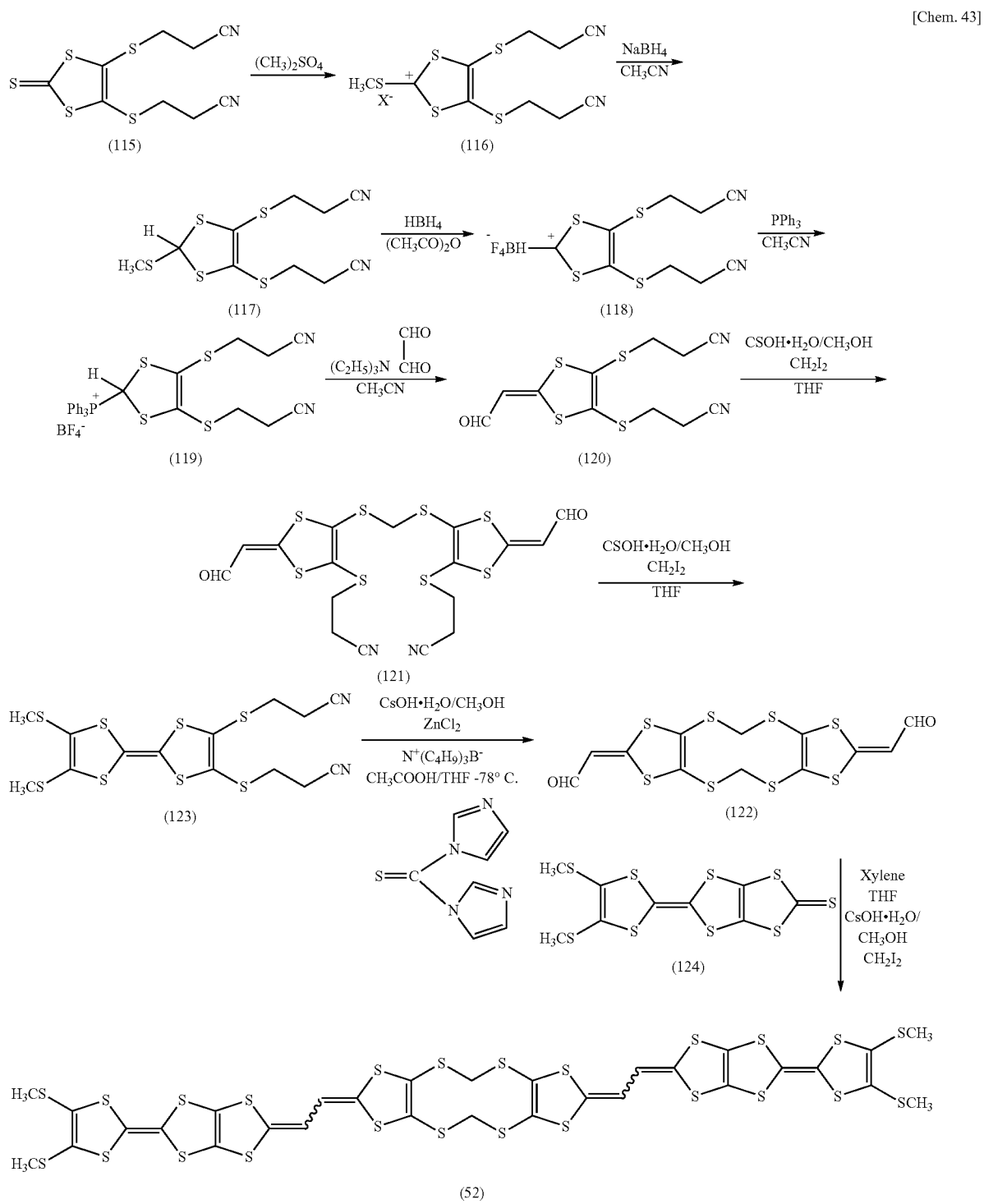

Synthesis of Compound (116)

5.37 g of a compound (115) and 33.5 ml of dimethyl sulfate were introduced into a 500-ml two-necked eggplant flask, followed by argon replacement. They were stirred at 70° C. for 1 hour. Upon completion of the reaction, the resulting reaction mixture was mixed with diethyl ether, cooled to form a precipitate, and subjected to a decantation to give a compound (116).

Synthesis of Compound (117)

80 ml of acetonitrile was added to the compound (116), and with cooling in an ice bath, 1.33 g of sodium borohydride was added and stirred for 1 hour. The resulting reaction mixture was introduced into ice water little by little, extracted with water and methylene chloride, washed, dehydrated with sodium sulfate, and dried. Thereafter, it was concentrated by an evaporator and separated by column chromatography (silica gel, methylene chloride). After removal of the solvent by the evaporator, it was vacuum dried to give 3.53 g of a compound (117). The yield was 62.9%.

Synthesis of Compound (118)

5.8 g of the compound (117) and 90 ml of acetic anhydride were introduced into a 300-ml two-necked eggplant flask, and with cooling in an ice bath, 7.58 g of a 42 wt % aqueous solution of tetrafluoroboric acid was added and stirred for 1 hour. Upon completion of the reaction, diethyl ether was added to form a precipitate, and a decantation and a vacuum drying were performed to give 3.98 g of a compound (118). The yield was 61.0%.

Synthesis of Compound (119)

3.98 g of the compound (118), 40 ml of acetonitrile, and 3.2 g of triphenylphosphine were introduced into a 300-ml eggplant flask, and were stirred at room temperature for 1 hour. Upon completion of the reaction, the resulting reaction mixture was mixed with diethyl ether to form a precipitate, and a decantation and a vacuum drying were performed to give 5.29 g of a compound (119). The yield was 77.0%.

Synthesis of Compound (120)

5.29 g of the compound (119), 110 ml of acetonitrile, 4.93 g of a 40-wt % aqueous solution of glyoxal, and 12 ml of triethylamine were introduced into a 300-ml eggplant flask, and were stirred at room temperature for 2 hours. Upon completion of the reaction, the resulting reaction mixture was extracted with water and methylene chloride, washed, dehydrated with sodium sulfate, and dried. Thereafter, it was concentrated by an evaporator and separated by column chromatography (silica gel, methylene chloride). After removal of the solvent by the evaporator, it was vacuum dried to give 1.96 g of a compound (120). The yield was 73.4%.

Synthesis of Compound (121)

1.96 g of the compound (120) was introduced into a 200-ml two-necked eggplant flask, followed by argon replacement. 50 ml of tetrahydrofuran was added, and a solution of 1.1 g of cesium hydroxide monohydrate in 25 ml of methanol was added and stirred at room temperature for 30 minutes. 0.25 ml of diiodomethane was added thereto and stirred for 2 hours. The resulting reaction mixture was extracted with water and methylene chloride, washed, dehydrated with sodium sulfate, and dried. Thereafter, it was concentrated by an evaporator and separated by column chromatography (silica gel, methylene chloride). After removal of the solvent by the evaporator, it was vacuum dried to give 0.55 g of a compound (121). The yield was 32.9%.

Synthesis of Compound (122)

0.55 g of the compound (121) was introduced into a 200-ml two-necked eggplant flask, followed by argon replacement. 30 ml of tetrahydrofuran was added, and a solution of 0.7 g of cesium hydroxide monohydrate in 20 ml of methanol was added and stirred at room temperature for 30 minutes. 0.1 ml of diiodomethane was added and stirred for 2 hours. The resulting reaction mixture was mixed with methanol, and the resulting precipitate was filtered out and vacuum dried to give 0.30 g of a compound (122). The yield was 67.8%.

Synthesis of Compound (124)

1.34 g of a compound (123) was introduced into a 300-ml two-necked eggplant flask, followed by argon replacement. 60 ml of dry tetrahydrofuran was added, and a solution of 2.33 g of cesium hydroxide monohydrate in 40 ml of methanol was added and stirred at room temperature for 30 minutes. 0.5 g of zinc chloride was added thereto and stirred for 20 minutes, and 1.23 g of tetrabutylammonium bromide was added and stirred for 30 minutes. Thereafter, the resulting reaction mixture was concentrated under a vacuum, followed by argon replacement. 60 ml of dry tetrahydrofuran was added, followed by cooling to −78° C. Then, 23 ml of acetic acid was added thereto, the temperature was increased to −25° C. with stirring, 1.9 g of 1,1'-thiocarbonyldiimidazole was added, and the temperature was increased. This was stirred all night. The resulting reaction mixture was mixed with methanol, and the resulting precipitate was filtered out and separated by column chromatography (silica gel, carbon disulfide). It was concentrated by an evaporator, and hexane was added for reprecipitation. A filtration and a vacuum drying were performed to give 0.98 g of a compound (124). The yield was 84.7%.

[Synthesis of Two-Linking Polymer (52)]

0.275 g of the compound (124), 0.102 g of the compound (122), and 12 ml of dry xylene were introduced into a 50-ml eggplant flask. 40 ml of dry tetrahydrofuran was added, and a solution of cesium hydroxide (0.37 g) in methanol (20 ml) was added thereto and stirred at room temperature for 30 minutes. Thereafter, 0.1 ml of diiodomethane was added and stirred for 2 hours. The resulting reaction mixture was developed in methanol, filtered, washed with water and methanol, and vacuum dried to give 0.105 g of a two-linking polymer (52). An IR confirmed the presence of the two-linking polymer (52). The yield was 33%.

IR (KBr) 2913, 1504, 1453, 1427 $cm^{-1}$

An X-ray diffraction analysis of the two-linking polymer (52) showed a diffraction pattern derived from the two-linking polymer (52), thereby confirming that the two-linking polymer (52) was crystalline. The X-ray diffraction analysis was performed using Cu—Kα radiation as the incident X-ray according to the 2θ/θ method in a measurement angle range of 1° to 34° (2θ) at a scanning speed of 1°/min.

(2) Production of Power Storage Device

A coin-shaped power storage device was produced in the same manner as in Example 1 except for the use of the two-linking polymer (52).

Example 28

(1) Preparation of Electrode Active Material

A two-linking polymer (56) was synthesized by the following synthesis process.

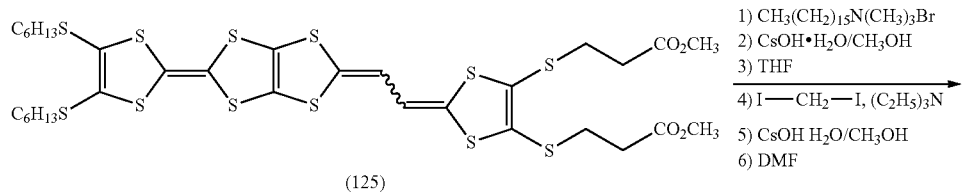

(125)

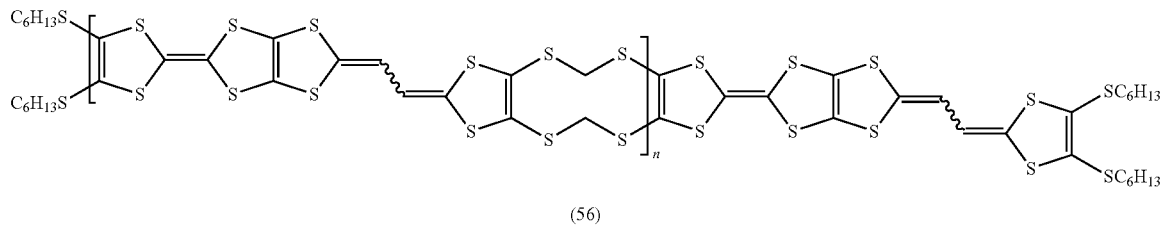

(56)

[Synthesis of Two-Linking Polymer (56)]

81 mg of a derivative (125) of a condensation product of TTF and EBDT, 195 mg of hexadecyltrimethylammonium bromide, and 60 ml of tetrahydrofuran (THF) were introduced into a 100-ml eggplant flask replaced with argon. Further, a methanol solution of 30 mg of cesium hydroxide monohydrate was added and stirred for 20 minutes. Subsequently, 72 μl of diiodomethane, 3 ml of triethylamine, and 20 ml of dimethylformamide (DMF) were added, and stirred at room temperature for 2 hours. The resulting reaction mixture was mixed with a methanol solution of 30 mg of cesium hydroxide monohydrate and stirred for 1 hour. Further, the methanol solution of 30 mg of cesium hydroxide monohydrate was added and stirred for 1 hour. The resulting reaction mixture was filtered to isolate a solid, and the solid was washed with water and methanol and vacuum dried to give 51.8 mg of a powder.

An elemental analysis confirmed that the powder was the two-linking polymer (56). Also, a GPC confirmed that the two-linking polymer (56) had a molecular weight of 22000 in terms of polystyrene standard and was approximately a 46-mer (n=approximately 45).

Elemental analysis: C31. 14, H2. 14

(2) Production of Power Storage Device

A coin-shaped power storage device was produced in the same manner as in Example 1 except for the use of the two-linking polymer (56).

Example 29

(1) Preparation of Electrode Active Material

A polymer (62), comprising an irregularly-linking polymer (4a) of Table 11 wherein R=S(CH$_2$)$_2$COOC$_2$H$_5$, was synthesized by the following synthesis process. The polymer (62) has the one-linking unit, two-linking unit and end group illustrated in Table 12.

TABLE 12

| | Polymer (62) |
|---|---|
| One-linking unit | C$_2$H$_5$OOC(H$_2$C)$_2$S—[structure]—S(CH$_2$)$_2$COOC$_2$H$_5$, <br> *—[structure]—S(CH$_2$)$_2$COOC$_2$H$_5$ |
| Two-linking unit | *—[structure]—*, <br> C$_2$H$_5$OOC(H$_2$C)$_2$S—[structure]—* |
| End group | C$_2$H$_5$OOC(H$_2$C)$_2$S—[structure]—S(CH$_2$)$_2$COOC$_2$H$_5$, <br> C$_2$H$_5$OOC(H$_2$C)$_2$S—[structure]—* <br> C$_2$H$_5$OOC(H$_2$C)$_2$S—[structure]—* |

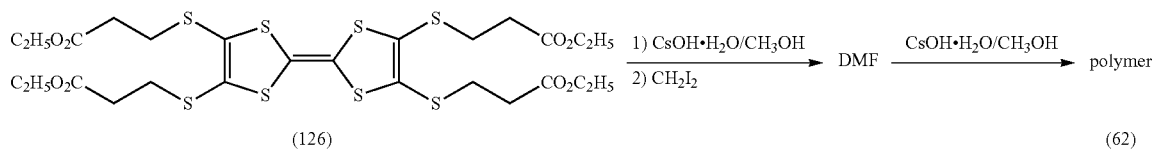

(126)          (62)

[Synthesis of Irregularly-Linking Polymer (62)]

103 mg of a TTF composite derivative (126) and 15 ml of dimethylformamide (DMF) were introduced into a 50-ml eggplant flask replaced with argon. Further, a methanol solution of 55.4 mg of cesium hydroxide monohydrate was added and stirred for 30 minutes. Subsequently, 243 ml of diiodomethane was added and stirred at room temperature for 2 hours. Further, the methanol solution of 55.4 mg of cesium hydroxide monohydrate was added and stirred for 1 hour. The resulting reaction mixture was filtered to isolate a solid, and the solid was washed with water and methanol and vacuum dried to give 29.2 mg of a powder.

An NMR and an elemental analysis confirmed that the powder was the irregularly-linking polymer (62). The elemental analysis confirmed that the ratio of each of the one-linking unit and the two-linking unit in the irregularly-linking polymer (62) was approximately 50 mol %. Also, a GPC confirmed that the irregularly-linking polymer (62) had a molecular weight of 22000 in terms of polystyrene standard, and was an approximately 46-mer (n=approximately 45).

Elemental analysis: S; 64.00

$^1$H-NMR (270 Hz, CDCl$_3$): 1.28, 2.68, 3.07, 4.15

Comparative Example 1

(1) Preparation of Positive Electrode Active Material

An EBDT derivative of the following chemical structural formula comprising one EBDT skeleton was synthesized. The EBDT derivative was synthesized according to the method described in Tetrahedron Letters, vol. 33, 1373 (1992).

[Chem. 46]

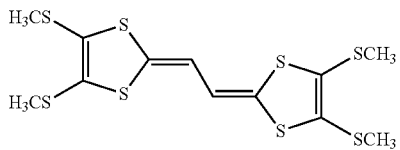

(2) Production of Power Storage Device

A coin-shaped power storage device was produced in the same manner as in Example 1 except for the use of the EBDT derivative.

Comparative Example 2

(1) Preparation of Positive Electrode Active Material

An EBDT/TTF derivative of the following chemical structural formula comprising a fused skeleton of one EBDT and one TTF was synthesized. The EBDT/TTF derivative was synthesized by the method described in J. Master. Chem., 1995, 5(10), 1571-1579.

IR (KBr) 1507, 1492 cm$^{-1}$

[Chem. 47]

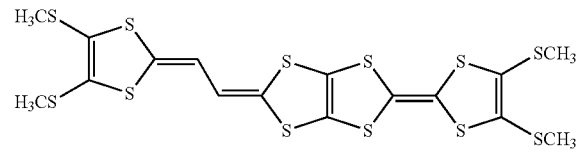

(2) Production of Power Storage Device

A coin-shaped power storage device was produced in the same manner as in Example 1 except for the use of the EBDT/TTF derivative.

Comparative Example 3

(1) Preparation of Electrode Active Material

An X-ray diffraction analysis of a TTF derivative (trade name: tetrakis(methylthio)tetrathiafulvalene, available from Tokyo Chemical Industry Co., Ltd.) of the following chemical structural formula comprising one TTF skeleton showed a diffraction pattern derived from the TTF derivative, thereby confirming that the TTF derivative was crystalline. The X-ray diffraction analysis was performed using Cu—Kα radiation as the incident X-ray according to the 2θ/θ method in a measurement angle range of 1° to 34° (2θ) at a scanning speed of 1°/min.

[Chem. 48]

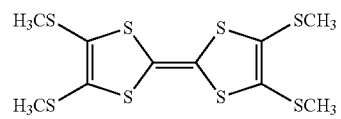

(2) Production of Power Storage Device

A coin-shaped power storage device was produced in the same manner as in Example 1 except for the use of the TTF derivative.

Comparative Example 4

(1) Preparation of Electrode Active Material

A TTP derivative of the following chemical structural formula comprising a fused skeleton of two TTFs was synthesized. The TTP derivative was synthesized by the method described in Chemistry Letters, p 2324, 1992.

[Chem. 49]

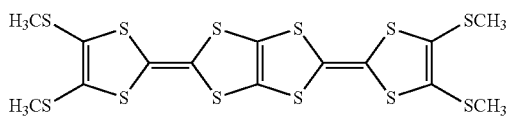

An X-ray diffraction analysis of the TTP derivative showed a diffraction pattern derived from the TTP derivative, thereby confirming that the TTP derivative was crystalline. The X-ray diffraction analysis was performed using Cu—Kα radiation as the incident X-ray according to the 2θ/θ method in a measurement angle range of 1° to 34° (2θ) at a scanning speed of 1°/min.

(2) Production of Power Storage Device

A coin-shaped power storage device was produced in the same manner as in Example 1 except for the use of the TTP derivative.

Test Example 1

The performances of the electrode active materials having EBDT skeletons were compared. The coin-shaped power storage devices of Example 1 (a dimer of an EBDT derivative), Example 15 (a trimer of an EBDT derivative), and Comparative Example 1 (a derivative of an EBDT monomer) were subjected to a constant-current charge/discharge cycle test of 10 cycles at a current of 0.2 mA and in the voltage range of 3.0 to 3.75 V. The test results (charge/discharge curves) of Examples 1 and 15 are shown in FIG. 2 and FIG. 3, respectively.

For Examples 2 to 4 (dimers of EBDT derivatives) and Examples 5, 6, and 16 (multimers of EBDT derivatives), the same charge/discharge cycle test was also performed.

Figure 2:
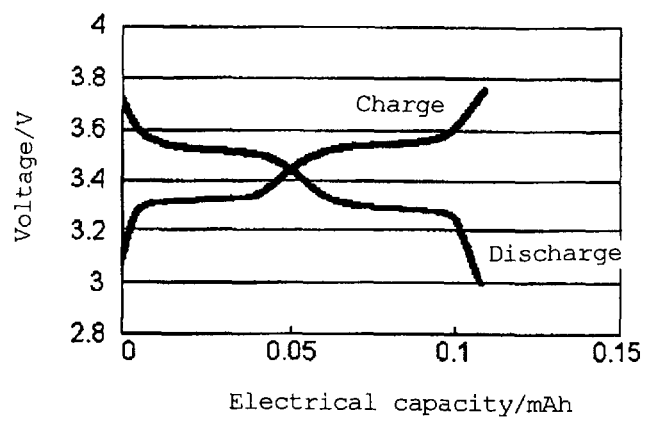
FIG. 2 is a graph showing the relationship between the battery voltage and the electrical capacity at the 10th cycle in a charge/discharge test of a power storage device of Example 1.
Figure 3:
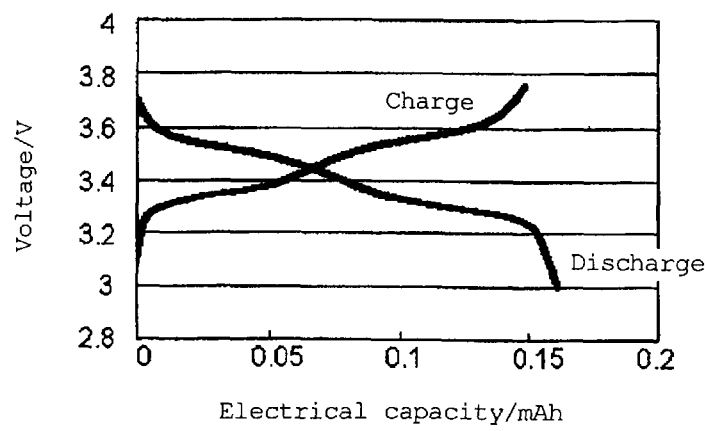
FIG. 3 is a graph showing the relationship between the battery voltage and the electrical capacity at the 10th cycle in a charge/discharge test of a power storage device of Example 15.

FIG. 2 is a graph showing the relationship between the battery voltage and the electrical capacity at the 10th cycle in the charge/discharge test of the power storage device of Example 1. FIG. 2 confirmed that the power storage device of Example 1 was capable of reversible charge/discharge behavior at a discharge voltage of approximately 3.3 to 3.5 V. FIG. 3 is a graph showing the relationship between the battery voltage and the electrical capacity at the 10th cycle in the charge/discharge test of the power storage device of Example 15. FIG. 3 confirmed that the power storage device of Example 15 was capable of reversible charge/discharge behavior at a discharge voltage of approximately 3.3 to 3.5 V.

Also, using the power storage devices of Examples 1 to 6 and 15 to 16 and Comparative Example 1, the discharge capacity retention rate after 10 cycles was obtained. The discharge capacity retention rate after 10 cycles is the percentage of the discharge capacity at the $10^{th}$ cycle relative to the discharge capacity at the $1^{st}$ cycle. The results are shown in Table 13.

TABLE 13

| | Electrode Active Material | Number of reaction skeletons in molecule | Discharge capacity retention rate after 10 cycles [%] |
|---|---|---|---|
| Example 1 | One-Linking Polymer (11) | 2 | 38% |
| Example 2 | One-Linking Polymer (12) | 2 | 65% |
| Example 3 | One-Linking Polymer (13) | 2 | 84% |
| Example 4 | One-Linking Polymer (14) | 2 | 60% |
| Example 5 | One-Linking Polymer (19) | 39 | 97% |
| Example 6 | One-Linking Polymer (20) | 17 | 95% |
| Example 15 | One-Linking Polymer (34) | 3 | 52% |
| Example 16 | One-Linking Polymer (37) | 6 | 96% |
| Comp. Example 1 | Derivative of EBDT monomer | 1 | 17% |

Table 13 clearly shows that the power storage devices of Examples have significantly high discharge capacity retention rates after 10 cycles (hereinafter referred to as simply "discharge capacity retention rates"), compared with the power storage device of Comparative Example 1. This indicates that the one-linking polymers are capable of reversible charge/discharge behavior and are useful as electrode active materials. After the completion of the test, the battery cells were disassembled, and it was found that particularly in the battery of Comparative Example, the electrolyte was significantly colored probably due to the dissolution of the active material, and that in the batteries of Examples, the coloring of the electrolyte was significantly suppressed. This strongly suggested that a large factor causing a decrease in discharge capacity was dissolution of the electrode active material into the electrolyte.

The electrode active materials of Examples 1 and 15 are derivatives of a dimer and a trimer of an EBDT skeleton, respectively. The electrode active material of Comparative Example 1 is a derivative of a monomer of an EBDT skeleton. Since all of them are EBDT derivatives and basically have similar molecular structures, their molecules are thought to be capable of charge/discharge. However, they were found to be significantly different in their functions as the electrode active materials. One possible cause is a difference in the solubility into the electrolyte upon charge/discharge resulting from the difference in molecular structure. It is thought that although the electrode active materials of Examples 1 and 15 are a dimer and a trimer, respectively, their solubility into the electrolyte was significantly decreased due to multimerization, thereby resulting in a difference in discharge capacity retention rate.

With respect to the structure of the S-A-S portion, a comparison of Examples 1 to 3 in Table 13 clearly shows the following. That is, rather than linking by —(CH$_2$)$_m$— (where m is an integer of 1 or more, and hereinafter the same), linking by —(CH$_2$)$_m$—(C$_6$H$_4$)— (CH$_2$)$_m$— or —(CH$_2$)$_m$— (C=O)—(CH$_2$)$_m$— is more effective in decreasing the dissolution into the electrolyte even when the degree of polymerization is low such that the number of the basic skeletons is approximately 2. As a result, the discharge capacity retention rate was significantly heightened to 60% or more. Also, with respect to the S-A-S portion, such molecular structures as —(CH$_2$)$_m$—(C$_6$H$_4$)—(CH$_2$)$_m$— and —(CH$_2$)$_m$—(C=O)—(CH$_2$)$_m$— are thought to have a three-dimensional structure that increases the interaction between the molecules. The functional groups at the end are also thought to produce a similar effect.

In a comparison between Example 2 and Example 3, the polymer (Example 3) having an ethylenedithio group (—S—(CH$_2$)$_2$—S—) at the end of the molecule had a discharge capacity retention rate of 84%, which is significantly higher than that of the polymer (Example 2) having a methylthio group at the end of the molecule. This is probably due to the following reason. That is, in the case of the polymer of Example 3, since the ethylenedithio group is bonded to the end, the molecular structure becomes somewhat flat, and the conjugated π electron cloud present in the direction perpendicular to the flat molecule becomes abundant. As a result, a strong interaction, i.e., an intermolecular attraction, acts between the skeletons, thereby increasing the effect of suppressing the dissolution of the polymer into the electrolyte.

In the polymers of the invention, as the number of repetition of the reaction skeletons linked by the divalent groups —S-A-S— increased, the discharge capacity retention rate increased. Specifically, when the number of repetition of the reaction skeleton was 2 or more, the discharge capacity retention rate was 38% or more, and when the number of repetition of the reaction skeleton was 3, the discharge capacity retention rate was 52%. Also, the polymer with a number of repetition of the reaction skeleton of 6 had a discharge capacity retention rate of 96%, showing a particularly good effect. Further, the polymer with a high number of repetition of the reaction skeleton of approximately 17 or more had a discharge capacity retention rate of 95% or more, showing a very good cycle characteristic.

With respect to the angle at which the reaction skeletons are linked by the divalent group —S-A-S—, the following results were obtained. Of the polymers with a low number of repetition of the reaction skeleton of 2 or 3, the polymers with the reaction skeletons linked in the form of a chain (hereinafter referred to as "chain polymers") were more effective in suppressing the dissolution into the electrolyte than the polymers with the reaction skeletons linked in a zigzag (hereinafter referred to as "zigzag polymers"). Of the zigzag polymers, the polymer with a number of repetition of the reaction skeleton of 6 had a discharge capacity retention rate of 96%, showing a very good cycle characteristic.

The polymers of Examples 5 and 6 exhibited good cycle characteristics although they were not subjected to a complicated purification step for synthesis. Generally, there is a variation in the molecular weight of polymers immediately after synthesis, and a complicated purification step may become necessary to remove polymers with a low molecular weight. However, since the polymers of the invention are resistant to dissolution into the electrolyte even when the number of repetition of the basic skeleton is approximately 2, even if polymers with a low molecular weight are included, they do not always need to be removed, and hence, the polymers of the invention can be easily synthesized.

It can be understood that the power storage device of Example 15 has a higher discharge capacity retention rate and a better cycle characteristic than the power storage device of Example 1. The only difference between the polymer of Example 1 and the polymer of Example 15 is that the number of repetition of the reaction skeleton is different by "1", but linking one more reaction skeleton by the divalent group —S—$CH_2$—S— is thought to have caused a large difference in the dissolution into the electrolyte.

Test Example 2

The performances of the polymers having TTF skeletons as electrode active materials were compared. The coin-shaped power storage devices of Examples 7 to 9 (dimers of TTF derivatives), Examples 10 to 12 (multimers of TTF derivatives), Example 17 (a trimer of a TTF derivative), and Comparative Example 3 (a derivative of a TTF monomer) were subjected to a constant-current charge/discharge cycle test of 10 cycles at a current of 0.2 mA and in the voltage range of 3.0 to 4.0 V. It was confirmed that all of the power storage devices were capable of reversible charge/discharge as in the results of the EBDT skeletons of Test Example 1. The discharge capacity retention rates of these power storage devices were determined in the same manner as in Test Example 1. The discharge capacity retention rate is the percentage of the discharge capacity at the $10^{th}$ cycle relative to the discharge capacity at the $1^{st}$ cycle. The results are shown in Table 14.

TABLE 14

|  | Electrode active material | Number of reaction skeletons in molecule | Discharge capacity retention rate after 10 cycles [%] |
| --- | --- | --- | --- |
| Example 7 | One-linking polymer (21) | 2 | 87% |
| Example 8 | One-linking polymer (22) | 2 | 74% |
| Example 9 | One-linking polymer (23) | 2 | 87% |
| Example 10 | One-linking polymer (24) | 80 | 95% |
| Example 11 | One-linking polymer (25) | 50 | 96% |

TABLE 14-continued

|  | Electrode active material | Number of reaction skeletons in molecule | Discharge capacity retention rate after 10 cycles [%] |
| --- | --- | --- | --- |
| Example 12 | One-linking polymer (26) | 10 | 96% |
| Example 17 | One-linking polymer (38) | 3 | 48% |
| Comp. Example 3 | Derivative of TTF monomer | 1 | 5% |

Table 14 clearly indicates that the power storage devices of Examples have significantly high discharge capacity retention rates, compared with the power storage device of Comparative Example 1, in the same manner as the EBDT reaction skeletons. Also, with respect to the divalent group S-A-S, a comparison of Examples 7 to 9 in Table 14 clearly shows the following. In the case of the polymers whose reaction skeletons are linked by —$(CH_2)_m$—, —$(CH_2)_m$—$(C_6H_4)$—$(CH_2)_m$—, and —$(CH_2)_m$—(C=O)—$(CH_2)_m$—, even when the number of repetition was as low as approximately 2, the dissolution into the electrolyte was decreased, so that the discharge capacity retention rate was significantly heightened to 74% or more. This is probably because the TTF molecule has a flat structure and is abundant in conjugated π electron cloud present in the direction perpendicular to the flat molecule. As a result, a strong interaction, i.e., an intermolecular attraction, acts between the reaction skeletons, thereby suppressing the dissolution of the polymer into the electrolyte.

Also, as the number of repetition of the reaction skeletons linked by the divalent group —S-A-S— in the polymer increases, the discharge capacity retention rate of the polymer increases. Specifically, the polymers with a number of repetition of the reaction skeleton of 2 or more had high discharge capacity retention rates of 74% or more. Also, the polymer with a number of repetition of the reaction skeleton of 10 had a particularly high discharge capacity retention rate of 96%. The polymers with a number of repetition of the reaction skeleton of approximately 50 or more also had discharge capacity retention rates of 95% or more, showing very good cycle characteristics.

With respect to the angle at which the reaction skeletons are linked by the divalent group —S-A-S—, the following results were obtained. Of the polymers with a low number of repetition of the reaction skeleton of 2 or 3, the chain polymers were more effective in suppressing the dissolution into the electrolyte than the zigzag polymer. The zigzag polymer with a number of repetition of the reaction skeleton of 3 had a discharge capacity retention rate of 48%, while the chain polymers with a number of repetition of the reaction skeleton of 2 or more had discharge capacity retention rates of 74% or more, showing very good cycle characteristics.

The polymers of Examples 10 to 12 exhibited good cycle characteristics although they were not subjected to a complicated purification step for synthesis. Generally, there is a variation in the molecular weight of polymers immediately after synthesis, and a complicated purification step may become necessary to remove polymers having a low number of repetition of a reaction skeleton. However, since the polymers used in the invention are resistant to dissolution into the electrolyte even when the number of repetition of the basic skeleton is approximately 2, even if polymers having a low number of repetition of a reaction skeleton are included, they do not always need to be removed, so the polymers of the invention can be easily synthesized.

Test Example 3

The performances of the polymers having a fused skeleton of EBDT and TTF and a TTP skeleton that is a fused skeleton of two TTFs as electrode active materials were compared. The coin-shaped power storage devices of Example 13 (a dimer of a derivative of a condensation product of EBDT and TTF), Example 18 (a multimer of a derivative of a condensation product of EBDT and TTF), and Comparative Example 2 (a monomer of a derivative of a condensation product of EBDT and TTF) were subjected to a constant-current charge/discharge cycle test of 10 cycles at a current of 0.2 mA and in the voltage range of 3.0 to 4.0 V, in the same manner as in Test Example 1. The coin-shaped power storage devices of Example 14 (a dimer of a TTP derivative) and Comparative Example 4 (a monomer of a TTP derivative) were also subjected to the same test.

It should be noted that since the power storage devices of Examples 13, 14, and 18 and Comparative Examples 2 and 4 cannot be charged completely in the voltage range of the power storage device of Example 1, the upper limit of the voltage range was changed from 3.75 V to 4.0 V in performing the charge/discharge cycle test.

Figure 4:
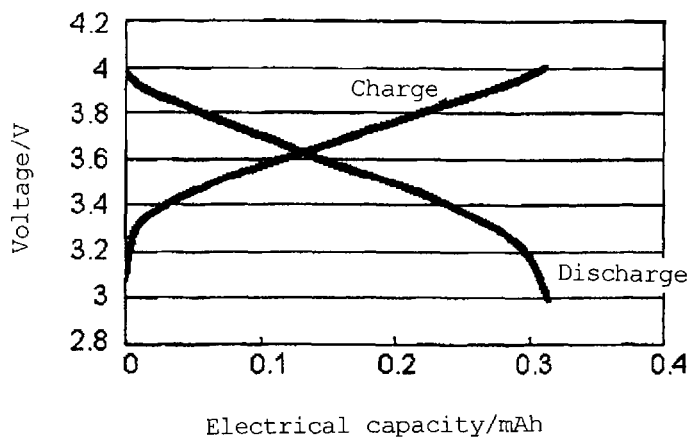
FIG. 4 is a graph showing the relationship between the battery voltage and the electrical capacity at the 10th cycle in a charge/discharge test of a power storage device of Example 13.

The test results (charge/discharge curves) of Example 13 are shown in FIG. 4. FIG. 4 is a graph showing the relationship between the battery voltage and the electrical capacity at the 10th cycle in the charge/discharge test of the power storage device of Example 13. FIG. 4 confirmed that the power storage device of Example 13 was capable of reversible charge/discharge behavior at a discharge voltage of approximately 3.3 to 3.8 V.

Also, using the power storage devices of Examples 13, 14, and 18 and Comparative Examples 2 and 4, the discharge capacity retention rate was determined in the same manner as in Test Example 1. The results are shown in Table 15.

TABLE 15

| | Electrode active material | Number of reaction skeletons in molecule | Discharge capacity retention rate after 10 cycles [%] |
|---|---|---|---|
| Example 13 | One-linking polymer (28) | 2 | 79% |
| Example 14 | One-linking polymer (32) | 2 | 87% |
| Example 18 | One-linking polymer (39) | 68 | 94% |
| Comp. Example 2 | Monomer of derivative of condensation product of EBDT and TTF | 1 | 51% |
| Comp. Example 4 | Monomer of TTP derivative | 1 | 17% |

The fused skeletons of EBDT and TTF in Table 15 showed the same tendency as that of the results of the EBDT skeletons shown in Table 13.

The power storage device of Example 13 has a high discharge capacity retention rate. A comparison between Example 13 and Comparative Example 2 suggests that the dissolution of the fused skeleton of EBDT and TTF into the electrolyte is smaller than the dissolution of the EBDT skeleton into the electrolyte. This suggests that the use of the polymer of Example 13 including the dimer of the derivative of the fused skeleton of EBDT and TTF as the electrode active material improved the discharge capacity retention rate significantly.

Further, multimerization by the divalent group —S—CH$_2$—S— is thought to have caused a larger difference in the dissolution into the electrolyte. It was confirmed that in Example 18 having an increased number of skeletons, the discharge capacity retention rate was further heightened. Further, a comparison between Example 14 and Comparative Example 4 clearly indicates that the results of the TTP skeletons are similar to those of the fused skeletons of EBDT and TTF.

Test Example 4

Figure 5:
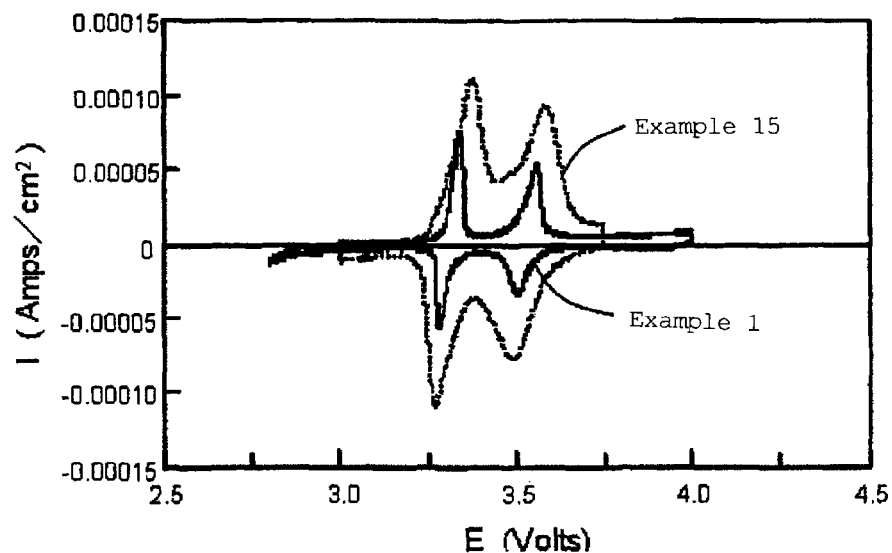
FIG. 5 shows cyclic voltammograms of the power storage devices of Example 1 and Example 15.
Figure 6:
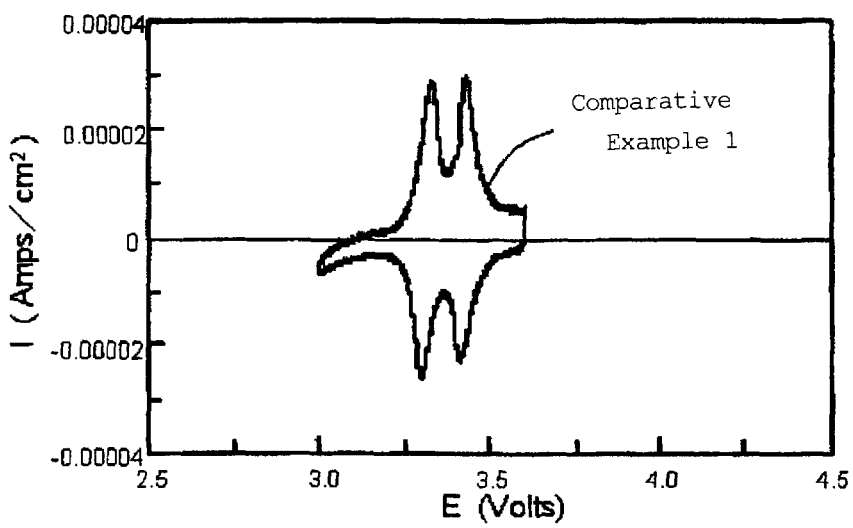
FIG. 6 is a cyclic voltammogram of a power storage device of Comparative Example 1.

Using the power storage devices of Examples 1 and 15 and Comparative Example 1, cyclic voltammogram measurements were made to compare their charge/discharge reaction potentials. The cyclic voltammogram measurements were made under the following conditions. In the power storage devices of Examples 1 and 15, the voltage range was set to 2.8 V to 4.0 V, and the scan speed was set to 0.1 mV/sec. In the power storage device of Comparative Example 1, the voltage range was set to 3.0 V to 3.7 V, and the scan speed was set to 0.1 mV/sec. The results are shown in FIG. 5 and FIG. 6. FIG. 5 shows the cyclic voltammograms of the power storage devices of Example 1 and Example 15. FIG. 6 is a cyclic voltammogram of the power storage device of Comparative Example 1.

FIG. 6 confirms that the power storage device of Comparative Example 1 is capable of highly reversible oxidation-reduction reactions in two stages of reaction potentials of 3.3 V and 3.4 V. FIG. 5 shows the results of Example 1 and Example 15 that use, as electrode active materials, polymers prepared by multimerizing the EBDT skeleton contained in the EBDT derivative of Comparative Example 1. FIG. 5 confirmed that the power storage devices of both Example 1 and Example 15 were capable of highly reversible two-stage oxidation-reduction reactions. Also, the two-stage reaction potentials were 3.3 V and 3.5 V, and the voltage became 0.1 V higher than that of the power storage device of Comparative Example 1, but there was no change caused by the increase in the degree of multimerization (the degree of polymerization).

It was also confirmed that the reaction voltages of the polymers of Examples other than Examples 1 and 15 were higher than those of Comparative Examples 1 to 4 by approximately 0.1 V. The fact that the reaction potentials of the polymers whose reaction skeletons are linked by the divalent group —S-A-S— are higher than those of the monomers by as much as 0.1 V indicates that the electrode active materials of the invention including the polymers of Examples not only improve the cycle characteristics of the batteries but also heighten the energy density. This is probably due to the following synergistic effect. That is, when one of the reaction skeletons was oxidized, it was influenced by the adjacent reaction skeleton linked by the divalent group —S-A-S, and thus, their reaction potentials were both heightened.

These results indicate that the polymers of this embodiment are significantly resistant to dissolution into the electrolyte without impairing the good characteristics of the reaction skeletons themselves as the electrode active materials, thereby improving the cycle characteristics. Also, they indicate that the polymers of this embodiment act as electrode active materials and have high capacities and high voltages as well as good cycle characteristics.

As described above, by designing a one-linking polymer in which reaction skeletons such as EBDT skeletons or fused skeletons of EBDT and TTF are multimerized by the divalent group —S-A-S—, and using it as an electrode active material, it is possible to provide a power storage device with good cycle characteristics and a high energy density. Also, the addition of a functional group to the one-linking polymer makes it possible to further improve the cycle characteristics, heighten the discharge voltage, etc.

Test Example 5

The coin-shaped power storage devices of Example 19 and Comparative Example 1 were subjected to a constant-current charge/discharge cycle test of 10 cycles at a current of 0.2 mA and in a predetermined voltage range. The voltage range of the test of each power storage device was 3.0 V to 3.8 V.

Figure 7:
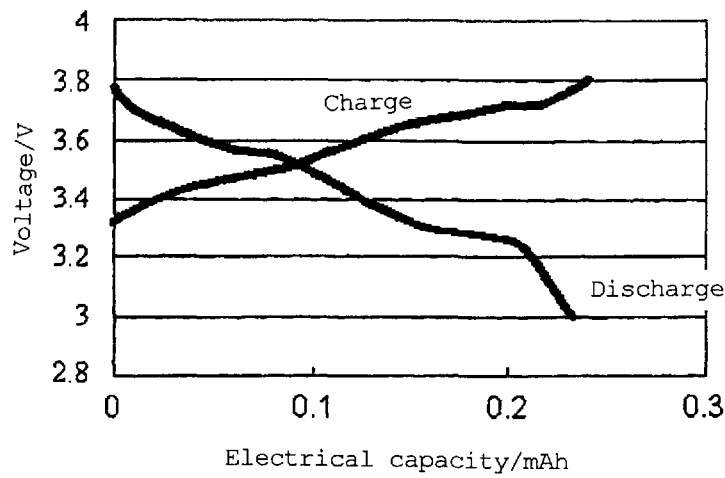
FIG. 7 is a graph showing the relationship between the battery voltage and the electrical capacity at the 10th cycle in a charge/discharge test of a power storage device of Example 19.

It was confirmed that the power storage devices of Example 19 and Comparative Example 1 were capable of reversible charge/discharge behavior. The test results of the power storage device of Example 19 are shown in FIG. 7. FIG. 7 is a graph showing the relationship between the battery voltage and the electrical capacity at the 10th cycle in the charge/discharge test of the power storage device of Example 19. FIG. 7 confirmed that the power storage device of Example 19 had a discharge voltage of approximately 3.3 to 3.6 V and was capable of reversible charge/discharge behavior. Further, using the power storage devices of Examples 19, 20, and 22 and Comparative Example 1, the discharge capacity retention rate was determined in the same manner as in Test Example 1. The results are shown in Table 16.

TABLE 16

| | Electrode active material | Number of reaction skeletons in molecule | Discharge capacity retention rate after 10 cycles [%] |
|---|---|---|---|
| Example 19 | Two-linking polymer (40) | 2 | 82% |
| Example 20 | Two-linking polymer (41) | 2 | 89% |
| Example 22 | Two-linking polymer (44) | 85 | 100% |
| Comp. Example 1 | Derivative of EBDT monomer | 1 | 17% |

In the power storage devices of Examples 19 to 20 and 22 and Comparative Example 1, polymers including EBDT skeletons are used as electrode active materials. In the polymer of Example 19, EBDT skeletons are linked by two divalent groups —S—CH$_2$—S—. In the polymers of Examples 20 and 22, EBDT skeletons are linked by two divalent groups —S—CH$_2$—(C$_6$H$_4$)—CH$_2$—S—. In Comparative Example 1, a derivative of a monomer of an EBDT skeleton is used as an electrode active material.

Table 16 indicates that the electrode active materials of Examples can improve the cycle characteristics of the power storage devices significantly, compared with the electrode active material of Comparative Example 1. It was therefore confirmed that the electrode active materials including a two-linking polymer were effective. The two-linking polymers can improve the cycle characteristics of the power storage devices significantly even when the degree of polymerization is low with the number of repetition of the reaction skeleton being approximately 2, compared with the one-linking polymers. This is probably for the following reasons. The EBDT skeletons have a flat molecular structure and are abundant in conjugated π electron cloud present in the direction perpendicular to the flat molecule. Thus, a strong interaction, i.e., an intermolecular attraction, acts between the reaction skeletons. As a result, the effect of suppressing the dissolution of the polymer into the electrolyte was increased. Also, the polymer with a high number of repetition of the reaction skeleton of approximately 85 produces a more prominent effect.

Test Example 6

The coin-shaped power storage devices of Example 23 and Comparative Example 3 were subjected to a constant-current charge/discharge cycle test of 10 cycles at a current of 0.2 mA and in a predetermined voltage range. The voltage range of the test was 3.0 V to 4.1 V for the power storage device of Example 23 and 3.0 V to 3.8 V for the power storage device of Comparative Example 3.

Figure 8:
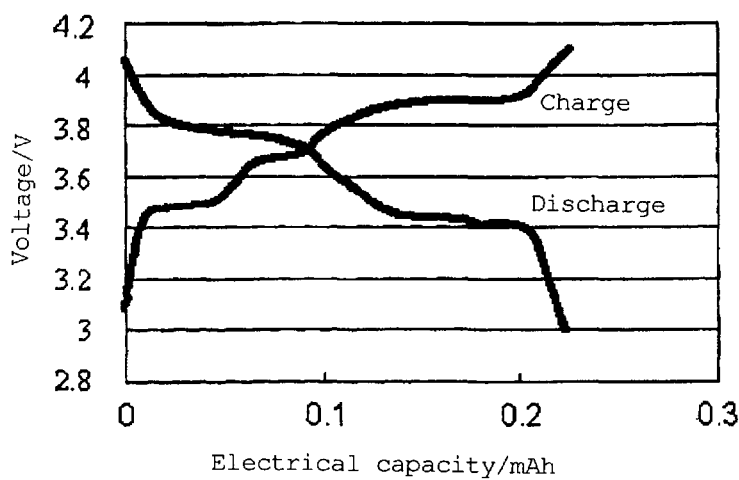
FIG. 8 is a graph showing the relationship between the battery voltage and the electrical capacity at the 10th cycle in a charge/discharge test of a power storage device of Example 23.

It was confirmed that the power storage devices of Example 23 and Comparative Example 3 were capable of reversible charge/discharge behavior. The test results of the power storage device of Example 23 are shown in FIG. 8. FIG. 8 is a graph showing the relationship between the battery voltage and the electrical capacity at the 10th cycle in the charge/discharge test of the power storage device of Example 23. FIG. 8 confirmed that the power storage device of Example 23 had a discharge voltage of approximately 3.4 to 3.8 V and was capable of reversible charge/discharge behavior. Further, using the power storage devices of Examples 23 to 26 and 29 and Comparative Example 3, the discharge capacity retention rate after 10 cycles was determined in the same manner as in Test Example 1. The results are shown in Table 17.

TABLE 17

| | Electrode active material | Number of reaction skeletons in molecule | Discharge capacity retention rate after 10 cycles [%] |
|---|---|---|---|
| Example 23 | Two-linking polymer (45) | 2 | 72% |
| Example 24 | Two-linking polymer (48) | 3 | 74% |
| Example 25 | Two-linking polymer (49) | 2 | 91% |
| Example 26 | Two-linking polymer (50) | 46 | 100% |
| Example 29 | Irregularly-linking polymer (62) | 45 | 100% |
| Comp. Example 3 | Derivative of TTF monomer | 1 | 5% |

In Examples 24 and 26, two-linking polymers (a trimer and a multimer) in which TTF skeletons were linked by two divalent groups —S—CH$_2$—S— were used as electrode active materials. In Example 25, a two-linking polymer (a dimer) in which TTF skeletons were linked by two divalent groups (—S—CH$_2$—(C$_6$H$_4$)—CH$_2$—S—) was used as an electrode active material. In Comparative Example 3, a derivative of a TTF monomer was used as an electrode active material.

Table 17 indicates that the electrode active materials of Examples 23 to 26 can improve the cycle characteristics of the power storage devices significantly, compared with the electrode active material of Comparative Example 3. Thus, it was confirmed that the electrode active materials including a two-linking polymer were effective. It was also confirmed that the power storage device using the electrode active material including the irregularly-linking polymer of Example 29 also exhibited a good cycle characteristic. This confirmed that the electrode active material including the irregularly-linking polymer was effective.

Test Example 7

The coin-shaped power storage devices of Example 21 (a dimer of a TTP derivative), Example 27 (a dimer of a derivative of a condensation product of EBDT and TTF), Comparative Example 2 (a monomer of a derivative of a condensation product of EBDT and TTF), and Comparative Example 4 (a monomer of a TTP derivative) were subjected to a constant-current charge/discharge cycle test of 10 cycles at a current of 0.2 mA and in a predetermined voltage range. The voltage range of the test was 3.0 V to 4.2 V for the power storage devices of Examples 21 and 27, and 3.0 V to 4.1 V for the power storage devices of Comparative Examples 2 and 4. As a result, it was confirmed that the power storage devices of Examples 21 and 27 and Comparative Examples 2 and 4 were capable of reversible charge/discharge behavior.

Figure 9:
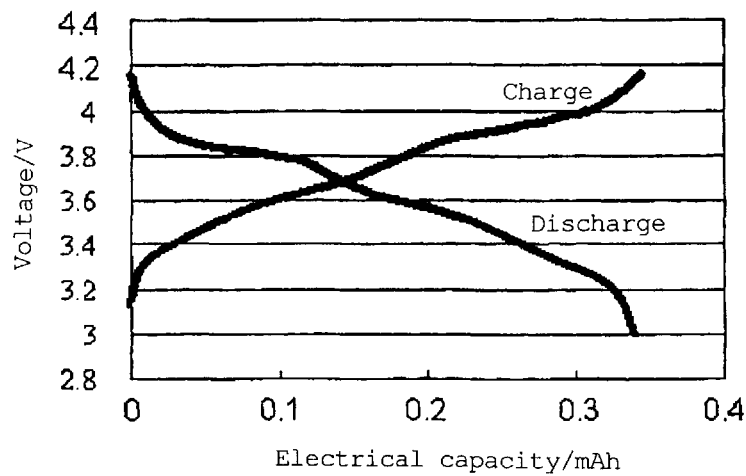
FIG. 9 is a graph showing the relationship between the battery voltage and the electrical capacity at the 10th cycle in a charge/discharge test of a power storage device of Example 27.

The test results of the power storage device of Example 27 are shown in FIG. 9. FIG. 9 is a graph showing the relationship between the battery voltage and the electrical capacity at the 10th cycle in the charge/discharge test of the power storage device of Example 27. FIG. 9 confirmed that the power storage device of Example 27 had a discharge voltage of approximately 3.4 to 3.8 V and was capable of reversible charge/discharge behavior. Further, using the power storage devices of Examples 21 and 27 and Comparative Examples 2 and 4, the discharge capacity retention rate after 10 cycles was determined in the same manner as in Test Example 1. The results are shown in Table 18.

TABLE 18

|  | Electrode active material | Number of reaction skeletons in molecule | Discharge capacity retention rate after 10 cycles [%] |
| --- | --- | --- | --- |
| Example 21 | Two-linking polymer (59) | 2 | 73% |
| Example 27 | Two-linking polymer (52) | 2 | 85% |
| Comp. Example 2 | Monomer of derivative of condensation product of EBDT and TTF | 1 | 51% |
| Comp. Example 4 | Monomer of TTP derivative | 1 | 17% |

In the power storage device of Example 21, a two-linking polymer in which TTP skeletons were linked by two divalent groups —S—$CH_2$—S— was used as an electrode active material. In Comparative Example 4, a derivative of a TTP monomer was used as an electrode active material. Table 18 indicates that the electrode active material of Example 21 can improve the cycle characteristics of the power storage device significantly, compared with the electrode active material of Comparative Example 4.

In the power storage device of Example 27, a two-linking polymer in which two fused skeletons of EBDT and TTF were linked by two divalent groups —S—$CH_2$—S— was used as an electrode active material. In the power storage device of Comparative Example 2, a derivative of a monomer of a fused skeleton of EBDT and TTF was used as an electrode active material. Table 18 indicates that the electrode active material of Example 27 can improve the cycle characteristics of the power storage device significantly, compared with the electrode active material of Comparative Example 2.

Also, after the test, the power storage devices were disassembled and observed, and it was found that in the power storage device of Comparative Example 4 with a low discharge capacity retention rate, the separator and the electrolyte were significantly colored. This suggests that the decrease in discharge capacity retention rate is caused by the dissolution of the active material into the electrolyte.

The respective compounds used as the electrode active materials in Comparative Examples 1 to 4 were crystalline. Also, for example, the respective polymers used as the electrode active materials in Examples 19, 23, and 27 were also crystalline. However, there was a large difference in discharge capacity retention rate. This means that the polymers used in Examples 19, 23, and 27 have a strong intermolecular force acting between the molecules. Probably for this reason, the dissolution into the electrolyte during charge/discharge was suppressed, and the cycle characteristics of the power storage devices were improved.

These results indicate that the polymers provided by the invention act as electrode active materials. Also, the power storage devices including the electrode active materials of the invention have high capacities and high voltages as well as good cycle characteristics.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

INDUSTRIAL APPLICABILITY

The electrode active materials of the invention for power storage devices can be advantageously used as electrode active materials for various power storage devices. The power storage devices of the invention can be used as, for example, primary batteries, secondary batteries, electrochemical capacitors, electrolytic capacitors, sensors, and electrochromic devices. The power storage devices of the invention can be used as main power sources or auxiliary power sources for electronic devices, transportation devices, etc. Examples of electronic devices include personal computers, cellular phones, mobile devices, personal digital assistants (PDAs), portable game machines, and video cameras. Examples of transportation devices include electric vehicles, hybrid electric vehicles, and HEVs. Further, the power storage devices of the invention can also be used as uninterruptible power supplies, etc.

The invention claimed is:
1. A power storage device comprising: a positive electrode; a negative electrode; and an electrolyte that includes a non-aqueous solvent and a supporting salt comprising an anion and a cation dissolved in the non-aqueous solvent, wherein an electrode active material included in at least one of the positive electrode and the negative electrode is an electrode active material comprising a polymer that includes a repeat unit X represented by the following general formula (X) and a repeat unit Y, where the repeat unit X and the repeat unit Y are components of a main chain, adjacent two repeat units Y are linked by one or two repeat units X, and the repeat unit Y is at least one selected from the group consisting of repeat units Y1, Y2, Y3, and Y4 represented by the following general formulae (Y1), (Y2), (Y3), and (Y4), respectively, and wherein the electrode active material does not include a charge transfer complex composed of a fulvalene derivative and iodine,

[Chem. 1]

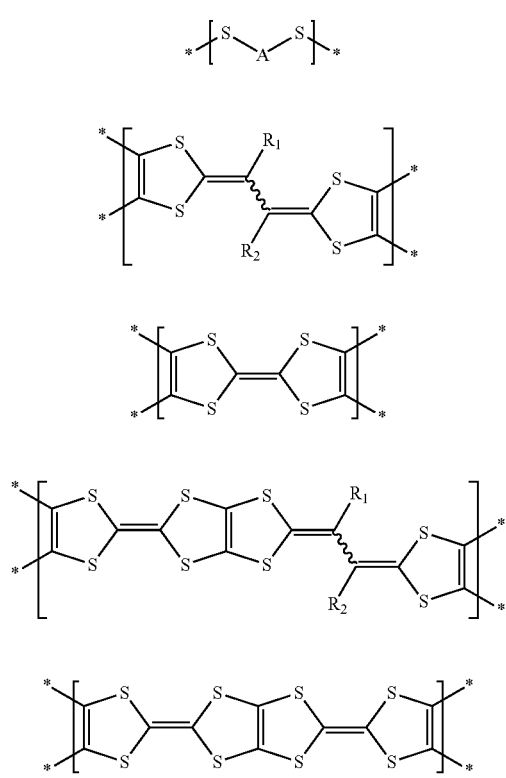

where in the formula (X), A represents a divalent aliphatic group or a divalent group represented by the formula -E-D-E- where D represents a divalent alicyclic group, a divalent aromatic group, or a carbonyl group, and two Es each independently represent a divalent aliphatic group; in the formula (Y1) and the formula (Y3), $R_1$ and $R_2$ each independently represent a hydrogen atom, a fluorine atom, a monovalent aliphatic group, or a monovalent aromatic group; and the monovalent and divalent aliphatic groups, the divalent alicyclic group, and the monovalent and divalent aromatic groups can each independently contain at least one kind of atom selected from the group consisting of halogen atom, nitrogen atom, oxygen atom, sulfur atom, and silicon atom.

2. The power storage device according to claim 1, wherein the repeat unit Y has four bonding sites, at least two of the bonding sites are each bonded to the repeat unit X, and the remaining bonding sites not bonded to the repeat unit X are each bonded to a group —R where R represents a hydrogen atom, a fluorine atom, a monovalent aliphatic group, or a monovalent aromatic group; and the monovalent aliphatic group and the monovalent aromatic group each independently contain at least one kind of atom selected from the group consisting of halogen atom, nitrogen atom, oxygen atom, sulfur atom, and silicon atom.

3. The power storage device according to claim 1, wherein the polymer is a one-linking polymer in which adjacent two repeat units Y are linked by one repeat unit X, and the one-linking polymer includes at least one selected from the group consisting of repeat units Z1, Z2, Z3, and Z4 represented by the following general formulae (Z1), (Z2), (Z3), and (Z4), respectively,

[Chem. 2]

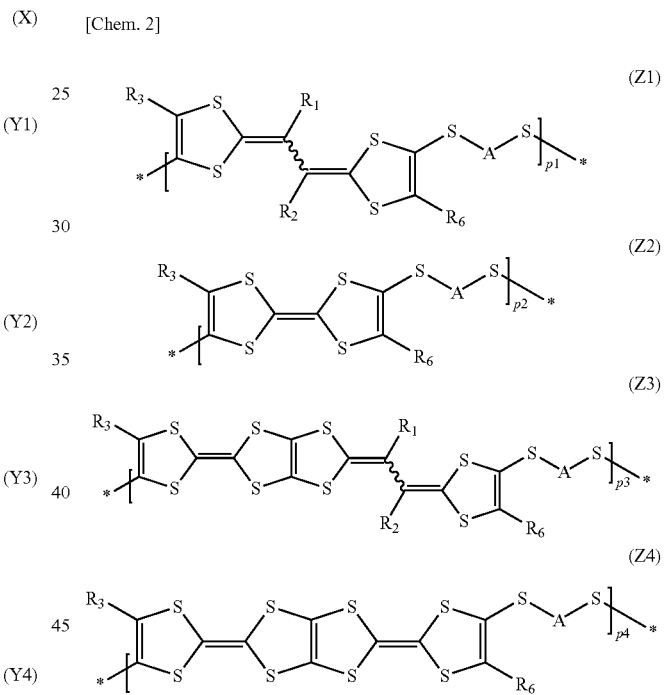

where in the formulae (Z1) to (Z4), A, $R_1$, and $R_2$ are as defined above; $R_3$ and $R_6$ each independently represent a hydrogen atom, a fluorine atom, a monovalent aliphatic group, or a monovalent aromatic group; the monovalent aliphatic group and the monovalent aromatic group can contain at least one kind of atom selected from the group consisting of halogen atom, nitrogen atom, oxygen atom, sulfur atom, and silicon atom; and p1 to p4 each represent the total number of repetition of the repeat units Z1 to Z4 in the one-linking polymer and represent a real number of 2 or more.

4. The power storage device according to claim 1, wherein the polymer is a one-linking polymer (1) in which adjacent two repeat units Y are linked by one repeat unit X, and the one-linking polymer (1) is at least one selected from the group consisting of polymers 1a, 1b, 1c, 1d, 1e, and 1f represented by the following general formulae (1a), (1b), (1c), (1d), (1e), and (1f), respectively,

[Chem. 3]

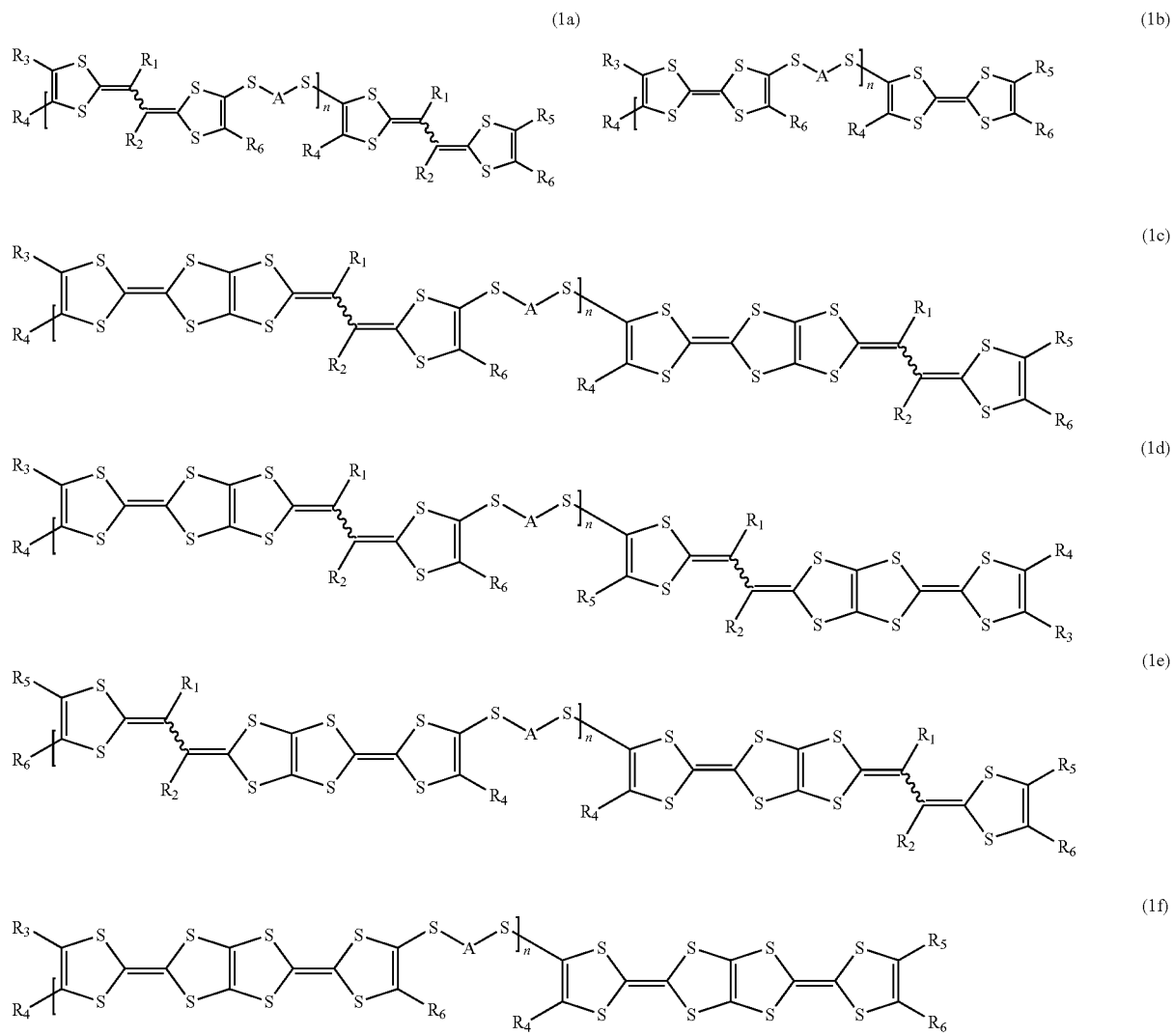

where in the formulas (1a) to (1f), A, $R_1$ and $R_2$ are as defined above; $R_3$ to $R_6$ each independently represent a hydrogen atom, a fluorine atom, a monovalent aliphatic group, or a monovalent aromatic group; the monovalent aliphatic group and the monovalent aromatic group can contain at least one kind of atom selected from the group consisting of halogen atom, nitrogen atom, oxygen atom, sulfur atom, and silicon atom; $R_3$ and $R_4$ bonded to adjacent carbon atoms can be joined to form a ring, and $R_5$ and $R_6$ bonded to adjacent carbon atoms can be joined to form a ring; and n represents a real number of 1 or more.

5. The power storage device according to claim 1, wherein the polymer is a one-linking polymer in which adjacent two repeat units Y are linked by one repeat unit X, and the one-linking polymer includes at least one selected from the group consisting of repeat units Z6, Z7, Z8, Z9, and Z10 represented by the following general formulae (Z6), (Z7), (Z8), (Z9), and (Z10), respectively,

[Chem. 4]

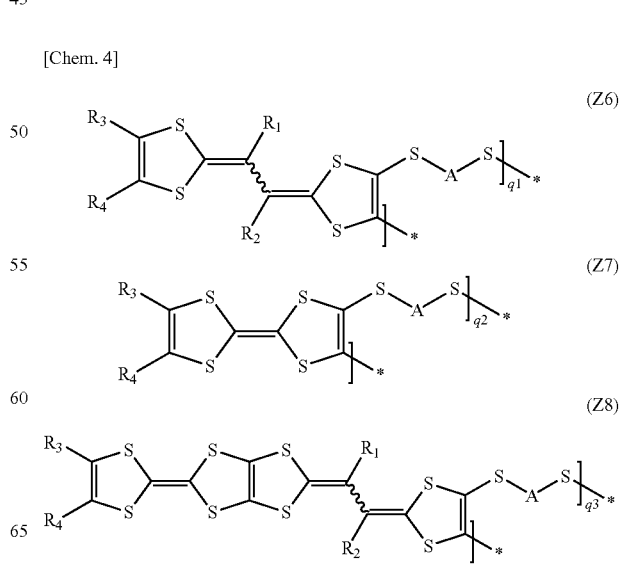

-continued

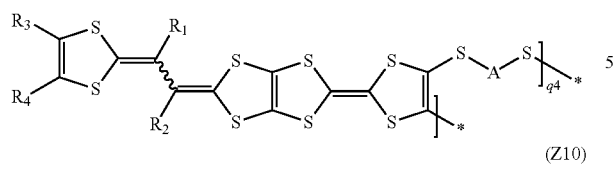
(Z9)

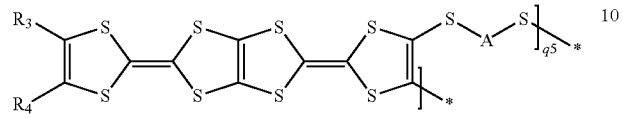
(Z10)

where in the formulas (Z6) to (Z10), A, $R_1$, and $R_2$ are as defined above; $R_3$ and $R_4$ each independently represent a hydrogen atom, a fluorine atom, a monovalent aliphatic group, or a monovalent aromatic group; the monovalent aliphatic group and the monovalent aromatic group can contain at least one kind of atom selected from the group consisting of halogen atom, nitrogen atom, oxygen atom, sulfur atom, and silicon atom; and q1 to q5 each represent the total number of repetition of the repeat units Z6 to Z10 in the one-linking polymer and represent a real number of 2 or more.

6. The power storage device according to claim 1,
wherein the polymer is a one-linking polymer (2) in which adjacent two repeat units Y are linked by one repeat unit X, and the one-linking polymer (2) is at least one selected from the group consisting of polymers 2a, 2b, 2c, 2d, 2e, and 2f represented by the following general formulae (2a), (2b), (2c), (2d), (2e), and (2f), respectively,

[Chem. 5]

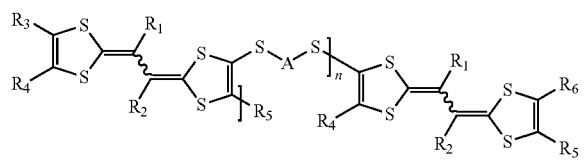
(2a)

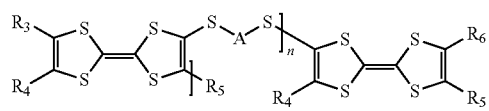
(2b)

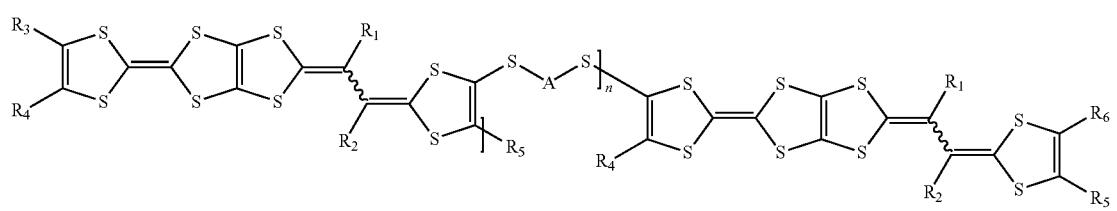
(2c)

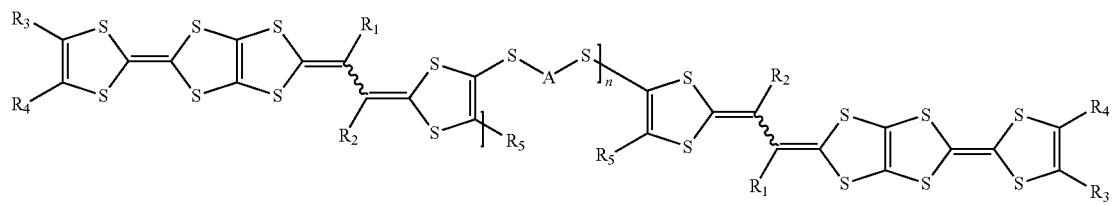
(2d)

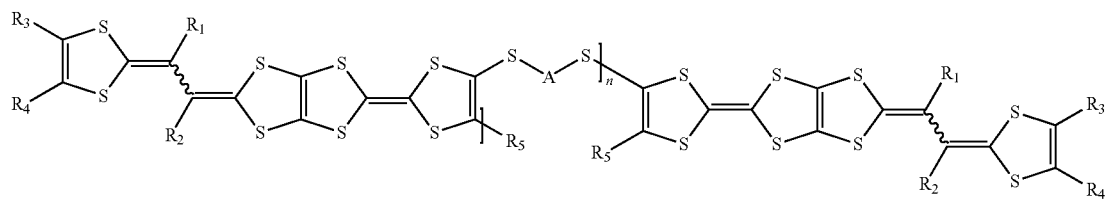
(2e)

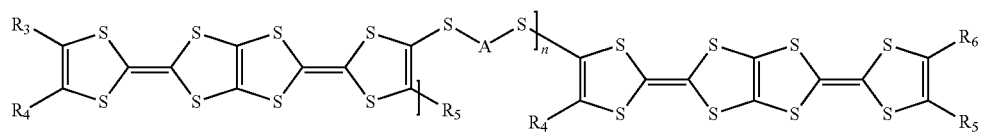
(2f)

where in the formulae (2a) to (2f), A, $R_1$ and $R_2$ are as defined above; $R_3$ to $R_6$ each independently represent a hydrogen atom, a fluorine atom, a monovalent aliphatic group, or a monovalent aromatic group; the monovalent aliphatic group and the monovalent aromatic group can contain at least one kind of atom selected from the group consisting of halogen atom, nitrogen atom, oxygen atom, sulfur atom, and silicon atom; $R_3$ and $R_4$ bonded to adjacent carbon atoms can be joined to form a ring, and $R_5$ and $R_6$ bonded to adjacent carbon atoms can be joined to form a ring; and n represents a real number of 1 or more.

7. The power storage device according to claim 1, wherein the polymer is a two-linking polymer in which adjacent two repeat units Y are linked by two repeat units X, and the two-linking polymer includes at least one selected from the group consisting of repeat units Z11, Z12, Z13, and Z14 represented by the following general formulae (Z11), (Z12), (Z13), and (Z14), respectively,

[Chem. 6]

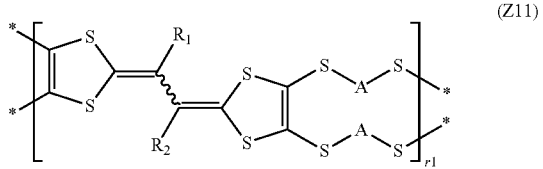

(Z11)

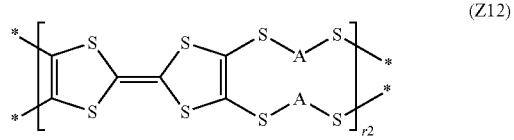

(Z12)

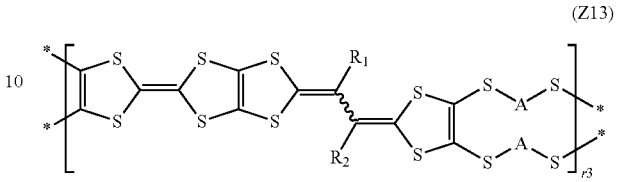

(Z13)

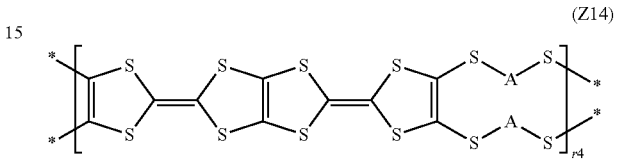

(Z14)

where in the formulae (Z11) to (Z14), A, $R_1$, and $R_2$ are as defined above; and r1 to r4 each represent the total number of repetition of the repeat units Z11 to Z14 in the two-linking polymer and represent a real number of 2 or more.

8. The power storage device according to claim 1, wherein the polymer is a two-linking polymer (3) in which adjacent two repeat units Y are linked by two repeat units X, and the two-linking polymer (3) is at least one selected from the group consisting of polymers 3a, 3b, 3c, 3d, 3e, and 3f represented by the following general formulae (3a), (3b), (3c), (3d), (3e), and (3f), respectively,

[Chem. 7]

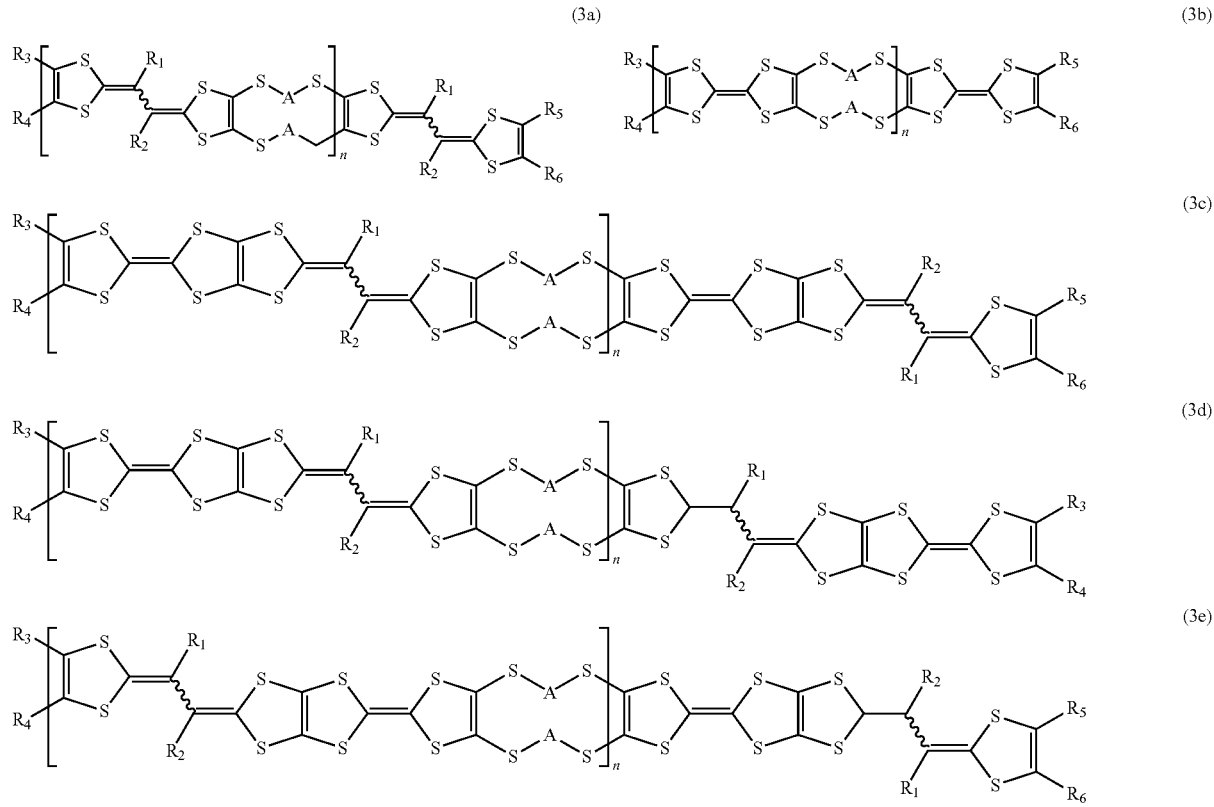

-continued (3f)

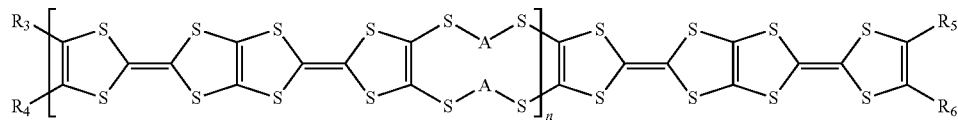

where in the formulae (3a) to (3f), A, $R_1$ and $R_2$ are as defined above; $R_3$ to $R_6$ each independently represent a hydrogen atom, a fluorine atom, a monovalent aliphatic group, or a monovalent aromatic group; the monovalent aliphatic group and the monovalent aromatic group can contain at least one kind of atom selected from the group consisting of halogen atom, nitrogen atom, oxygen atom, sulfur atom, and silicon atom; $R_3$ and $R_4$ bonded to adjacent carbon atoms can be joined to form a ring, and $R_5$ and $R_6$ bonded to adjacent carbon atoms can be joined to form a ring; and n represents a real number of 1 or more.

9. The power storage device according to claim 1,
wherein the polymer is an irregularly-linking polymer (4) having a portion in which adjacent two repeat units Y are linked by one repeat unit X and a portion in which adjacent two repeat units Y are linked by two repeat units X, and the irregularly-linking polymer (4) includes at least one selected from the group consisting of repeat units Z1, Z2, Z3, and Z4 represented by the following general formulae (Z1), (Z2), (Z3), and (Z4), respectively, and at least one selected from the group consisting of repeat units Z11, Z12, Z13, and Z14 represented by the following general formulae (Z11), (Z12), (Z13), and (Z14), respectively,

[Chem. 8]

(Z1)

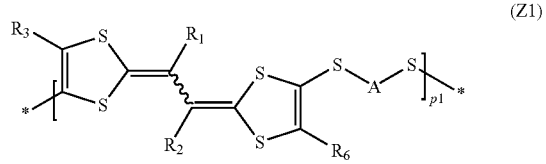

(Z2)

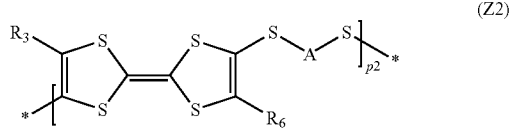

(Z3)

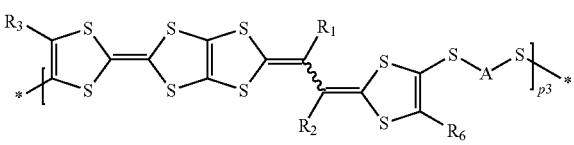

(Z4)

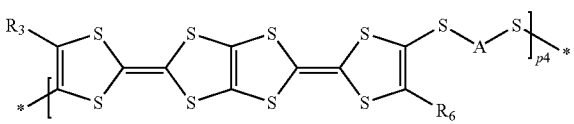

-continued (Z11)

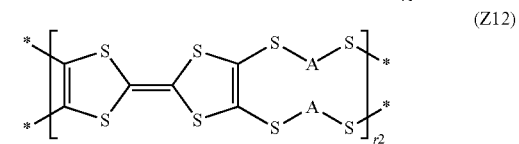

(Z12)

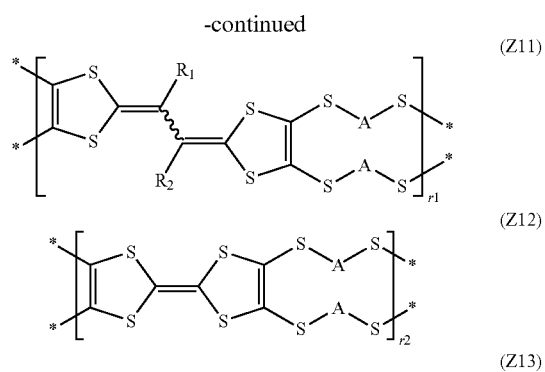

(Z13)

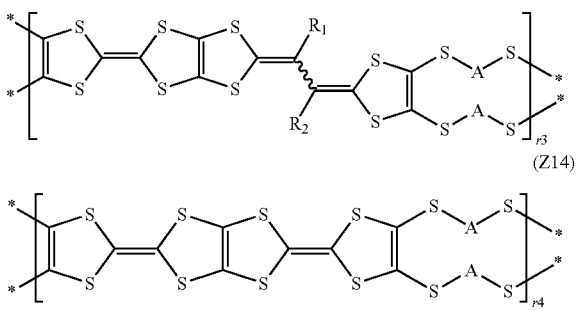

(Z14)

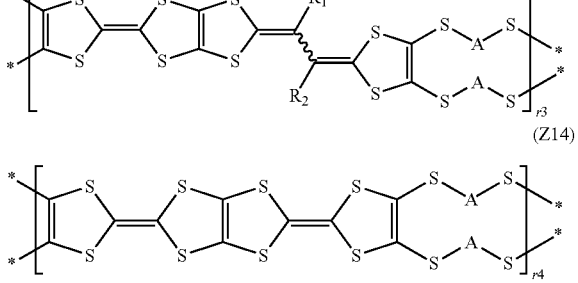

where in the formulae (Z1) to (Z4) and the formulae (Z11) to (Z14), A, $R_1$, and $R_2$ are as defined above; $R_3$ and $R_6$ each independently represent a hydrogen atom, a fluorine atom, a monovalent aliphatic group, or a monovalent aromatic group; the monovalent aliphatic group and the monovalent aromatic group can contain at least one kind of atom selected from the group consisting of halogen atom, nitrogen atom, oxygen atom, sulfur atom, and silicon atom; p1 to p4 each represent the total number of repetition of the repeat units Z1 to Z4 in the irregularly-linking polymer (4) and represent a real number of 1 or more; and r1 to r4 each represent the total number of repetition of the repeat units Z11 to Z14 in the irregularly-linking polymer (4) and represent a real number of 1 or more.

10. The power storage device according to claim 1, wherein the divalent aliphatic group is an alkylene group, an alkenylene group, or an alkynylene group.

11. The power storage device according to claim 1,
wherein in the divalent group -E-D-E-, the divalent alicyclic group represented by the character D is a cycloalkylene group, and
the divalent aliphatic groups represented by the character E are each independently an alkylene group, an alkenylene group, or an alkynylene group.

12. The power storage device according to claim 1,
wherein in the divalent group -E-D-E-, the divalent aromatic group represented by the character D is an arylene group, and
the divalent aliphatic groups represented by the character E are alkylene groups, alkenylene groups, or alkynylene groups.

13. The power storage device according to claim 1, wherein the monovalent aliphatic group is a monovalent group represented by the formula —$(S)_f$—Rb or the formula —$(S)_f$—Ra—$(CO-O)_g$—Rb where Ra represents an alkylene group; Rb represents a monovalent aliphatic group; the monovalent aliphatic group can contain at least one kind of atom selected from the group consisting of halogen atom, nitrogen atom, oxygen atom, sulfur atom, and silicon atom; and f and g each independently represent 0 or 1.

14. The power storage device according to claim 1, wherein the monovalent aromatic group is a monovalent group represented by the formula —$(S)_h$—$(Ra)_i$—Rc where Ra represents an alkylene group; Rc represents a monovalent aromatic group; the monovalent aromatic group can contain at least one kind of atom selected from the group consisting of halogen atom, nitrogen atom, oxygen atom, sulfur atom, and silicon atom; and h and i each independently represent 0 or 1.

15. The power storage device according to claim 1, wherein the total number of repetition of the repeat unit Y in the polymer is 6 or more.

16. The power storage device according to claim 1, wherein the electrolyte includes a non-aqueous solvent with a dielectric constant of 10 to 30 and a supporting salt comprising an anion and a cation dissolved in the non-aqueous solvent.

17. The power storage device according to claim 1, wherein the non-aqueous solvent is a mixture of a non-aqueous solvent with a dielectric constant of 10 or less and a non-aqueous solvent with a dielectric constant of 30 or more.

18. The power storage device according to claim 17, wherein the non-aqueous solvent with a dielectric constant of 10 or less is at least one selected from the group consisting of chain carbonic acid esters, chain carboxylic acid esters, and chain ethers, and the non-aqueous solvent with a dielectric constant of 30 or more is at least one selected from the group consisting of cyclic carbonic acid esters and cyclic ethers.

19. The power storage device according to claim 1, wherein the cation includes a quaternary ammonium ion.

20. The power storage device according to claim 1, wherein the cation includes a lithium ion.

21. The power storage device according to claim 1, wherein the negative electrode includes lithium metal, a lithium alloy, or a material capable of absorbing and desorbing lithium ions.

22. An electronic device including the power storage device of claim 1 as a power source.

23. A transportation device including the power storage device of claim 1 as a power source.

\* \* \* \* \*